United States Patent
Geva et al.

(10) Patent No.: US 10,668,283 B2
(45) Date of Patent: Jun. 2, 2020

(54) BRAIN STIMULATION TOOL CONFIGURATION

(71) Applicant: Elminda Ltd., Herzliya (IL)

(72) Inventors: Amir B. Geva, Tel-Aviv (IL); Ziv Peremen, Natanya (IL); Yaki Stern, Moshav Sde Yaakov (IL); Amit Reches, Binyamina (IL)

(73) Assignee: Elminda Ltd., Herzliya (IL)

( * ) Notice: Subject to any disclaimer, the term of this patent is extended or adjusted under 35 U.S.C. 154(b) by 448 days.

(21) Appl. No.: 15/514,550

(22) PCT Filed: Sep. 24, 2015

(86) PCT No.: PCT/IL2015/050972
§ 371 (c)(1),
(2) Date: Mar. 27, 2017

(87) PCT Pub. No.: WO2016/046830
PCT Pub. Date: Mar. 31, 2016

(65) Prior Publication Data
US 2017/0216595 A1 Aug. 3, 2017

Related U.S. Application Data

(60) Provisional application No. 62/056,556, filed on Sep. 28, 2014.

(51) Int. Cl.
*A61N 1/36* (2006.01)
*A61N 5/06* (2006.01)
(Continued)

(52) U.S. Cl.
CPC .......... *A61N 1/36025* (2013.01); *A61B 5/048* (2013.01); *A61B 5/0484* (2013.01);
(Continued)

(58) Field of Classification Search
CPC ............ A61N 1/36025; A61N 1/36139; A61N 2005/0626; A61N 7/00; A61N 5/0622;
(Continued)

(56) References Cited

U.S. PATENT DOCUMENTS

| 7,769,463 B2 | 8/2010 | Katsnelson |
| 2005/0165327 A1* | 7/2005 | Thibault .............. A61B 3/0066 600/558 |

(Continued)

FOREIGN PATENT DOCUMENTS

| WO | WO 2013/011515 | 1/2013 |
| WO | WO 2014/076698 | 5/2014 |
| WO | WO 2016/046830 | 3/2016 |

OTHER PUBLICATIONS

International Preliminary Report on Patentability dated Apr. 6, 2017 From the International Bureau of WIPO Re. Application No. PCT/IL2015/50972. (13 Pages).
(Continued)

*Primary Examiner* — Navin Natnithithadha
*Assistant Examiner* — Sunita Reddy

(57) ABSTRACT

A method of configuring a local brain stimulation tool is disclosed. The method comprises: obtaining a reference brain network activity (BNA) pattern, and a BNA pattern describing a neurophysiological state of the subject, each of the BNA patterns having a plurality of nodes and each node representing a brain location and at least one brain wave frequency. The method further comprises comparing the BNA patterns; and configuring the local brain stimulation tool to apply local brain stimulation at a frequency selected based on the comparison.

24 Claims, 37 Drawing Sheets
(26 of 37 Drawing Sheet(s) Filed in Color)

(51) Int. Cl.
  *A61N 7/00* (2006.01)
  *A61N 1/05* (2006.01)
  *A61N 1/20* (2006.01)
  *A61N 2/00* (2006.01)
  *A61B 5/00* (2006.01)
  *A61B 5/048* (2006.01)
  *A61B 5/0484* (2006.01)
  *A61N 5/067* (2006.01)

(52) U.S. Cl.
  CPC .......... *A61B 5/4064* (2013.01); *A61B 5/4836* (2013.01); *A61N 1/0534* (2013.01); *A61N 1/20* (2013.01); *A61N 1/36139* (2013.01); *A61N 2/006* (2013.01); *A61N 5/0622* (2013.01); *A61N 7/00* (2013.01); *A61N 2005/067* (2013.01); *A61N 2005/0626* (2013.01); *A61N 2007/0026* (2013.01)

(58) Field of Classification Search
  CPC .. A61N 1/20; A61N 1/0534; A61N 2005/067; A61N 2007/0026; A61N 2/006; A61B 5/4836; A61B 5/4064; A61B 5/048; A61B 5/0484
  USPC ...................................................... 600/9–15
  See application file for complete search history.

(56) References Cited

U.S. PATENT DOCUMENTS

| | | |
|---|---|---|
| 2005/0165458 A1 | 7/2005 | Boveja et al. |
| 2007/0027406 A1* | 2/2007 | LaPlaca ................. A61B 5/16 600/558 |
| 2008/0208073 A1* | 8/2008 | Causevic ............... A61B 5/048 600/544 |
| 2009/0264785 A1* | 10/2009 | Causevic ............. A61B 5/0476 600/544 |
| 2009/0318747 A1 | 12/2009 | Fischell et al. |
| 2010/0087698 A1 | 4/2010 | Hoffman |
| 2010/0191139 A1* | 7/2010 | Jacquin ................ A61B 5/0476 600/544 |
| 2010/0222694 A1* | 9/2010 | Causevic ............... A61B 5/048 600/544 |
| 2011/0028827 A1* | 2/2011 | Sitaram ................ A61B 5/0059 600/410 |
| 2012/0296569 A1* | 11/2012 | Shahaf .................. A61B 5/048 702/19 |
| 2013/0066394 A1 | 3/2013 | Saab |
| 2013/0331685 A1 | 12/2013 | Liu et al. |
| 2014/0163328 A1 | 6/2014 | Geva et al. |
| 2014/0249352 A1 | 9/2014 | Zangen et al. |

OTHER PUBLICATIONS

International Search Report and the Written Opinion dated May 3, 2016 From the International Searching Authority Re. Application No. PCT/IL2015/50972.

Invitation to Pay Additional Fees dated Feb. 29, 2016 From the International Searching Authority Re. Application No. PCT/IL2015/50972.

Peterchev et al. "ECT Stimulus Parameters: Rethinking Dosage", The Journal of ECT, 26(3): 159-174, Sep. 2010.

Supplementary European Search Report and the European Search Opinion dated Jun. 7, 2018 From the European Patent Office Re. Application No. 15843981.0. (7 Pages).

* cited by examiner

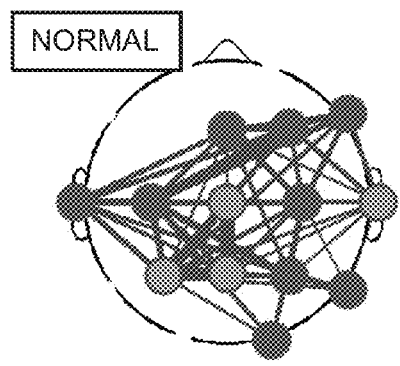
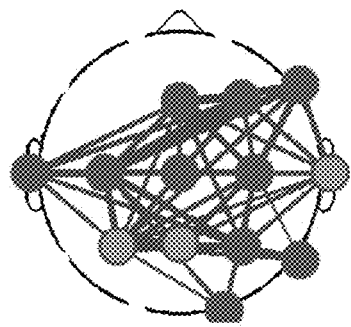
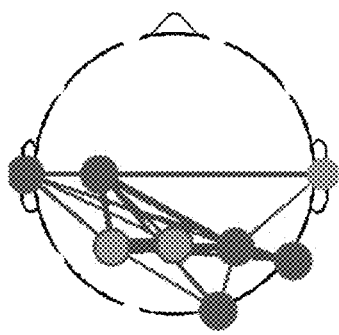
FIG. 5A  FIG. 5B  FIG. 5C
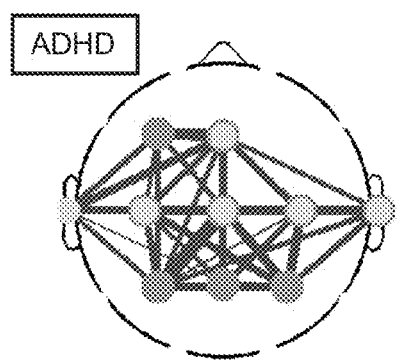
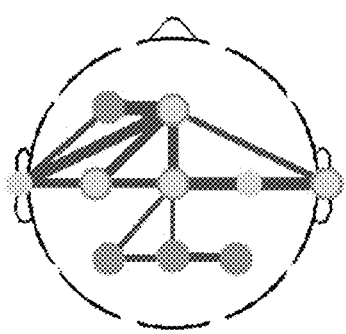
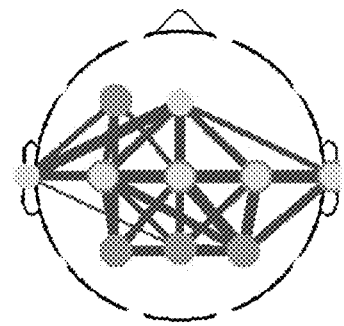
FIG. 5D  FIG. 5E  FIG. 5F

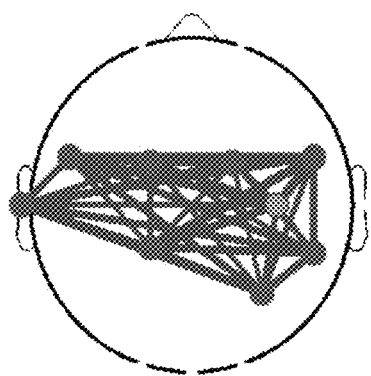
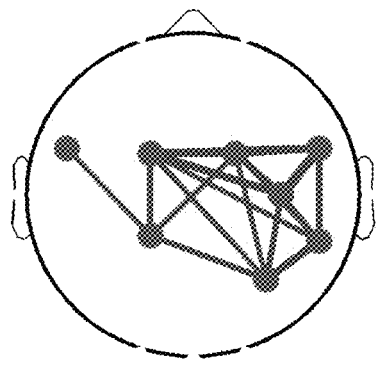
FIG. 9A　　　　　　　　　　FIG. 9B
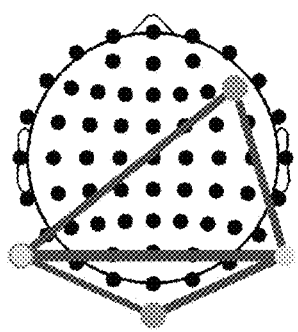
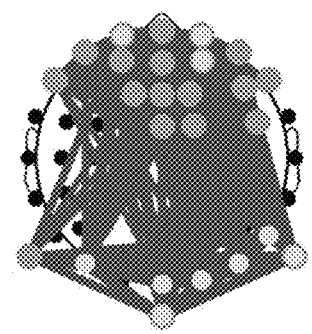
FIG. 10A　　　　　　　　　　FIG. 10B
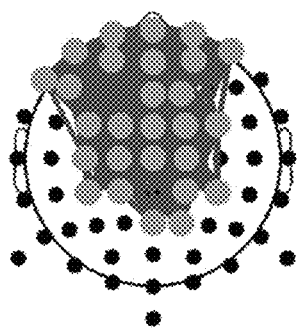
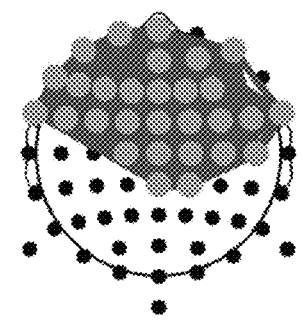
FIG. 10C　　　　　　　　　　FIG. 10D ———— Healthy    ———— mTBI GO (Response Execution)

Absolute Time

Sensitivity: 85%
Specificity: 58%
AUC: 0.74

FREQUENT ( Sensory Response )

Absolute Time

Sensitivity: 82%
Specificity: 59%
AUC: 0.76

Relative Time

Sensitivity: 74%
Specificity: 68%
AUC: 0.73

Relative Time

Sensitivity: 85%
Specificity: 59%
AUC: 0.70

BRAIN STIMULATION TOOL CONFIGURATION

RELATED APPLICATIONS

This application is a National Phase of PCT Patent Application No. PCT/IL2015/050972 having International filing date of Sep. 24, 2015, which claims the benefit of priority under 35 USC § 119(e) of U.S. Provisional Patent Application No. 62/056,556 filed on Sep. 28, 2014. The contents of the above applications are all incorporated by reference as if fully set forth herein in their entirety.

FIELD AND BACKGROUND OF THE INVENTION

The present invention, in some embodiments thereof, relates to neurophysiology and, more particularly, but not exclusively, to method and system for configuring a brain stimulation tool.

Little is known about the mechanisms that allow the brain to selectively improve the neural representations of behaviorally important stimuli while ignoring irrelevant stimuli. The brain is a complex structure of nerve cells that produce signals called action potentials. These action potentials move from one cell to another across a gap called the synapse. These potentials summate in the cortex and extend through the coverings of the brain to the scalp, where they can be measured using appropriate electrodes. Rhythmical measured activity represents postsynaptic cortical neuronal potentials which are synchronized by the complex interaction of large populations of cortical cells.

Behavioral functions are based upon flow among various functional regions in the brain, involving specific spatiotemporal flow patterns. A specific spatiotemporal pattern underlying a certain behavioral function is composed of functional brain regions, which are often active for at least several tens of milliseconds and more. The flow of activity among those regions is often synchronization-based.

Known in the art are methods that identify discrete participating regions for the purpose of relating behavioral functions to their underlying localized brain activities. Other techniques employ analysis of the flow from one region to another.

U.S. Pat. No. 6,792,304 discloses a method and a system for mass communication assessment. A cognitive task is transmitted from a central control site to a plurality of remote test sites via Internet. The brain response of the subjects at the remote sites in response to the task is recorded and transmitted back to the central control site via the Internet. The central control site then computes the variations in the brain activities for the subjects at each of the selected sites.

U.S. Published Application No. 20040059241 discloses a method for classifying and treating physiologic brain imbalances. Neurophysiologic techniques are used for obtaining a set of analytic brain signals from a subject, and a set of digital parameters is determined from the signals. The digital parameters are quantitatively mapped to various therapy responsivity profiles. The signals and parameters for a subject are compared to aggregate neurophysiologic information contained in databases relating to asymptomatic and symptomatic reference populations, and the comparison is used for making treatment recommendations. Treatment response patterns are correlated as a dependent variable to provide a connection to successful outcomes for clinical treatment of afflicted subjects.

International Publication No. WO 2007/138579, the contents of which are hereby incorporated by reference, describes a method for establishing a knowledge base of neuropsychological flow patterns. Signals from multiple research groups for a particular behavioral process are obtained, and sources of activity participating in the particular behavioral functions are localized. Thereafter, sets of patterns of brain activity are identified, and neuropsychological analysis is employed for analyzing the localized sources and the identified patterns. The analysis includes identification and ranking of possible pathways. A set of flow patterns is then created and used as a knowledge base. The knowledge base is then used as a constraint for reducing the number of ranked pathways.

International Publication Nos. WO 2009/069134, WO 2009/069135 and WO 2009/069136, the contents of which are hereby incorporated by reference, describe a technique in which neurophysiological data are collected before and after the subject has performed a task and/or action that forms a stimulus. The stimulus is used for defining features in the data, and the data are decomposed according to the defined features. Thereafter, the features are analyzed to determine one or more patterns in the data. The decomposition can employ clustering for locating one or more important features in the data, wherein a collection of clusters forms an activity network. The data patterns can be analyzed for defining a neural model which can be used for simulating the effect of a particular pathology and/or treatment on the brain.

International Publication No. WO 2011/086563, the contents of which are hereby incorporated by reference, discloses analysis of neurophysiological data, which includes identifying activity-related features in the data, constructing a brain network activity (BNA) pattern having a plurality of nodes, each representing a feature of the activity-related features, and assigning a connectivity weight to each pair of nodes in the BNA pattern.

International Publication No. WO 2014/076698, the contents of which are hereby incorporated by reference, discloses a method of analyzing neurophysiological data recorded from a brain of a subject. Activity-related features are identified in the data, and the data are parcelized according to the activity-related features to define a plurality of capsules, each representing a spatiotemporal activity region in the brain. The defined capsules are compared to a reference capsule, and a brain function of the subject is estimated based on the comparison.

Additional background art includes U.S. Published Application No. 20050177058, which discloses a system in which EEG readings from more than one subject at the same or different locations are collected, analyzed and compared, when they are exposed to a common set of stimuli. The compatibility of the subjects is studied using their EEG readings, and concealed information is discovered or verified from.

SUMMARY OF THE INVENTION

According to an aspect of some embodiments of the present invention there is provided a method of configuring a local brain stimulation tool. The method comprises: obtaining a reference brain network activity (BNA) pattern, and a BNA pattern describing a neurophysiological state of the subject, each of the BNA patterns having a plurality of nodes and each node representing a brain location and at least one brain wave frequency. The method further comprises comparing the BNA patterns; and configuring the local brain stimulation tool to apply local brain stimulation at a frequency selected based on the comparison.

According to an aspect of some embodiments of the present invention there is provided a method of configuring a local brain stimulation tool, the method comprising: obtaining a reference brain network activity (BNA) pattern, and a BNA pattern describing a neurophysiological state of the subject, each of the BNA patterns having a plurality of nodes and each node representing a brain location and at least one brain wave frequency; comparing the BNA patterns; and configuring the local brain stimulation tool to apply local brain stimulation at a time or synchronization selected based on the comparison.

According to some embodiments of the invention the method further comprises configuring the tool to apply the local brain stimulation at a location selected based on the comparison.

According to some embodiments of the invention the method further comprises configuring the tool to apply the local brain stimulation at a time or synchronization selected based on the comparison.

According to some embodiments of the invention the invention the method further comprises correcting the location using a technique selected from the group consisting of a source localization procedure, Cortical Potential Imaging (CPI), and Cortical Source Density (CSD).

According to some embodiments of the invention the method further comprises operating the local brain stimulation tool to apply the local brain stimulation to the subject thereby to treat a brain disorder thereof, wherein both a frequency and a location of the stimulation is selected based on the comparison.

According to some embodiments of the invention the local brain stimulation tool is operated to apply local brain stimulation at a time selected based on the comparison.

According to some embodiments of the invention the local brain stimulation tool is operated to apply local brain stimulation at a plurality of different brain locations and a plurality of different frequencies.

According to some embodiments of the invention the local brain stimulation tool is operated to apply local brain stimulation at a plurality of different brain locations and a plurality of different times.

According to some embodiments of the invention the local brain stimulation tool is operated to apply local brain stimulation at a plurality of different brain locations, a plurality of different frequencies and a plurality of different times.

According to some embodiments of the invention the local brain stimulation tool is operated to apply local brain stimulation at a plurality of different brain locations, at the same frequency but at a plurality of different times.

According to some embodiments of the invention the brain disorder is a chronic abnormal brain function.

According to some embodiments of the invention the brain disorder is brain concussion.

According to some embodiments of the invention the comparison is node-wise, and wherein the selected location corresponds to a node that exists in the reference and missing in the BNA pattern describing the neurophysiological state of the subject.

According to some embodiments of the invention the comparison is node-wise, wherein the selected location corresponds to a node that exists in both the BNA patterns, and wherein the selected frequency exists in the node of the reference BNA and is missing or suppressed in the BNA pattern describing the neurophysiological state of the subject.

According to some embodiments of the invention the reference BNA pattern is the obtained by accessing a database of reference BNA patterns and selecting the reference BNA pattern from the database.

According to some embodiments of the invention the database of reference BNA patterns comprises annotated reference BNA patterns, and wherein the selection of the reference BNA pattern from the database is based, at least in part, on the annotations.

According to some embodiments of the invention the BNA pattern describing the neurophysiological state of the subject is a weighted BNA pattern, wherein each entry of the database is associated with a weight, and wherein the selection of the reference BNA pattern from the database is based, at least in part, on the weights.

According to some embodiments of the invention the reference BNA pattern is a baseline BNA pattern describing a previous neurophysiological state of the subject.

According to some embodiments of the invention the method further comprises obtaining a post-stimulation BNA pattern describing a neurophysiological state of the subject following the stimulation, comparing the post-stimulation BNA pattern with the BNA pattern describing the neurophysiological state before the stimulation, and assessing the effect of the stimulation based on the comparison.

According to some embodiments of the invention at least one node of the BNA patterns defines a capsule representing a spatiotemporal activity region in the brain.

According to some embodiments of the invention the comparison comprises calculating, for each of the at least some of the capsules, a statistical score of a spatiotemporal vector corresponding to the capsule using multidimensional statistical distribution describing a respective database capsule.

According to some embodiments of the invention the method comprises constructing at least one of the BNA patterns.

According to some embodiments of the invention the wherein the construction of at least one of the BNA patterns comprises: receiving neurophysiological data; identifying activity-related features in the data; and defining at least a portion of the activity-related features as nodes of the BNA pattern.

According to some embodiments of the invention the method comprises assigning a connectivity weight to each pair of nodes in the BNA pattern.

According to some embodiments of the invention the construction of the at least one of the BNA patterns comprises: receiving neurophysiological data; identifying activity-related features in the data; parceling the data according to the activity-related features to define a plurality of capsules, each representing a spatiotemporal activity region in the brain; and defining at least a portion of the capsules as nodes of the BNA pattern.

According to some embodiments of the invention the construction of the at least one of the BNA patterns comprises: receiving neurophysiological data; identifying activity-related features in the data; parceling the data according to the activity-related features to define a plurality of capsules, each representing a spatiotemporal activity region in the brain; clustering the data according to the capsules, to provide a plurality of capsule clusters; and defining at least a portion of the capsule clusters and/or representations thereof as nodes of the BNA pattern.

According to some embodiments of the invention the representations of the clusters comprises capsular representations of the clusters.

According to some embodiments of the invention the method comprises determining inter-capsule relations among the capsules, and defining connectivity weights between the nodes of the BNA pattern using the inter-capsule relations.

According to some embodiments of the invention the inter-capsule relation comprises at least one of spatial proximity between two defined capsules, temporal proximity between two defined capsules, spectral proximity between two defined capsules, and energetic proximity between two defined capsules.

According to some embodiments of the invention the local stimulation comprises both transcranial stimulation and deep brain stimulation, and wherein the transcranial stimulation is executed to control activation thresholds for the deep brain stimulation.

According to an aspect of some embodiments of the present invention there is provided a system for treating a subject. The system comprises: (a) a data processing system configured for: obtaining a reference brain network activity (BNA) pattern, and a BNA pattern describing a neurophysiological state of the subject, each of the BNA patterns having a plurality of nodes and each node representing a brain location and at least one brain wave frequency; and comparing the BNA patterns; and (b) a controller connectable to a brain stimulation tool and configured for controlling the brain stimulation tool to apply local brain stimulation at a location and a frequency selected based on the comparison.

According to some embodiments of the invention the local stimulation tool comprises a non-invasive stimulation tool.

According to some embodiments of the invention the local stimulation tool comprises a transcranial stimulation tool.

According to some embodiments of the invention the local stimulation tool comprises a transcranial electrical stimulation tool.

According to some embodiments of the invention the local stimulation tool comprises a transcranial magnetic stimulation tool.

According to some embodiments of the invention the local stimulation tool comprises a repetitive Transcranial Magnetic Stimulation (rTMS) tool.

According to some embodiments of the invention the local stimulation tool comprises a deep Transcranial magnetic stimulation (dTMS) tool.

According to some embodiments of the invention the local stimulation tool comprises a multichannel TMS and multichannel (dTMS) tool.

According to some embodiments of the invention the local stimulation tool comprises a transcranial electrical stimulations (tES) tool.

According to some embodiments of the invention the local stimulation tool comprises a Transcranial direct current stimulation (tDCS) tool.

According to some embodiments of the invention the local stimulation tool comprises a Transcranial alternate current stimulation (tACS) tool.

According to some embodiments of the invention the local stimulation tool comprises a Transcranial random noise stimulation (tRNS) tool.

According to some embodiments of the invention the local stimulation tool comprises a High definition tES (HD-tES) tool.

According to some embodiments of the invention the local stimulation tool comprises a High definition tDCS (HD-tDCS) tool.

According to some embodiments of the invention the local stimulation tool comprises a multichannel tES tool.

According to some embodiments of the invention the local stimulation tool comprises a focused ultrasound stimulation (FUS) tool.

According to some embodiments of the invention the local stimulation tool comprises an electroconvulsive therapy (ECT) tool.

According to some embodiments of the invention the local stimulation tool comprises an invasive stimulation tool.

According to some embodiments of the invention the local stimulation tool comprises a Deep brain stimulation (DBS) tool.

According to some embodiments of the invention the local stimulation tool comprises a multifocal deep brain stimulation tool.

According to some embodiments of the invention the method according to any wherein the local stimulation tool comprises a laser stimulation tool.

According to some embodiments of the invention the brain stimulation tool comprises an electrocortical stimulation tool configured to apply electrocortical stimulation on the cortex.

According to some embodiments of the invention the brain stimulation tool is configured to apply both transcranial stimulation and deep brain stimulation, and wherein the controller is configured to control the brain stimulation tool to apply the transcranial stimulation to control activation thresholds for the deep brain stimulation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flowchart diagram of a method suitable for analyzing neurophysiological data, according to various exemplary embodiments of the present invention.

FIG. 2 is a schematic illustration showing a representative example of a Brain Network Activity (BNA) pattern which can be extracted from neurophysiological data, according to some embodiments of the present invention.

FIG. 3A is a flowchart diagram describing a procedure for identifying activity-related features for a group of subjects, according to some embodiments of the present invention.

FIG. 3B is schematic illustration of a procedure for determining relations between brain activity features, according to some embodiments of the present invention.

Figure 3A:
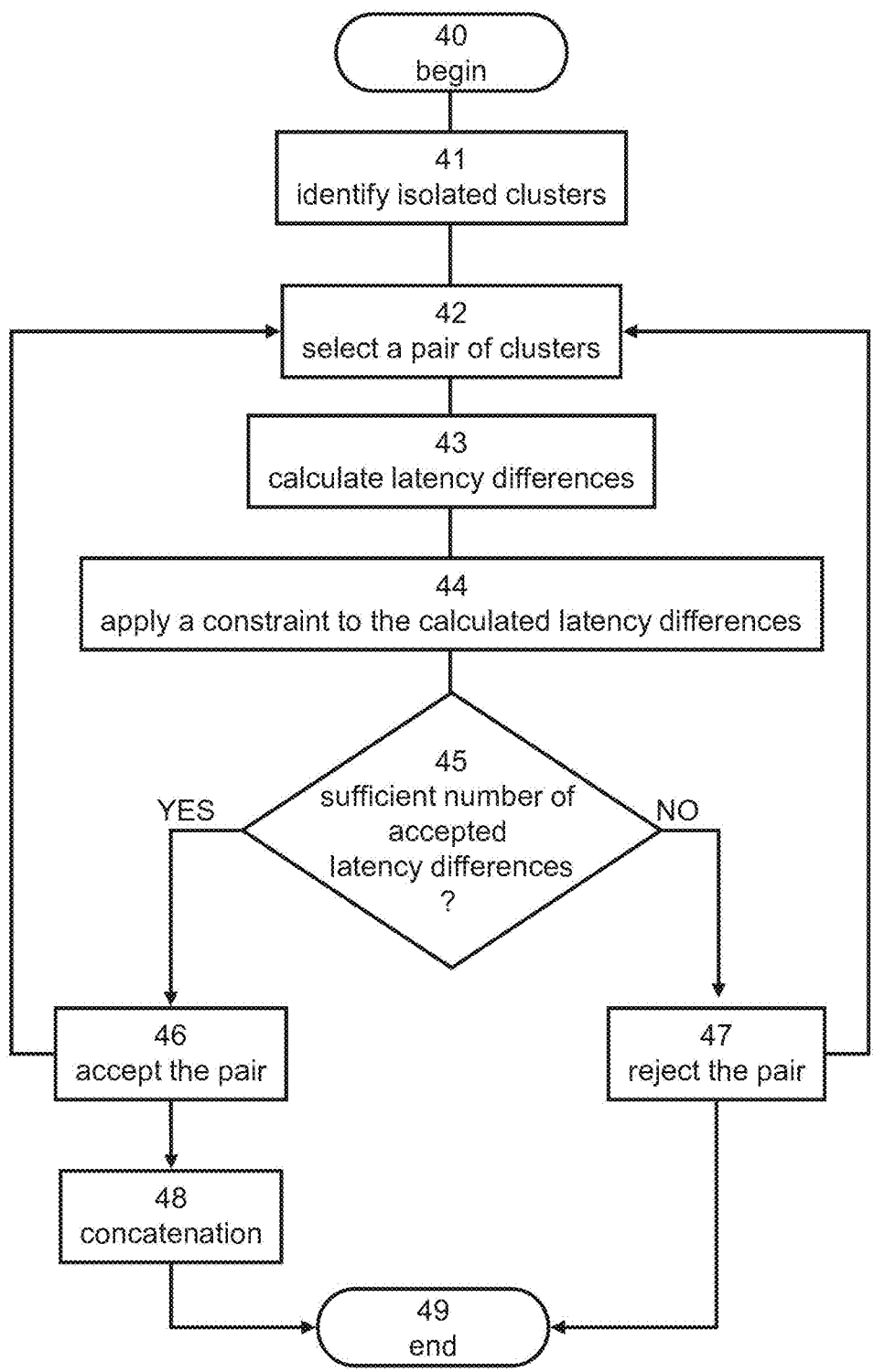
Figure 3B:
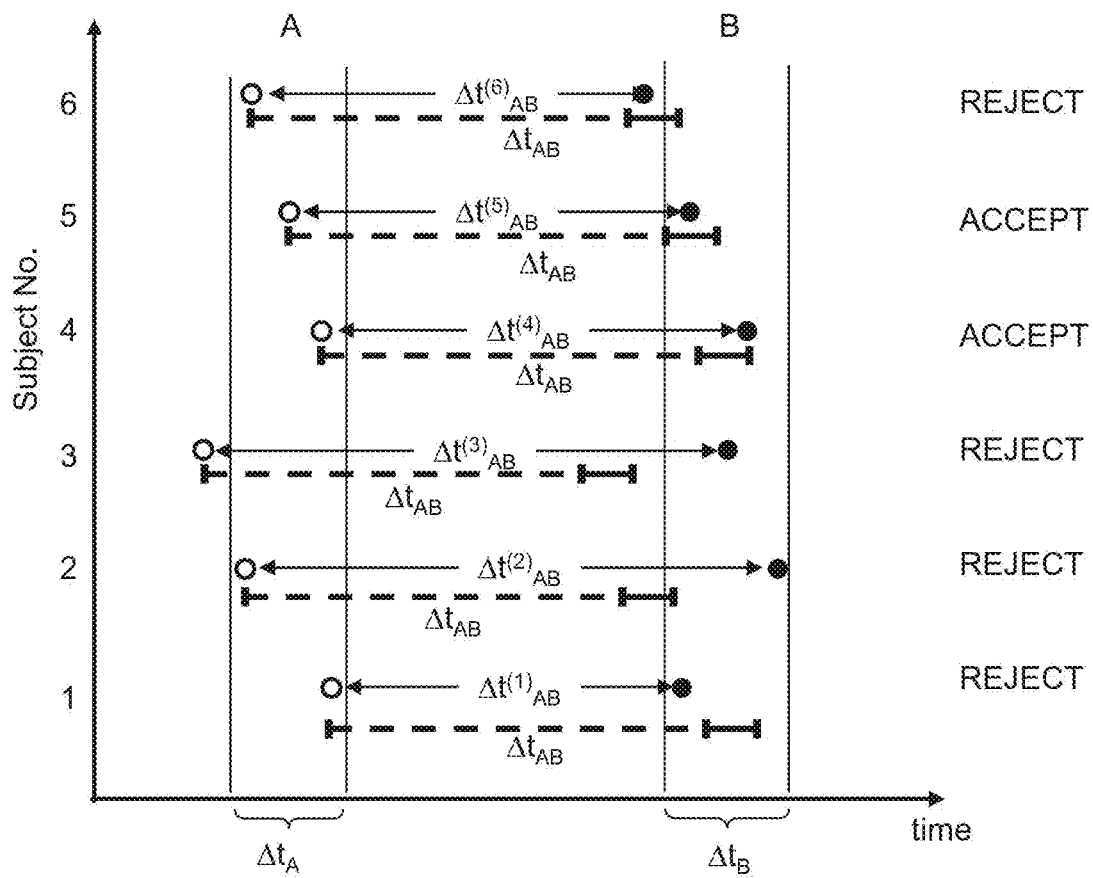
Figure 3C:
Figure 3D:
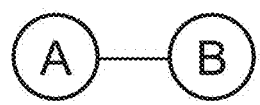
Figure 3E:

FIGS. 3C-E are abstract illustrations of a BNA patterns constructed according to some embodiments of the present invention using the procedure illustrated in FIG. 3B.

Figure 4:
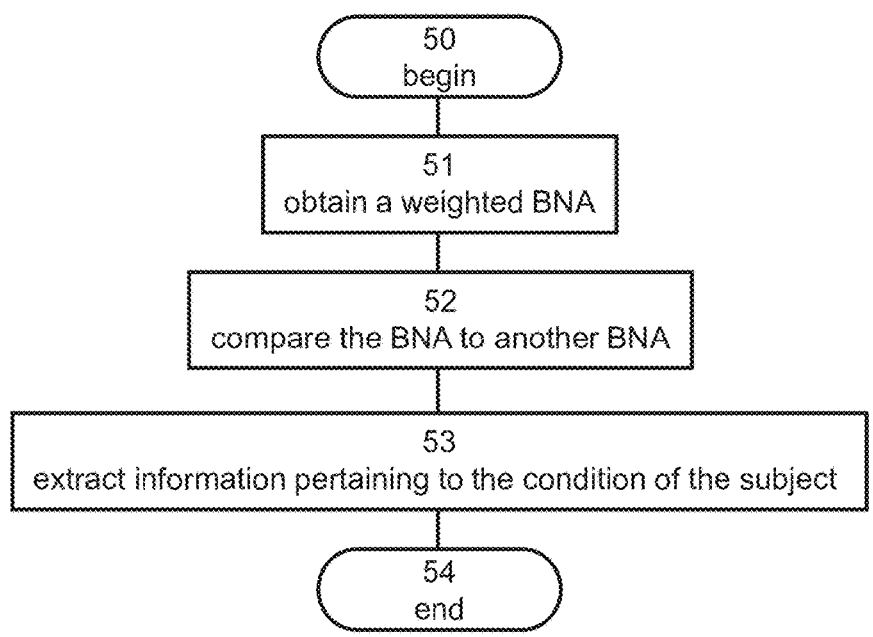

FIG. 4 is a flowchart diagram describing a method suitable for analyzing a subject-specific BNA pattern, according to various exemplary embodiments of the present invention.

FIGS. 5A-F are schematic illustrations showing a representative example for a process for determining a brain-disorder index, according to some embodiments of the present invention.

FIGS. 6A-F are schematic illustrations showing representative examples for a process for assessing the responsiveness of an ADHD subject to treatment, according to some embodiments of the present invention.

FIGS. 7A-D are schematic illustrations showing representative examples for a process for assessing the responsiveness of another ADHD subject to treatment, according to some embodiments of the present invention.

FIGS. 8A-E are schematic illustrations showing a representative example for a process for assessing the responsiveness of a subject to scopolamine, according to some embodiments of the present invention.

FIGS. 9A-B are schematic illustrations showing a representative example for use of the BNA pattern for measuring pain, according to some embodiments of the present invention.

FIGS. 10A-H are schematic illustrations of BNA patterns constructed according to some embodiments of the present invention from EEG data recorded during a working memory test.

Figure 11:
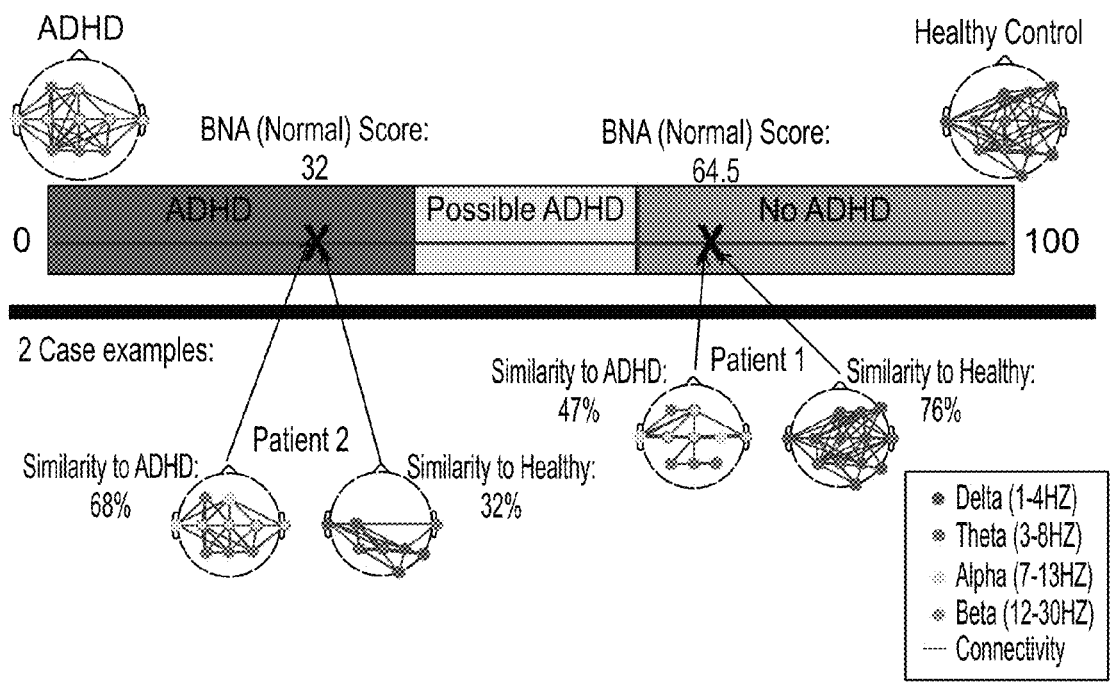

FIG. 11 shows graphical presentation of a brain-disorder index according to some embodiments of the present invention.

Figure 12:
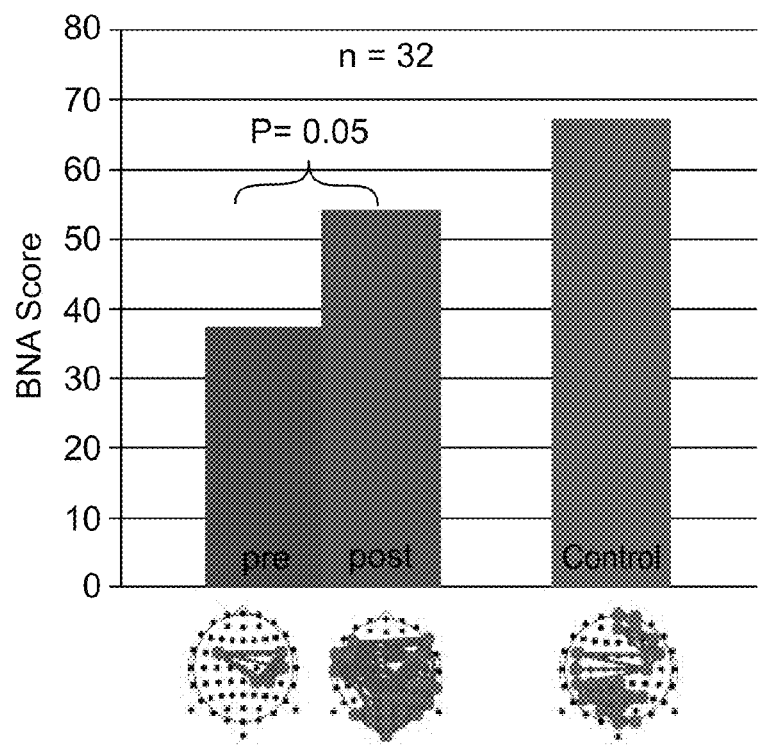

FIG. 12 shows results of a methylphenidate (MPH) study performed according to some embodiments of the present invention.

Figure 13:
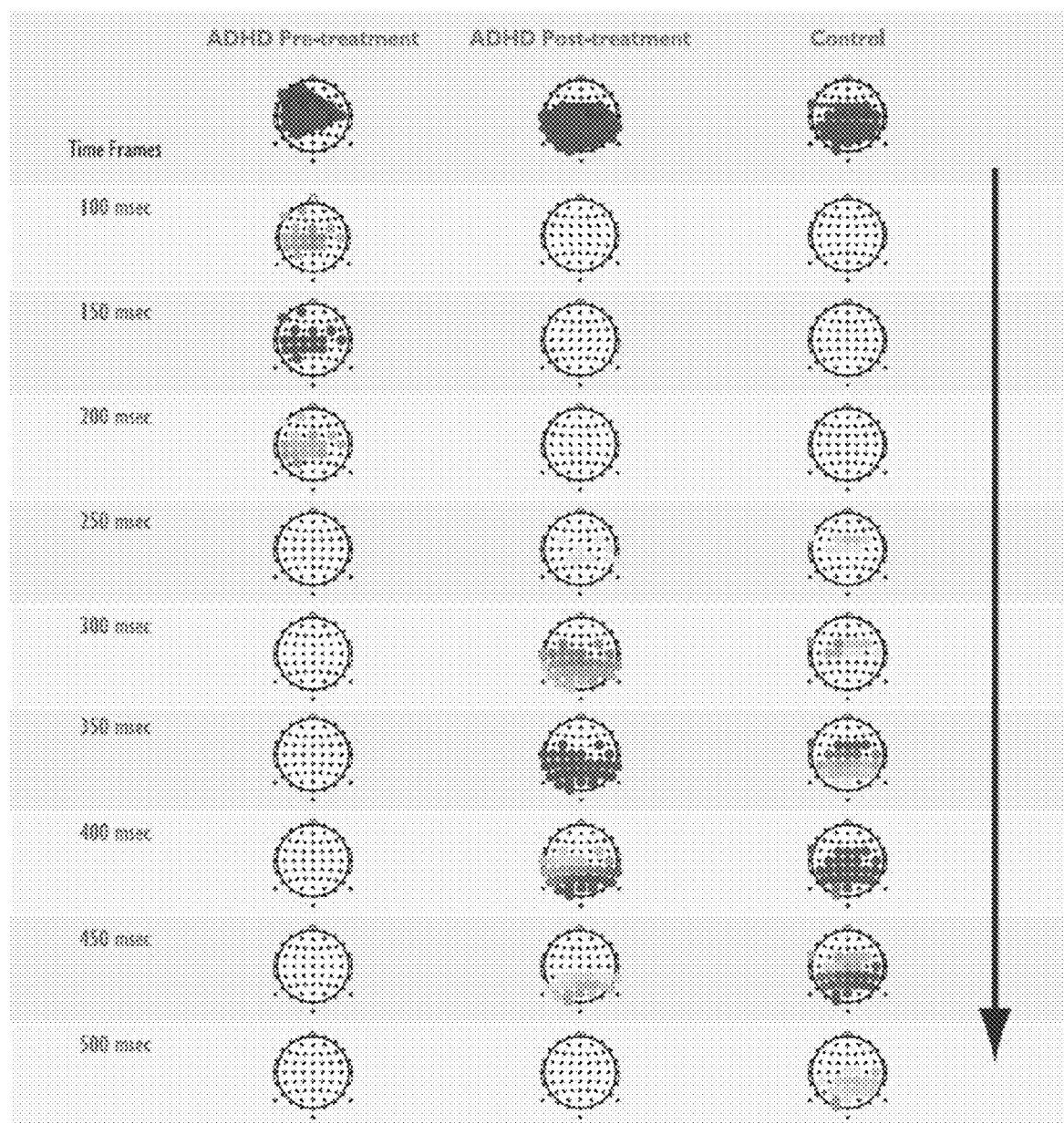

FIG. 13 shows evolutions of group BNA patterns of untreated ADHD subjects (left column), ADHD subjects following treatment with MPH (middle column), and control (right column).

Figure 14:
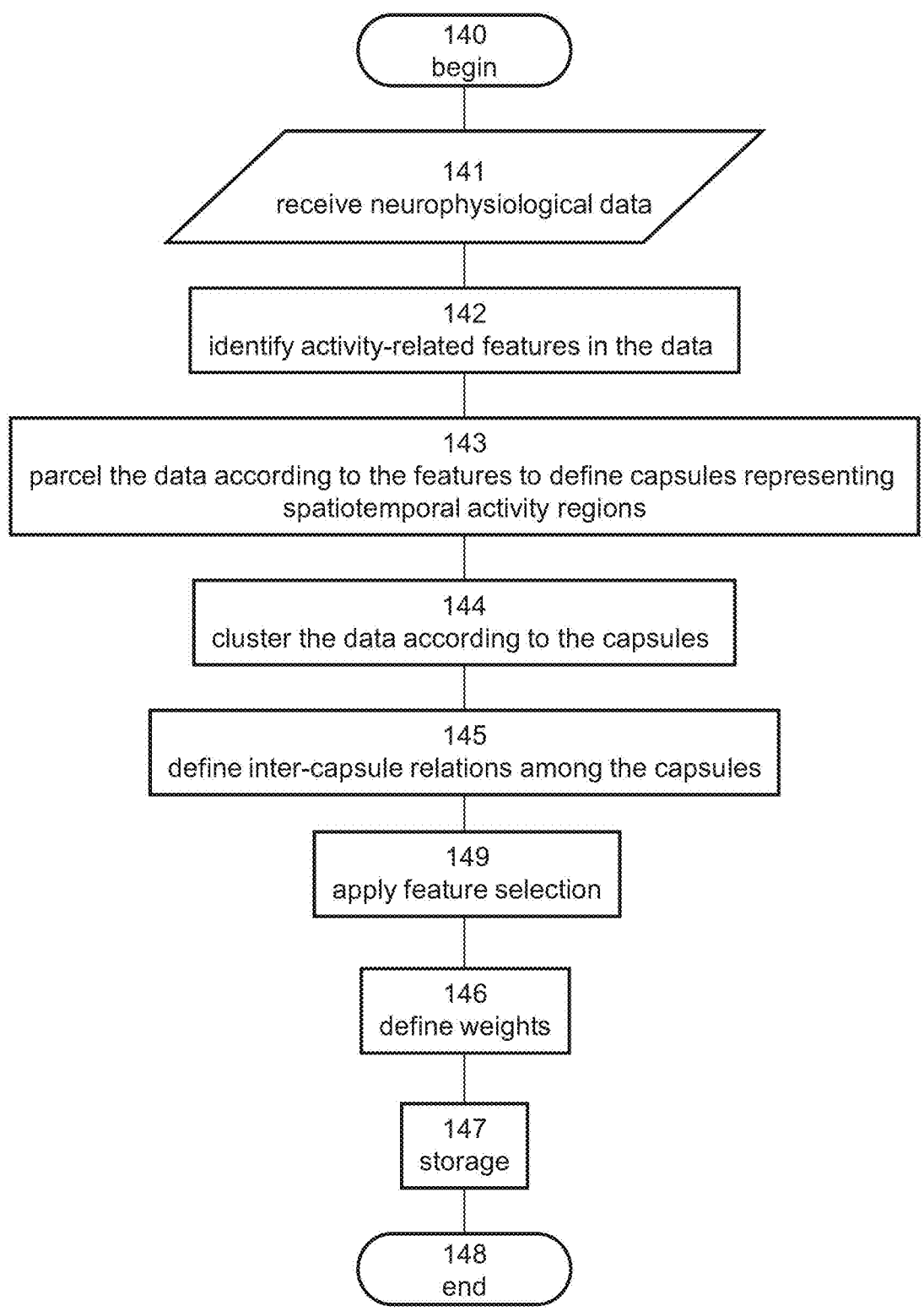

FIG. 14 is a flowchart diagram illustrating a method suitable for constructing a database from neurophysiological data recorded from a group of subjects, according to some embodiments of the present invention.

Figure 15:
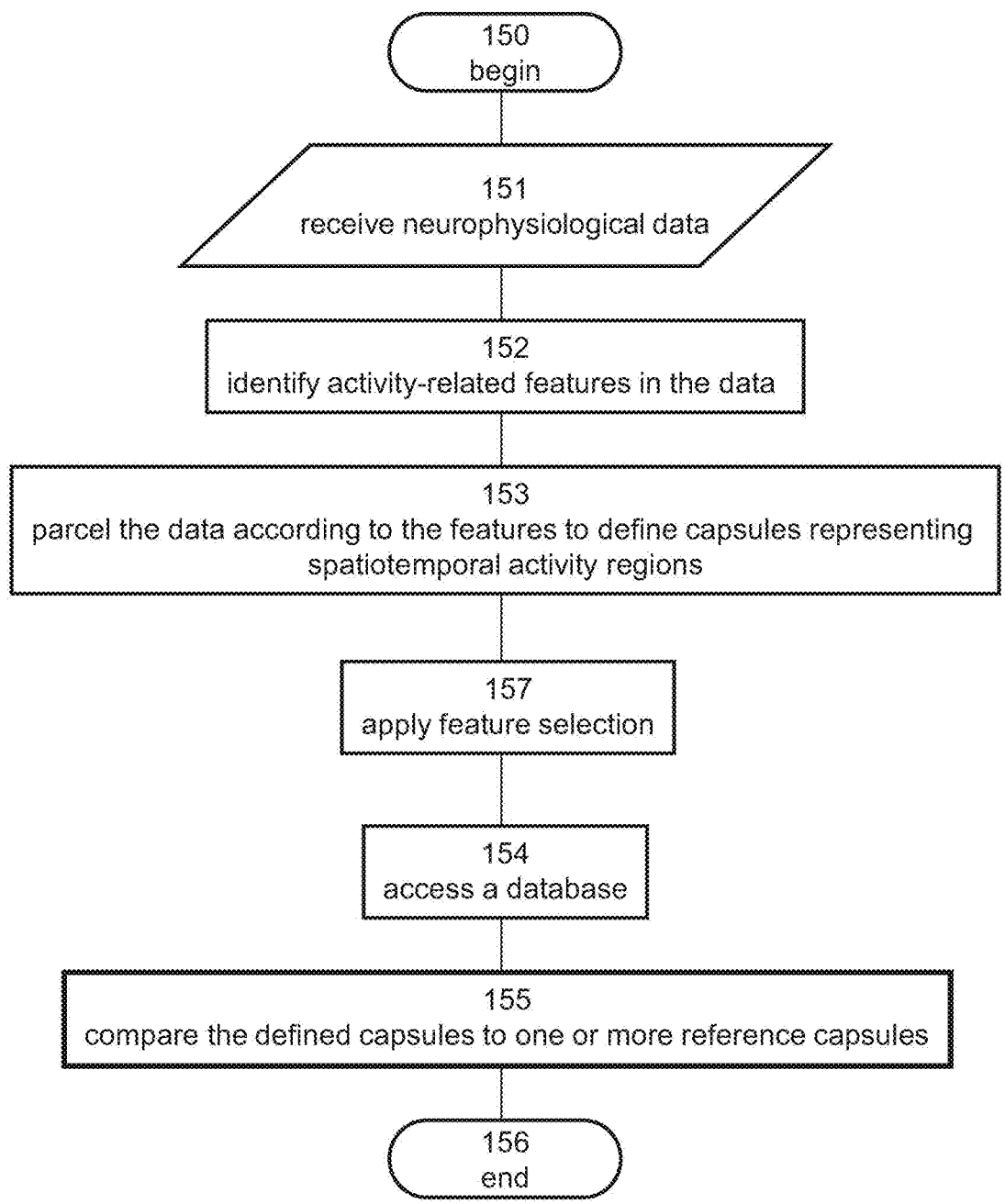

FIG. 15 is a flowchart diagram illustrating a method suitable for analyzing neurophysiological data recorded from a subject, according to some embodiments of the present invention.

Figure 16:
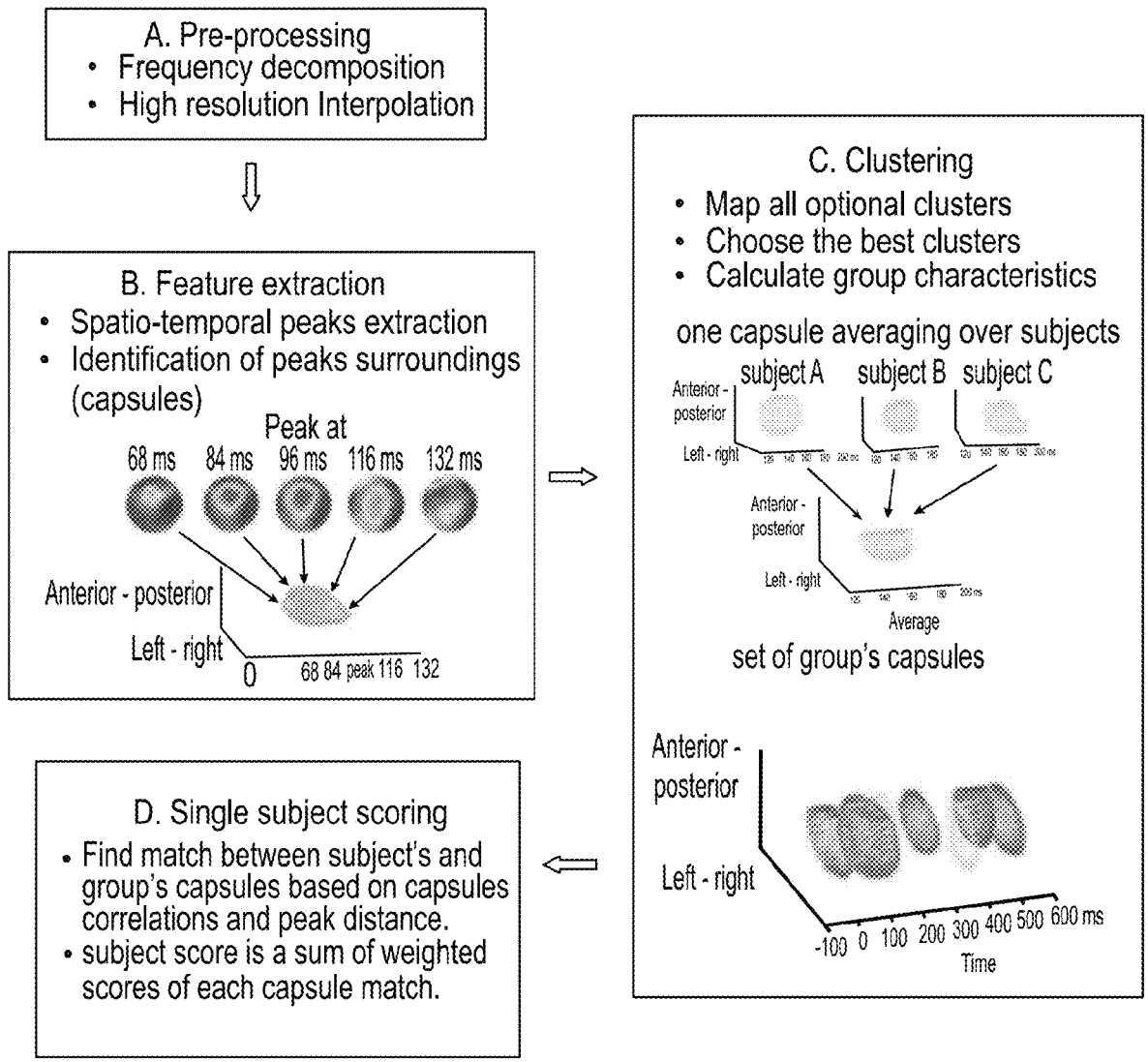

FIG. 16 is a block diagram of a data analysis technique executed in an experiment performed according to some embodiments of the present invention.

Figure 17A:
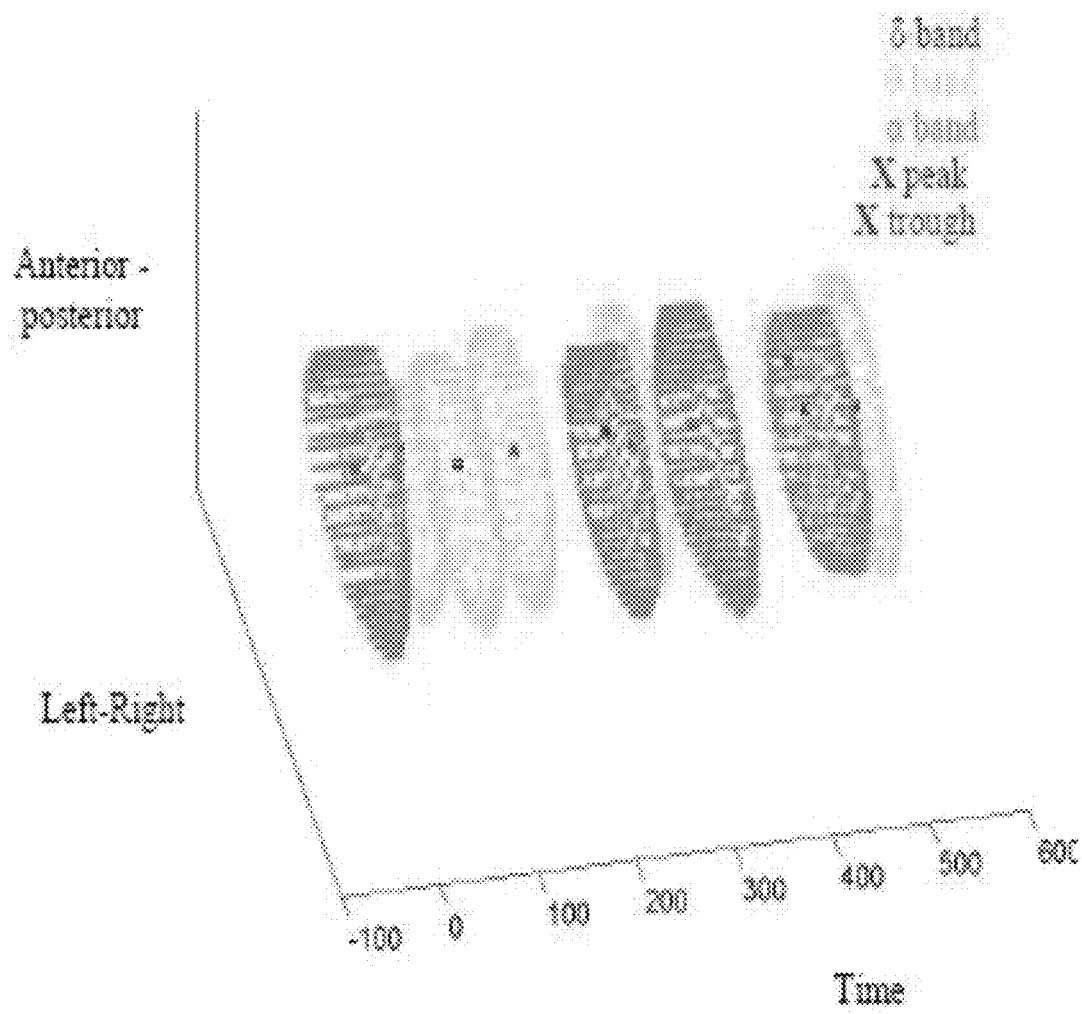
Figure 17B:
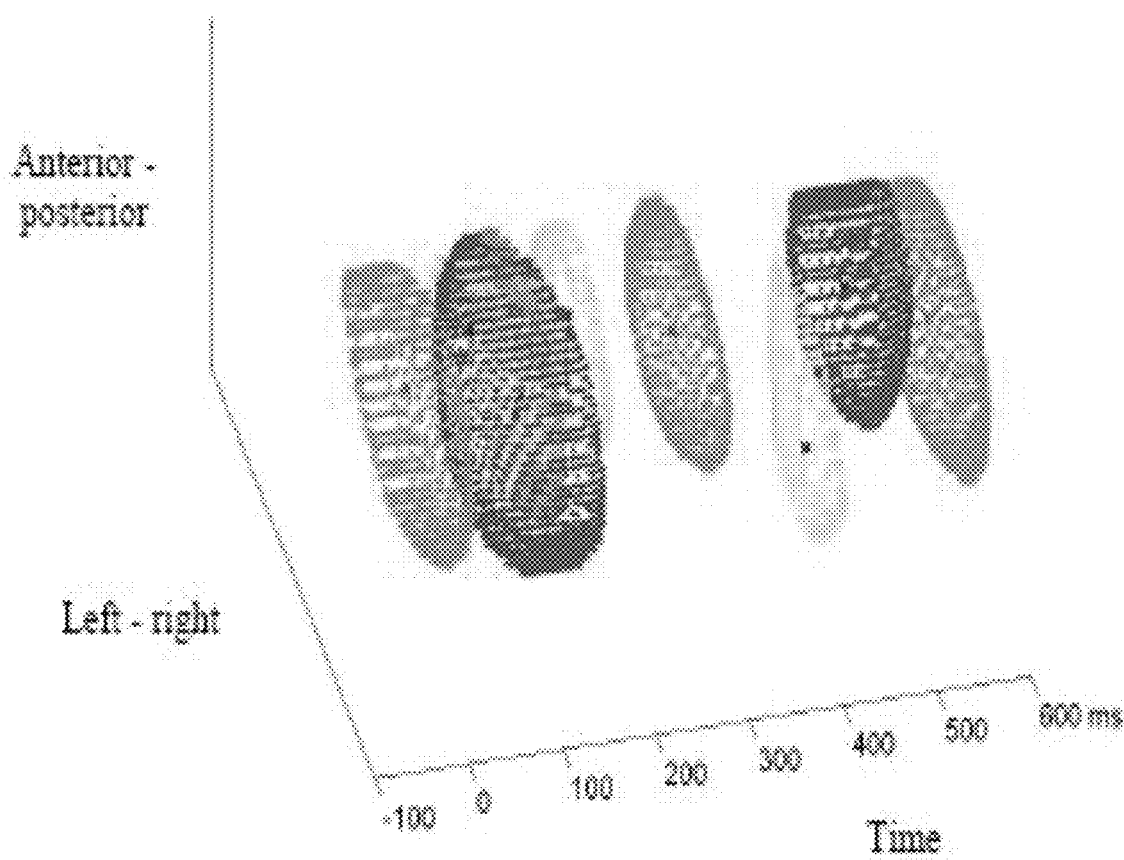

FIGS. 17A and 17B show Groups' capsules as obtained in an experiment performed according to some embodiments of the present invention.

Figure 18:
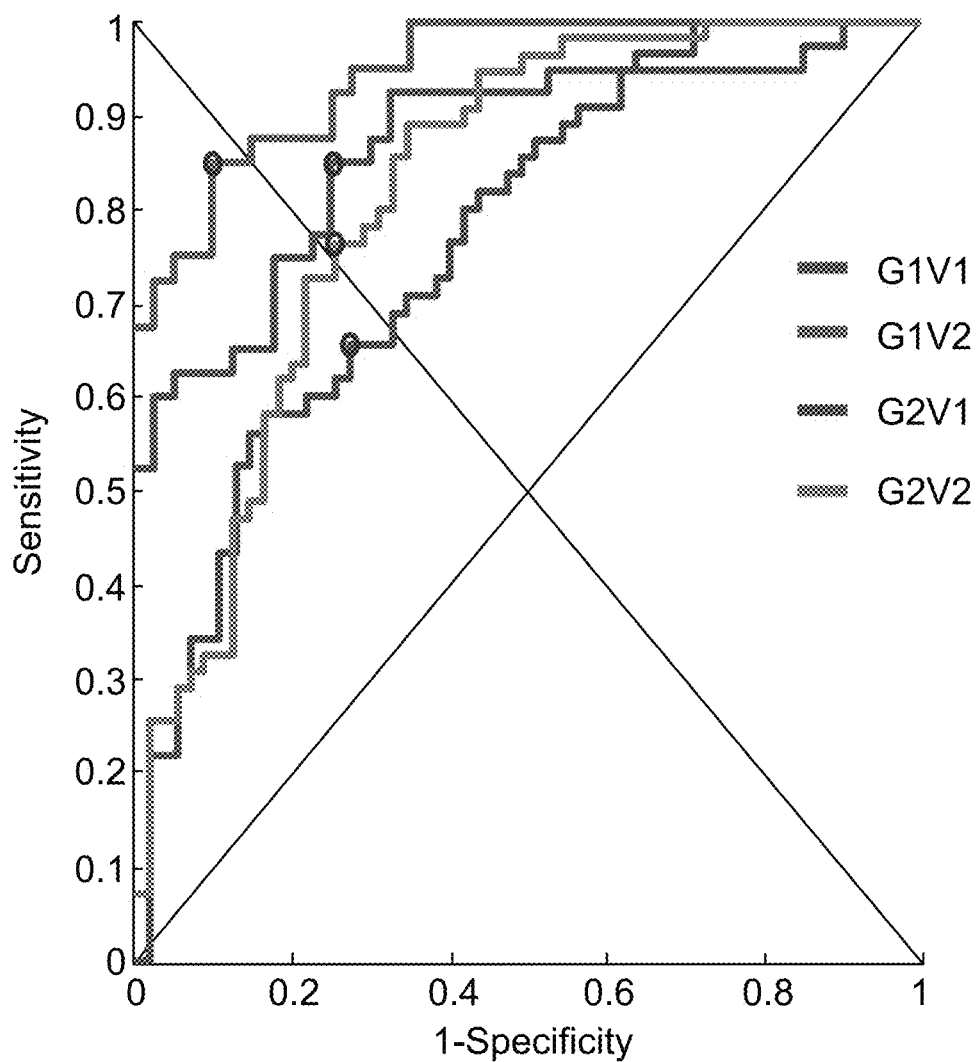

FIG. 18 shows $\theta$ band ROC curves as obtained in an experiment performed according to some embodiments of the present invention.

Figure 19:
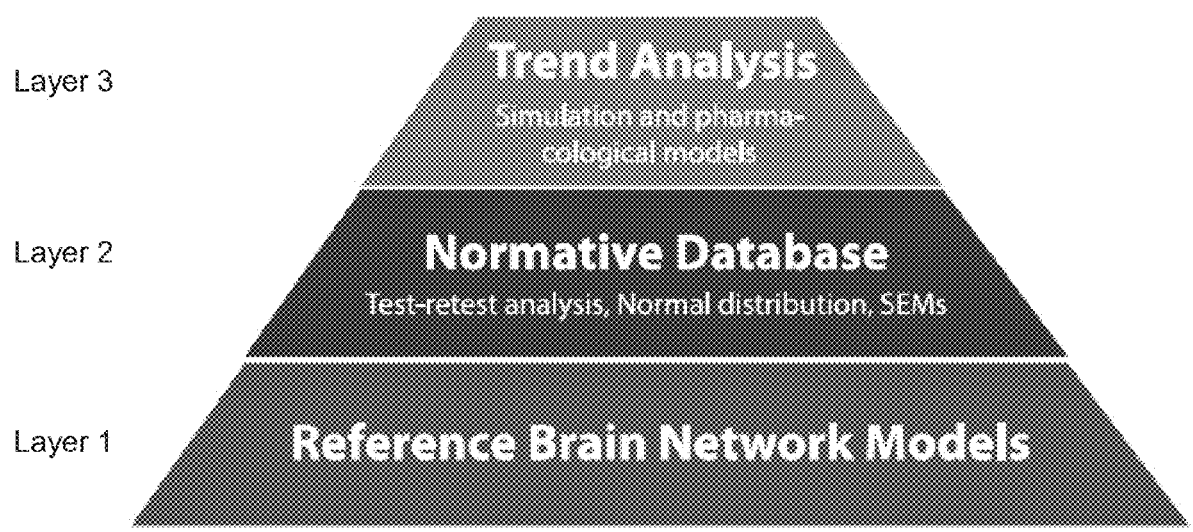

FIG. 19 is a block diagram describing a technique utilized in an exemplified study performed according to some embodiments of the present invention.

Figure 20:
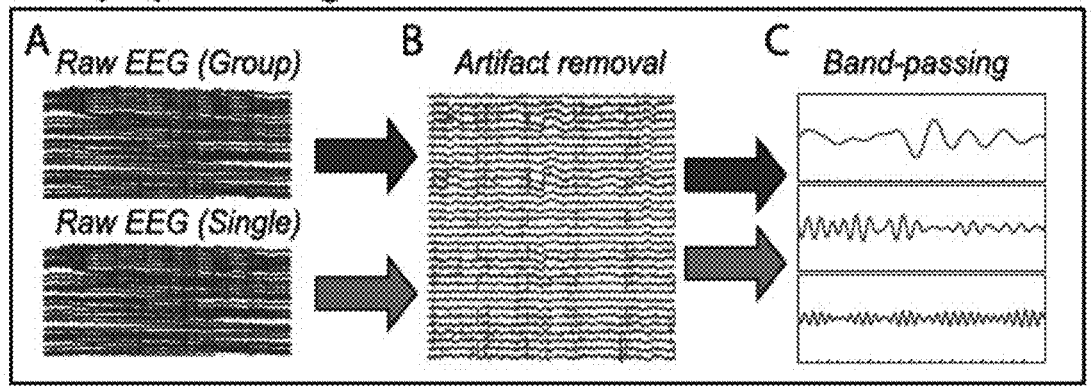
Figure 20:
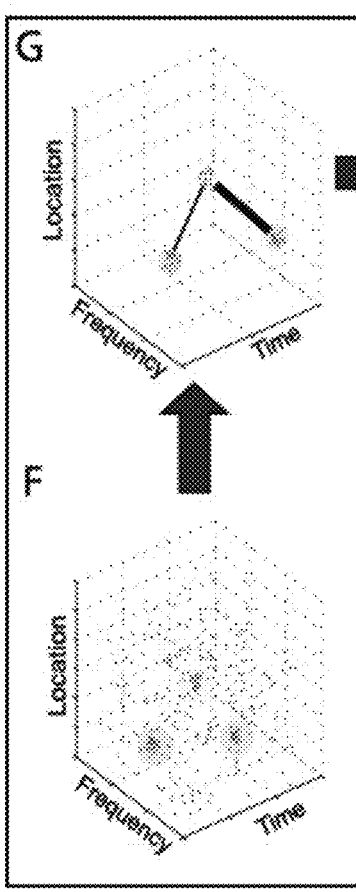
Figure 20:
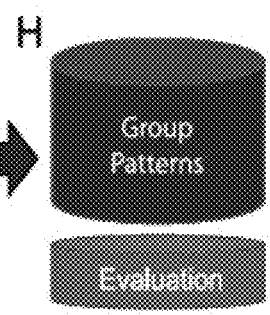
Figure 20:
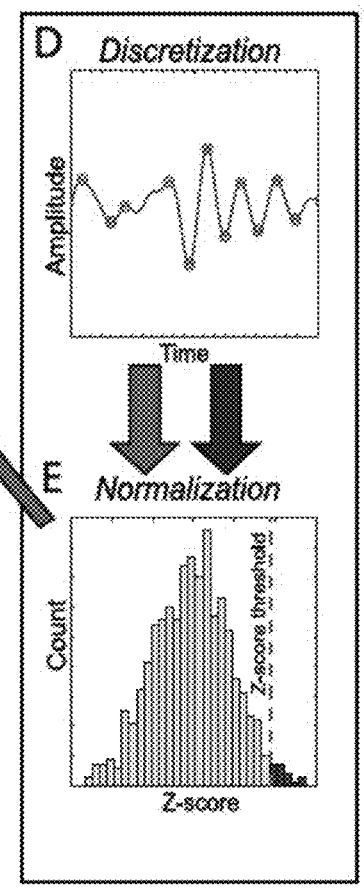

FIG. 20 is a scheme illustrating a method employed during an exemplified study performed in accordance with some embodiments of the present invention.

Figure 21:
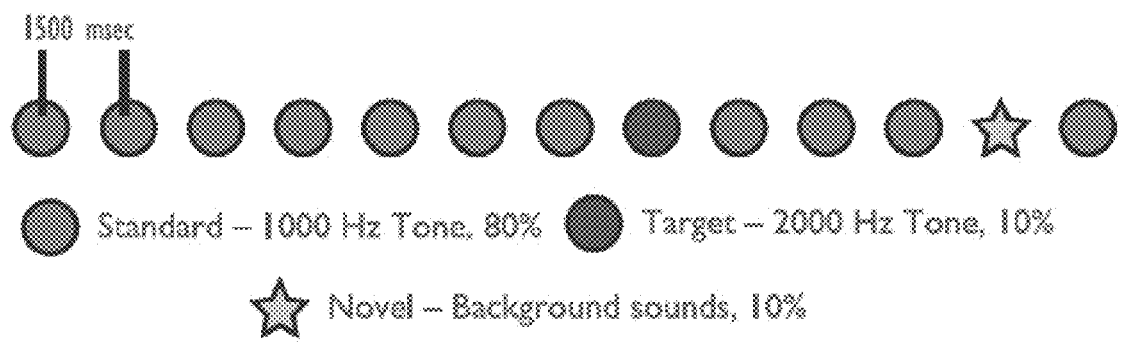

FIG. 21 is a schematic representation of an Auditory Oddball Task employed in an exemplified study performed in accordance with some embodiments of the present invention.

Figure 22:
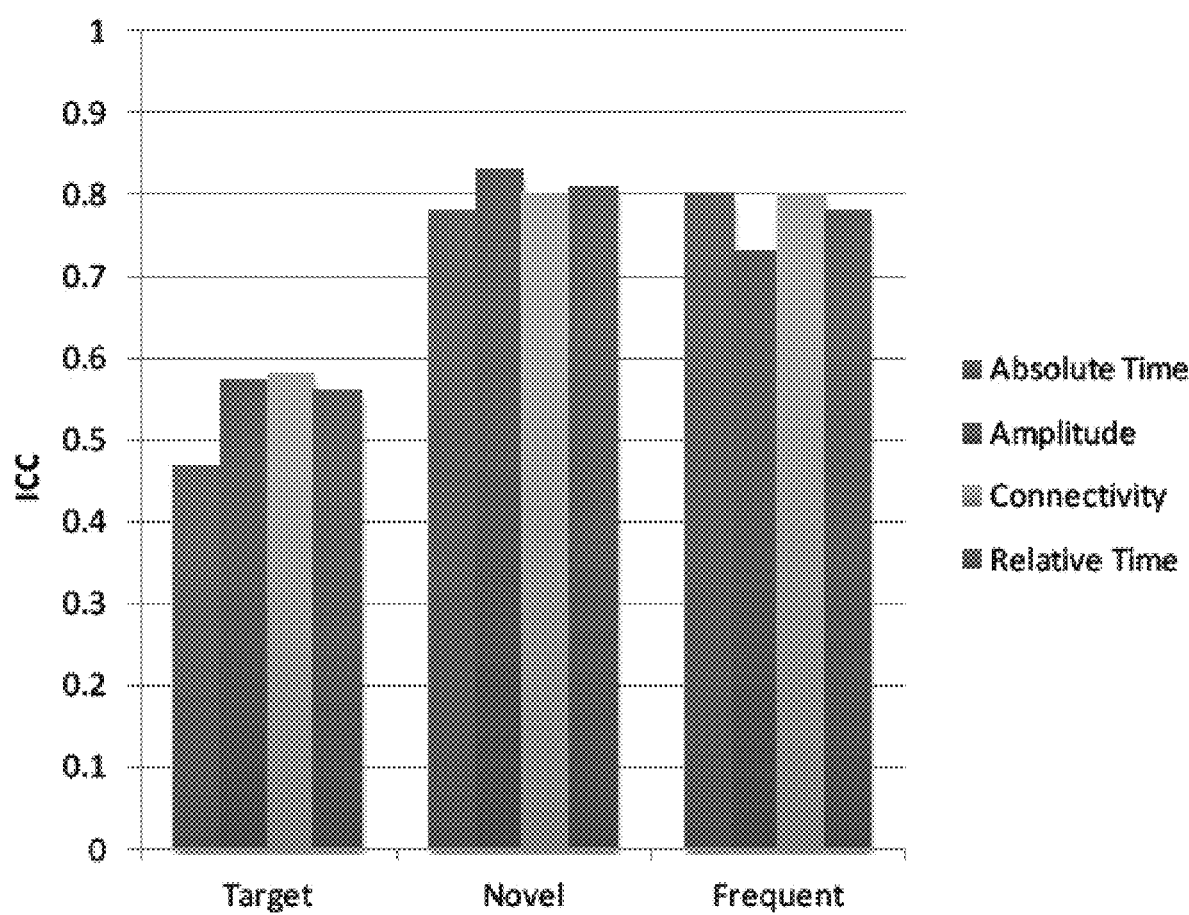

FIG. 22 shows normative database's Interclass Correlation (ICC) values for BNA scores in the two EEG-ERP sessions obtained during an exemplified study performed in accordance with some embodiments of the present invention.

Figure 23:
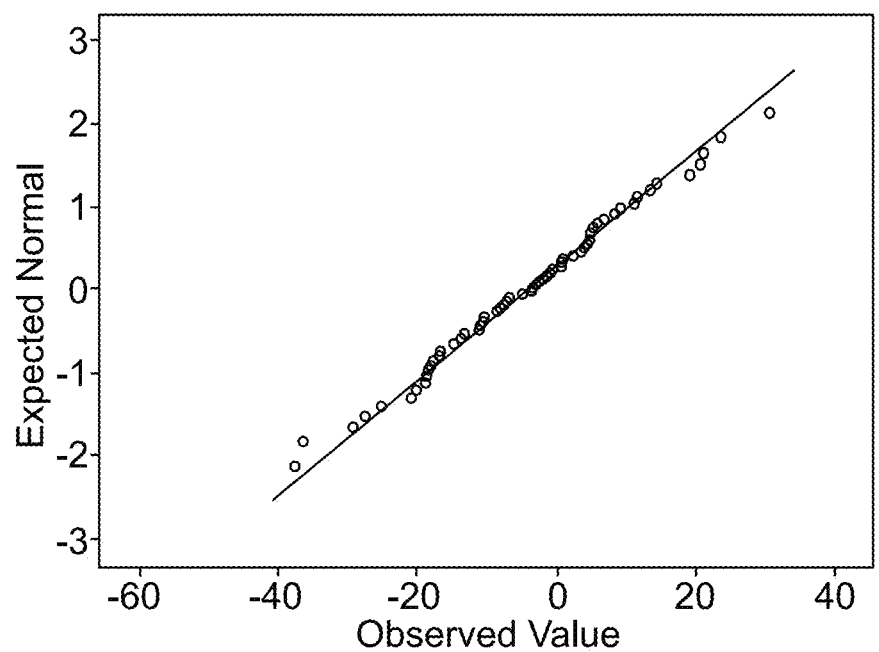

FIG. 23 shows Q-Q plot for the Connectivity $\Delta$BNA scores of a stimulus referred to as "Novel stimulus" of an Auditory Oddball Task, as obtained during an exemplified study performed in accordance with some embodiments of the present invention.

Figure 24:
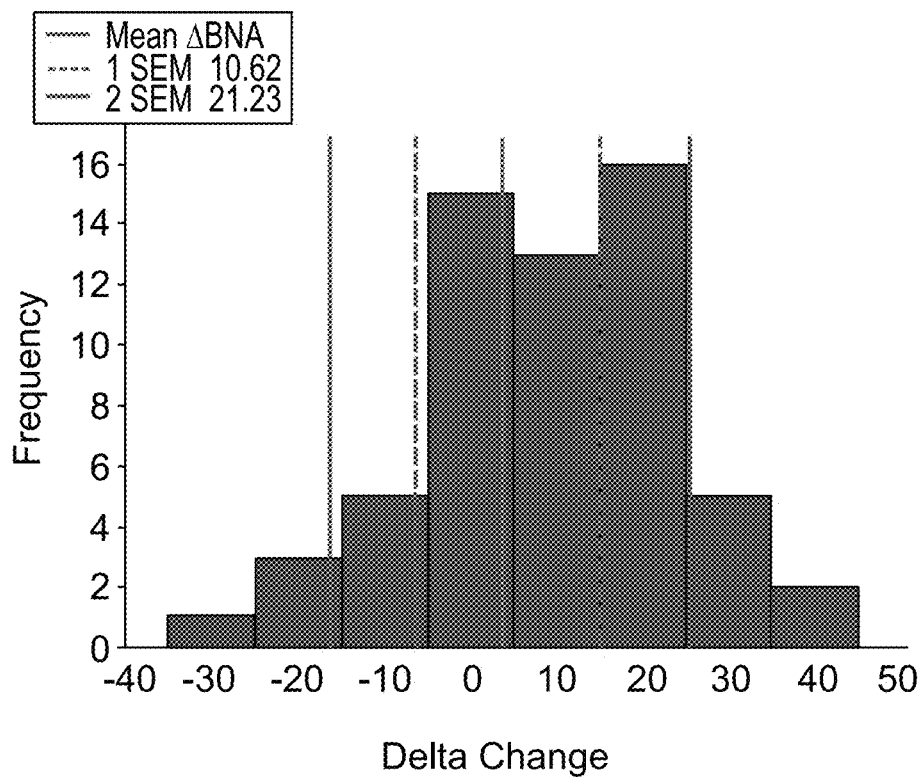

FIG. 24 shows frequency histogram for Connectivity $\Delta$BNA scores of a stimulus referred to as "Novel stimulus" of an Auditory Oddball Task, as obtained during an exemplified study performed in accordance with some embodiments of the present invention.

Figure 25:
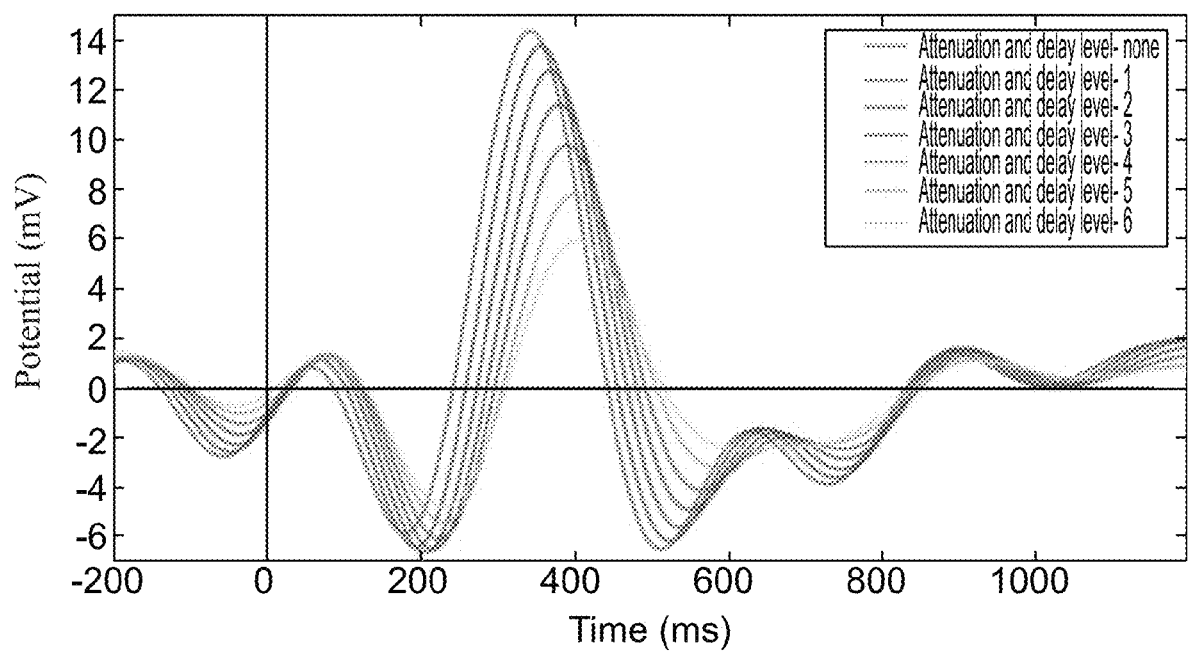

FIG. 25 shows a reconstructed ERP at Fz channel of a randomly chosen healthy subject from the normative database following a 6-step graded manipulation (combined amplitude decline and latency delay) of the P300 component in response to a stimulus referred to as "Novel stimulus" of an Auditory Oddball Task, as obtained during an exemplified study performed in accordance with some embodiments of the present invention.

Figure 26A:
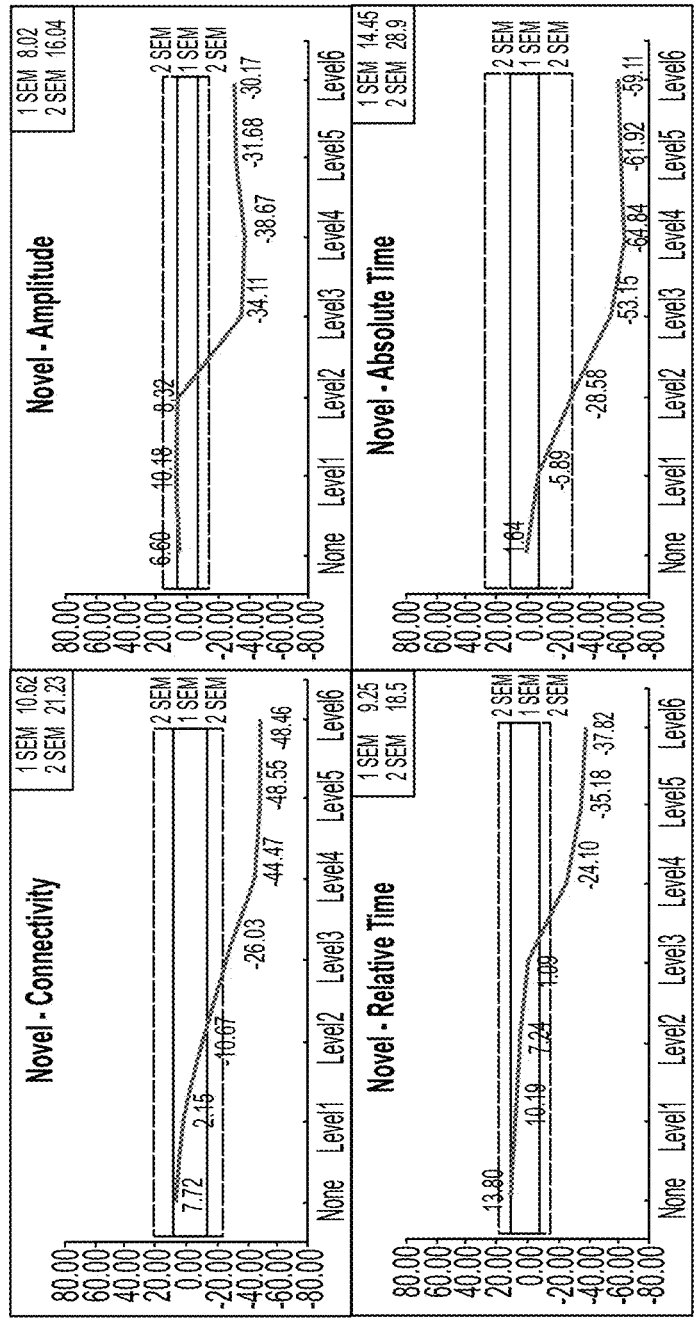
Figure 26B:
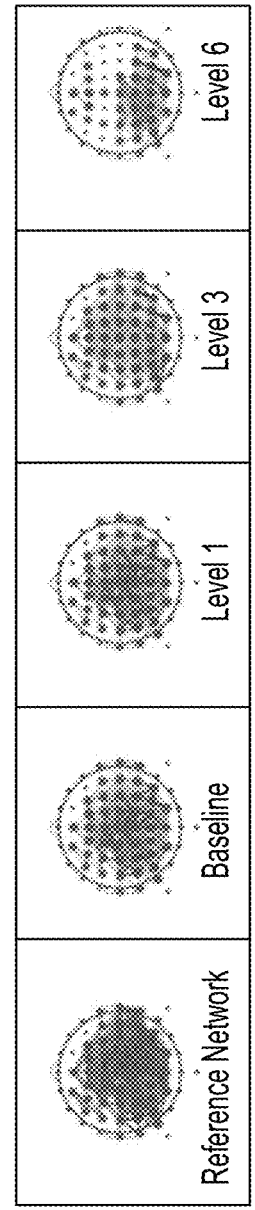

FIGS. 26A-B show simulation results obtained during an exemplified study performed in accordance with some embodiments of the present invention.

Figure 27:
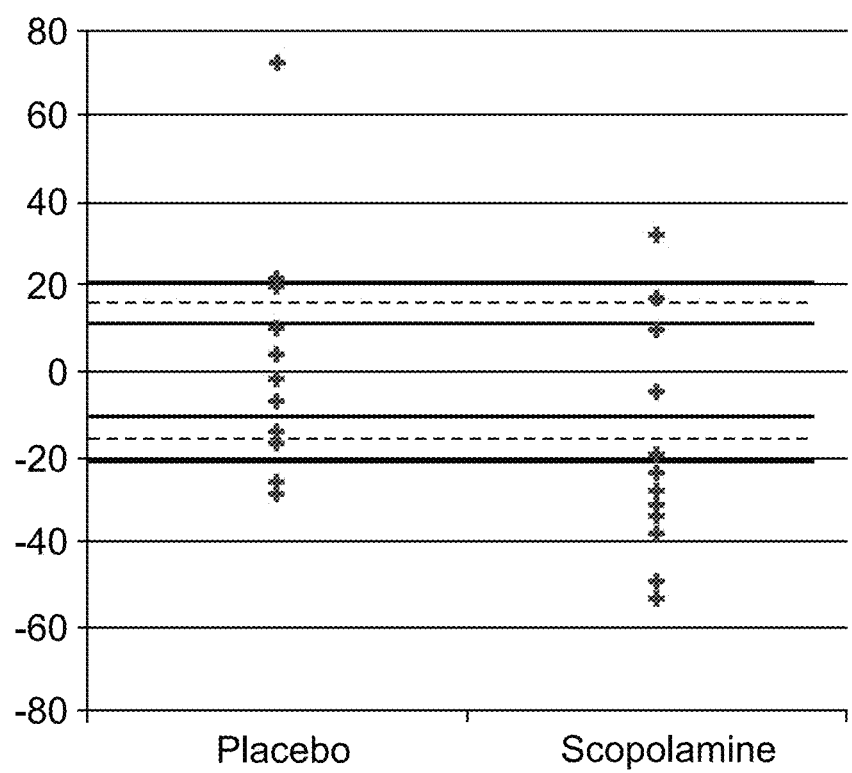

FIG. 27 shows pharmacological model results obtained during an exemplified study performed in accordance with some embodiments of the present invention.

Figure 28:
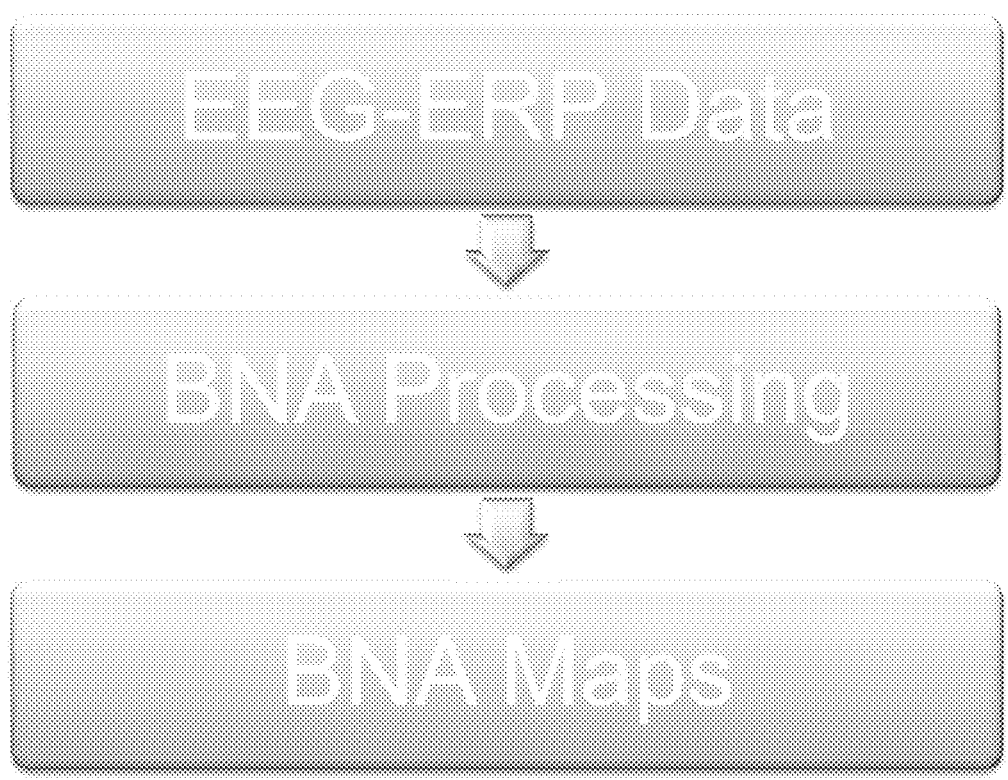

FIG. 28 is a block diagram describing a technique utilized in an exemplified experimental study performed according to some embodiments of the present invention.

Figure 29A:
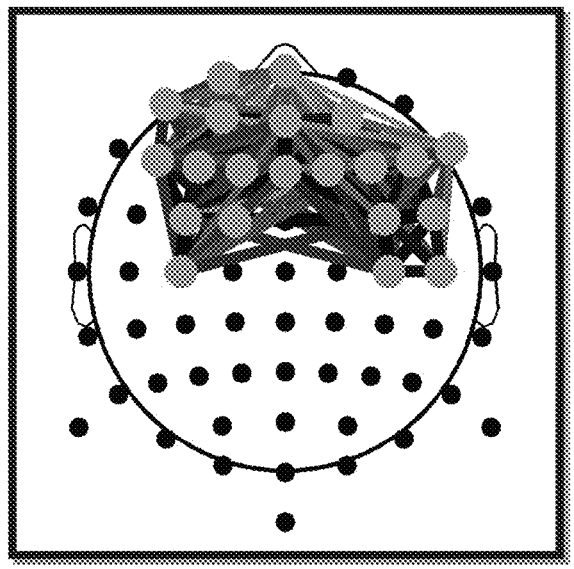
Figure 29B:
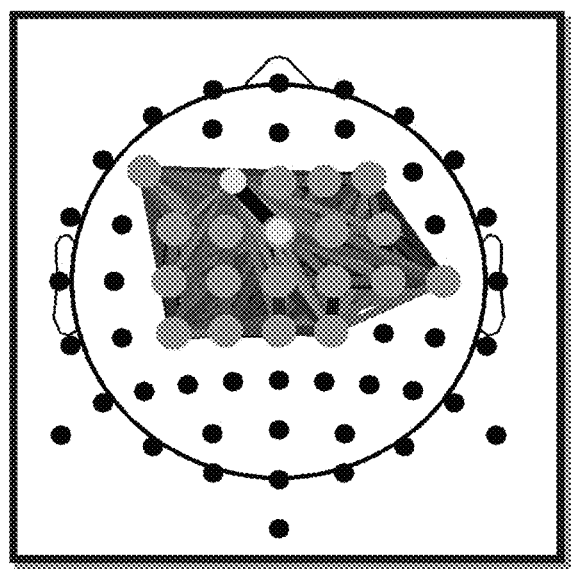
Figure 30A:
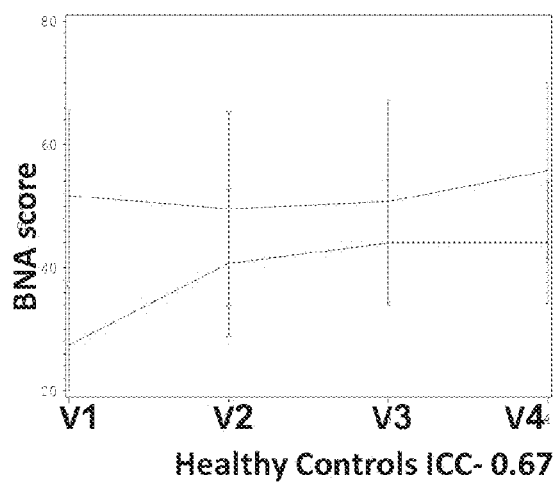
Figure 30B:
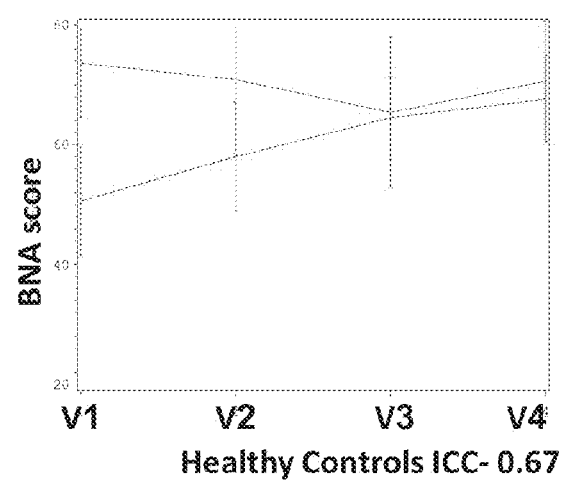
Figure 30C:
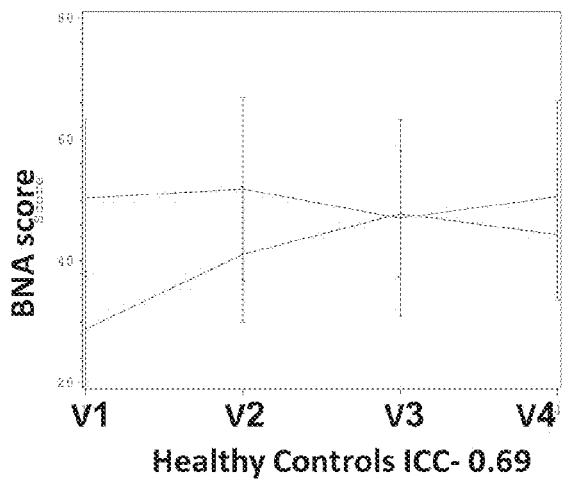
Figure 30D:
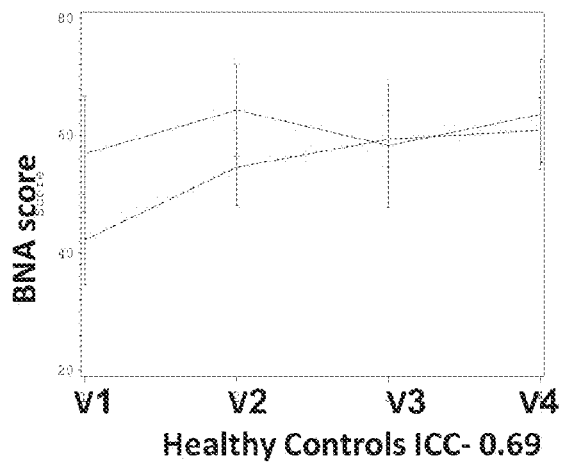
Figure 31A:
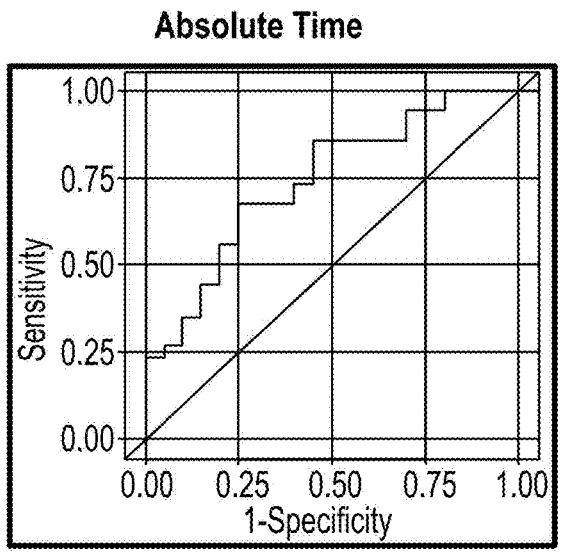
Figure 31B:
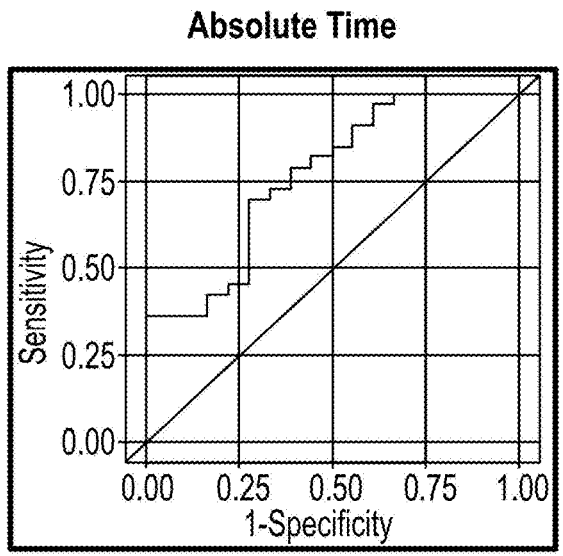
Figure 31C:
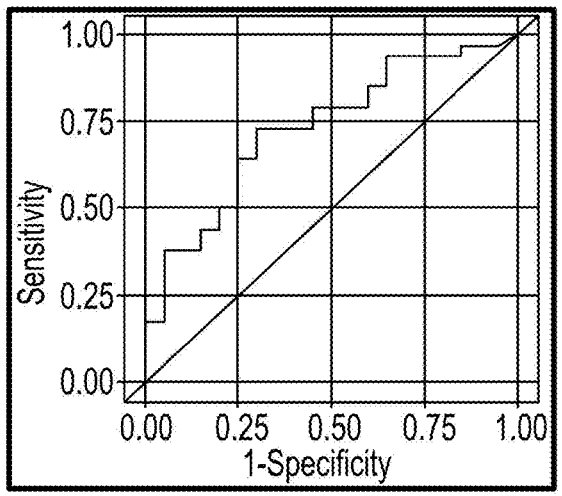
Figure 31D:
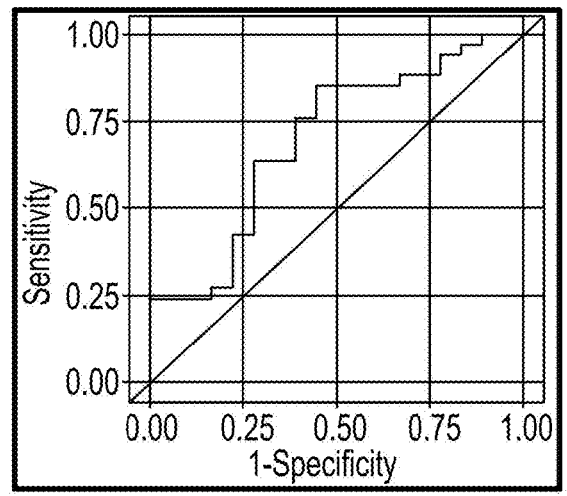

FIGS. 29A-B show selected reference BNA patterns for a Go/NoGo task (FIG. 29A), and an Auditory Oddball task (FIG. 29B), as obtained during an exemplified experimental study performed according to some embodiments of the present invention.

FIGS. 30A-D show group average BNA scores (% similarity to the reference BNA) across 4 visits for a concussed group (n=35) and a control group (n=19), as obtained during an exemplified experimental study performed according to some embodiments of the present invention.

FIGS. 31A-D show sensitivity and specificity for BNA patterns, as obtained during an exemplified experimental study performed according to some embodiments of the present invention.

Figure 32:
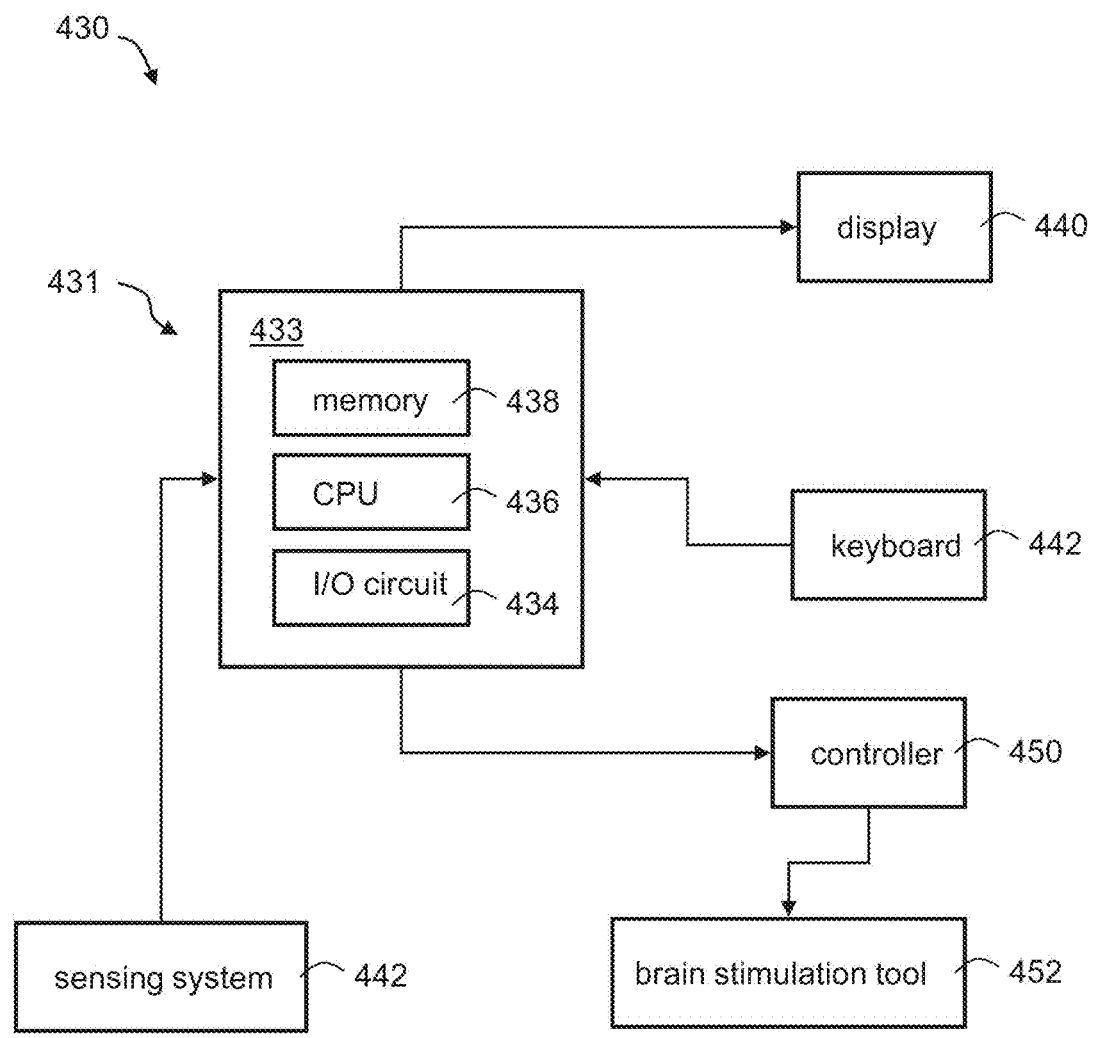

FIG. 32 is a schematic illustration of a system for analyzing neurophysiological data, according to some embodiments of the present invention.

Figure 33:
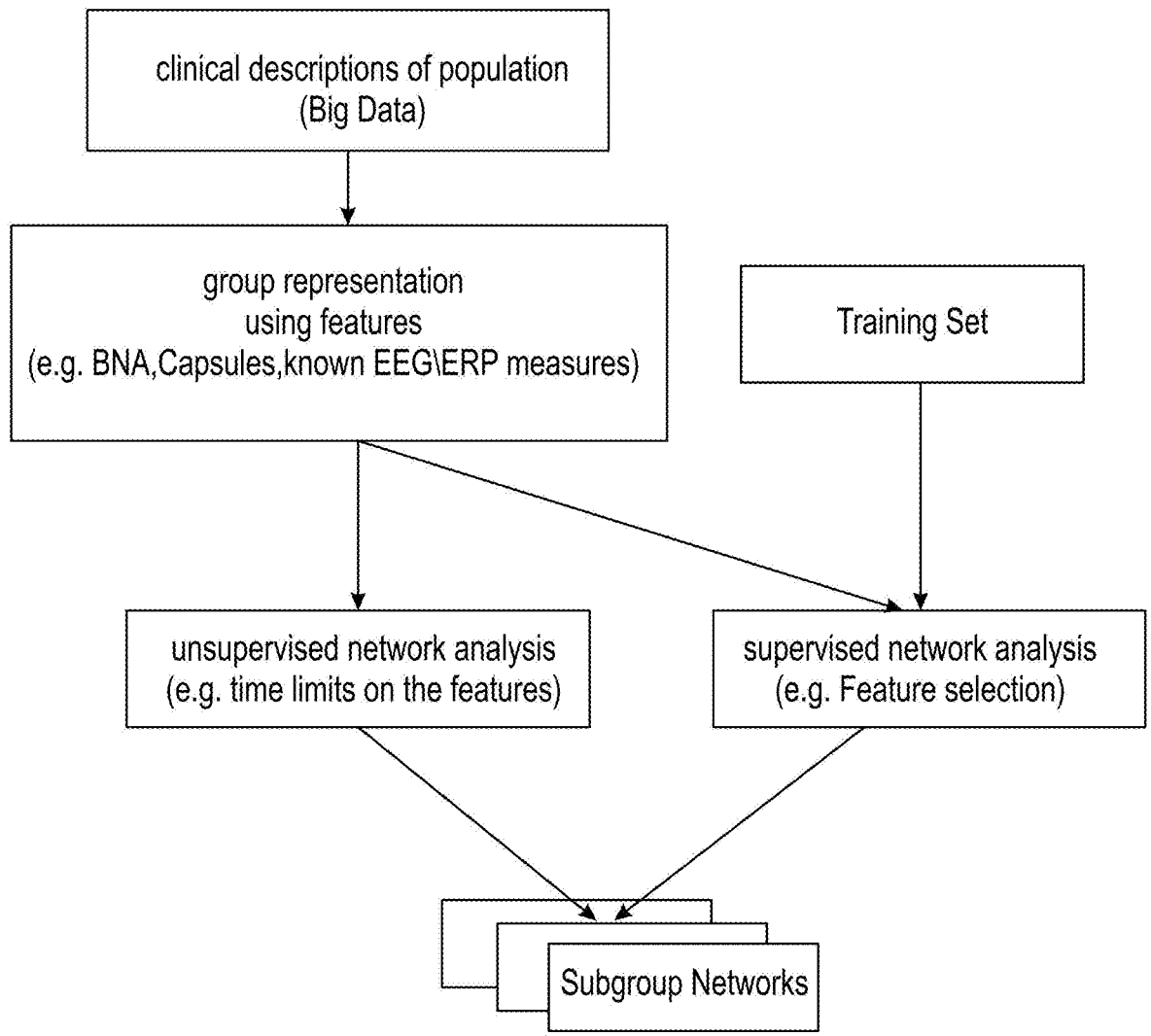

FIG. 33 is a schematic illustration of feature selection procedure suitable for some embodiments of the present invention.

Figure 34A:
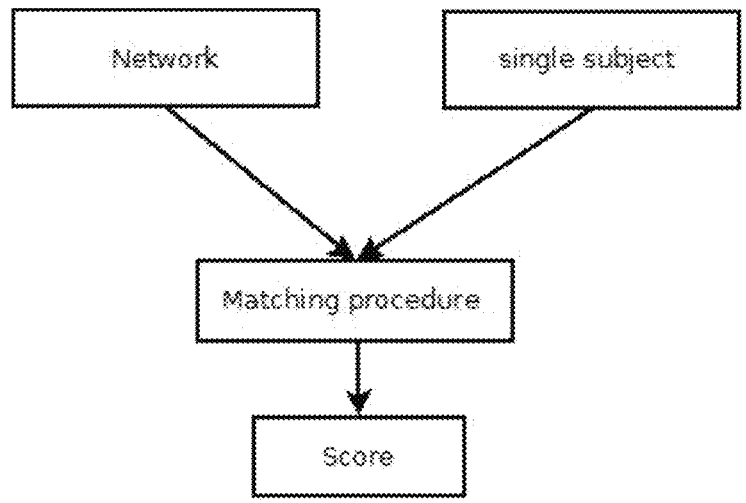
Figure 34B:
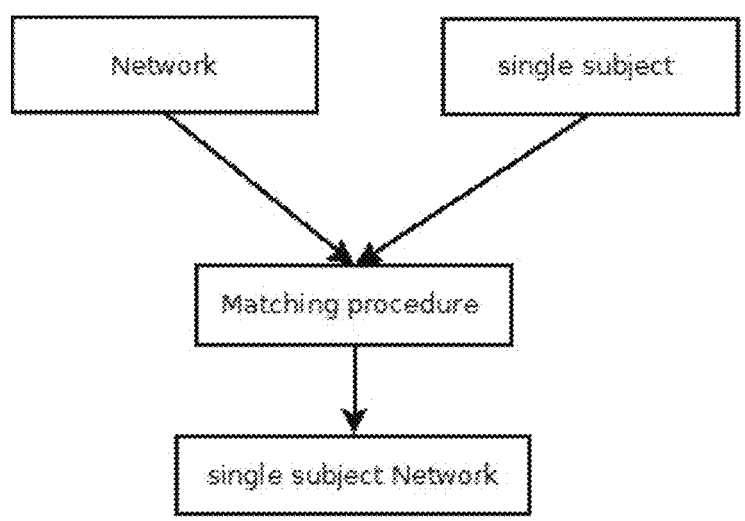
Figure 34C:
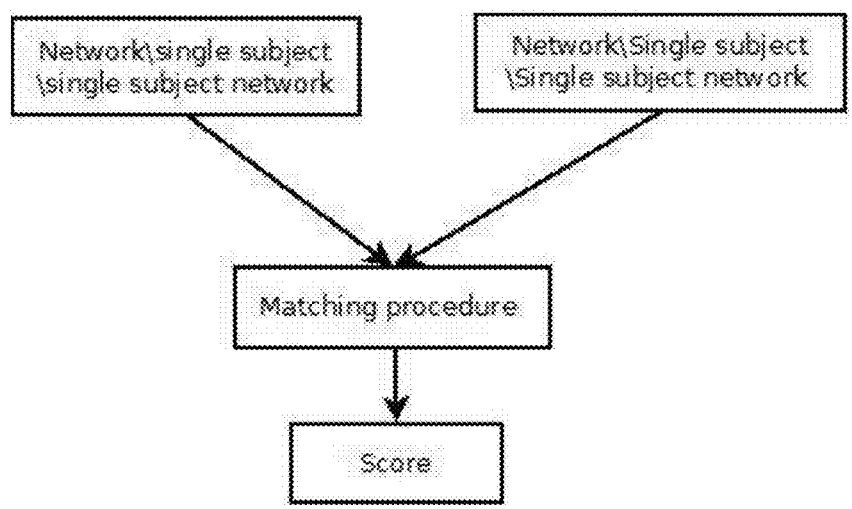

FIGS. 34A-C are schematic illustrations of comparison protocols suitable for some embodiments of the present invention.

Figure 35:
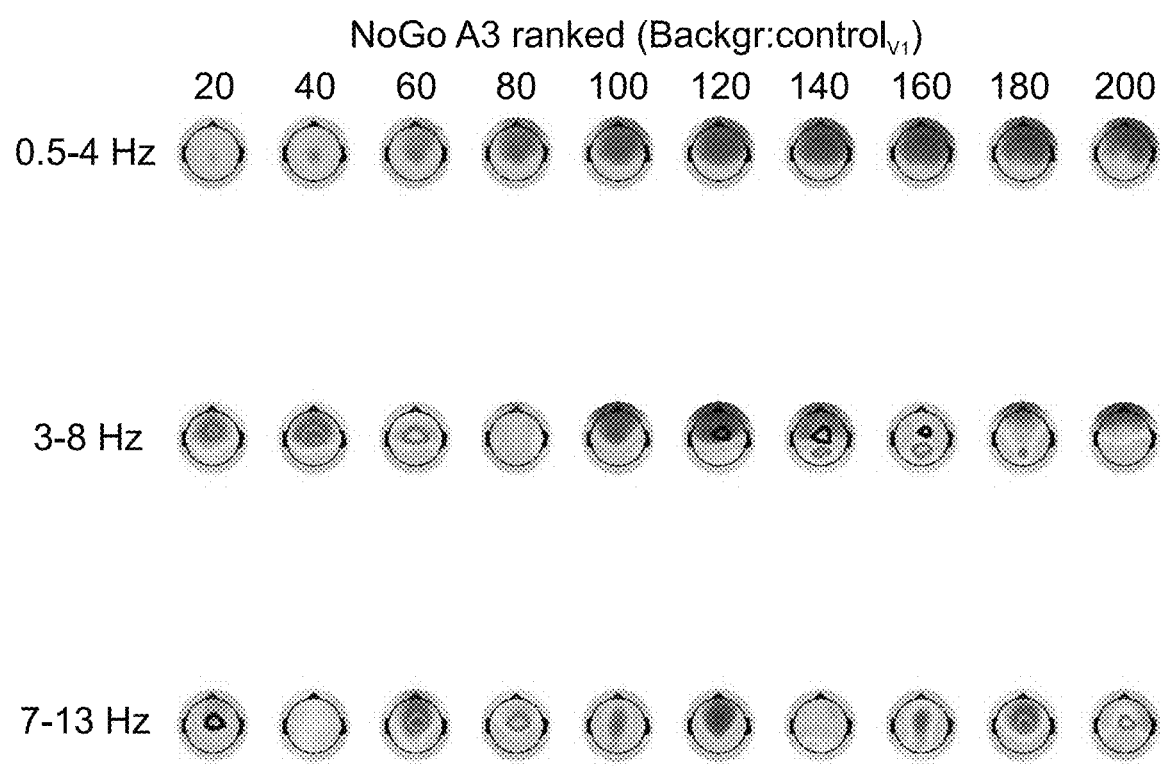

FIG. 35 shows one example of extracted spatiotemporal peaks in different frequency bands for a No-Go stimulus, used in experiments performed according to some embodiments of the present invention.

Figure 36A:
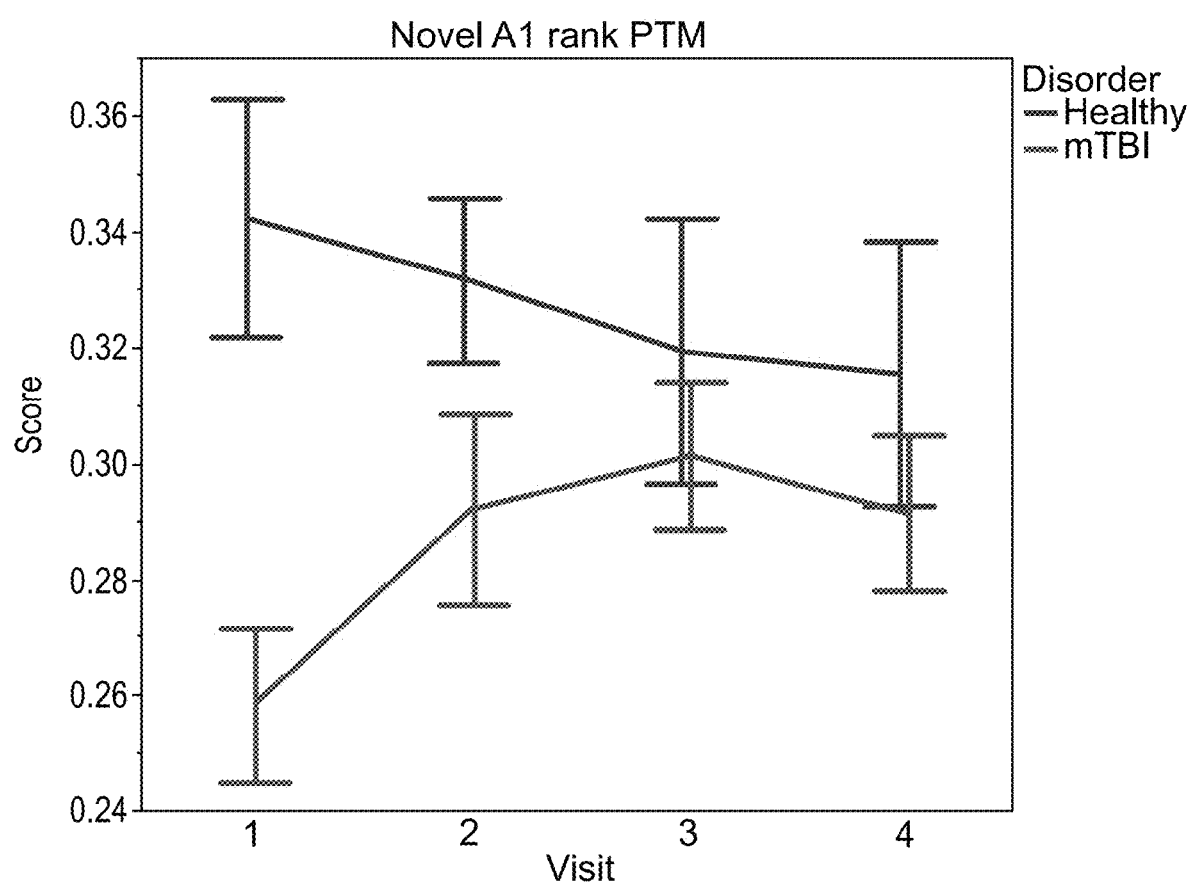
Figure 36B:
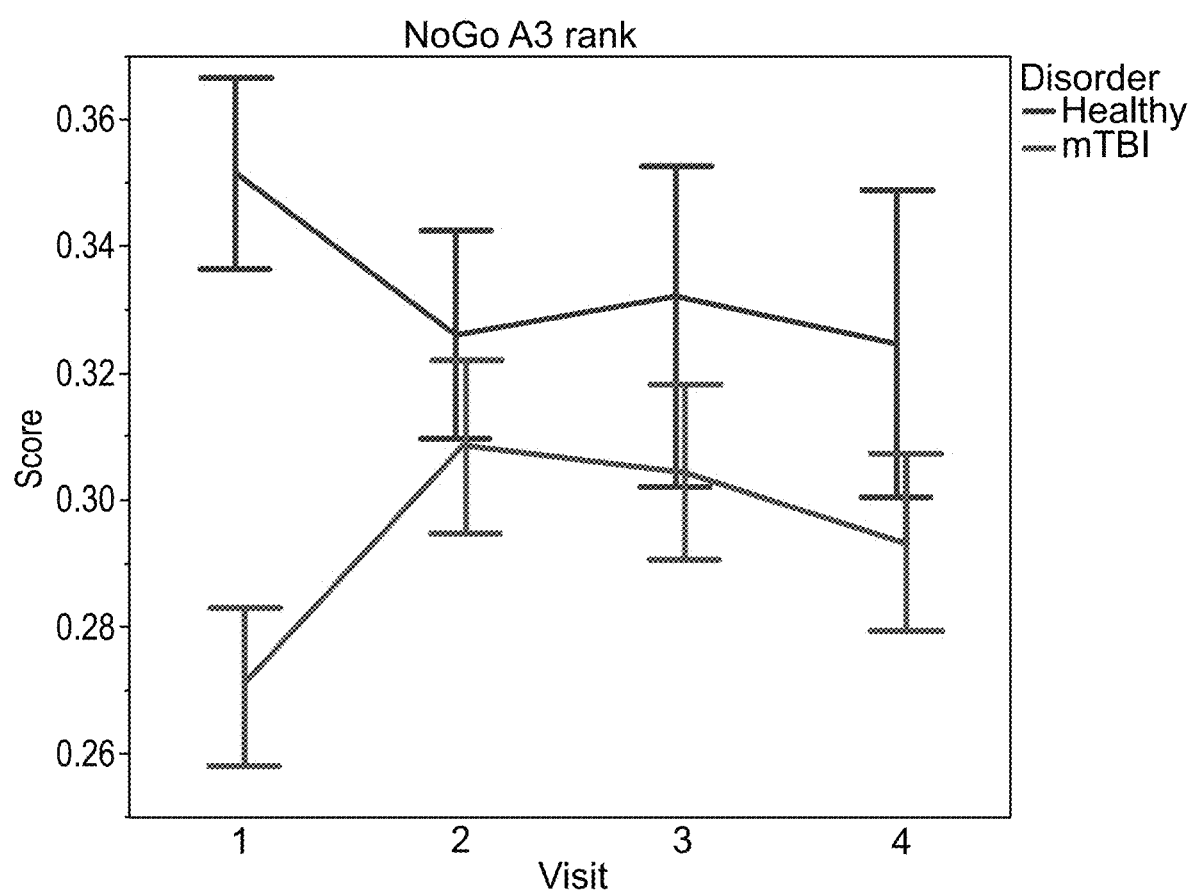
Figure 36C:
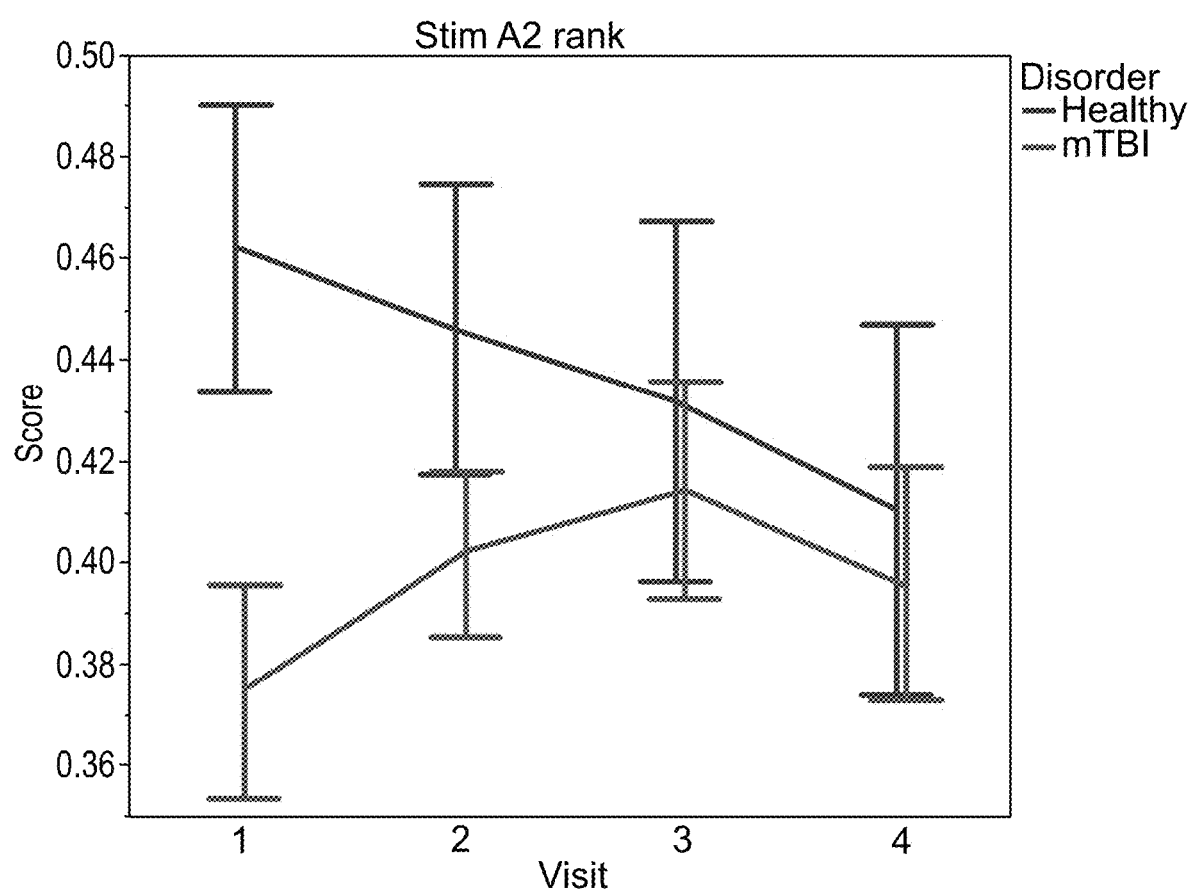

FIGS. 36A-C show results obtained during a feature selection experiment performed according to some embodiments of the present invention.

Figure 37:
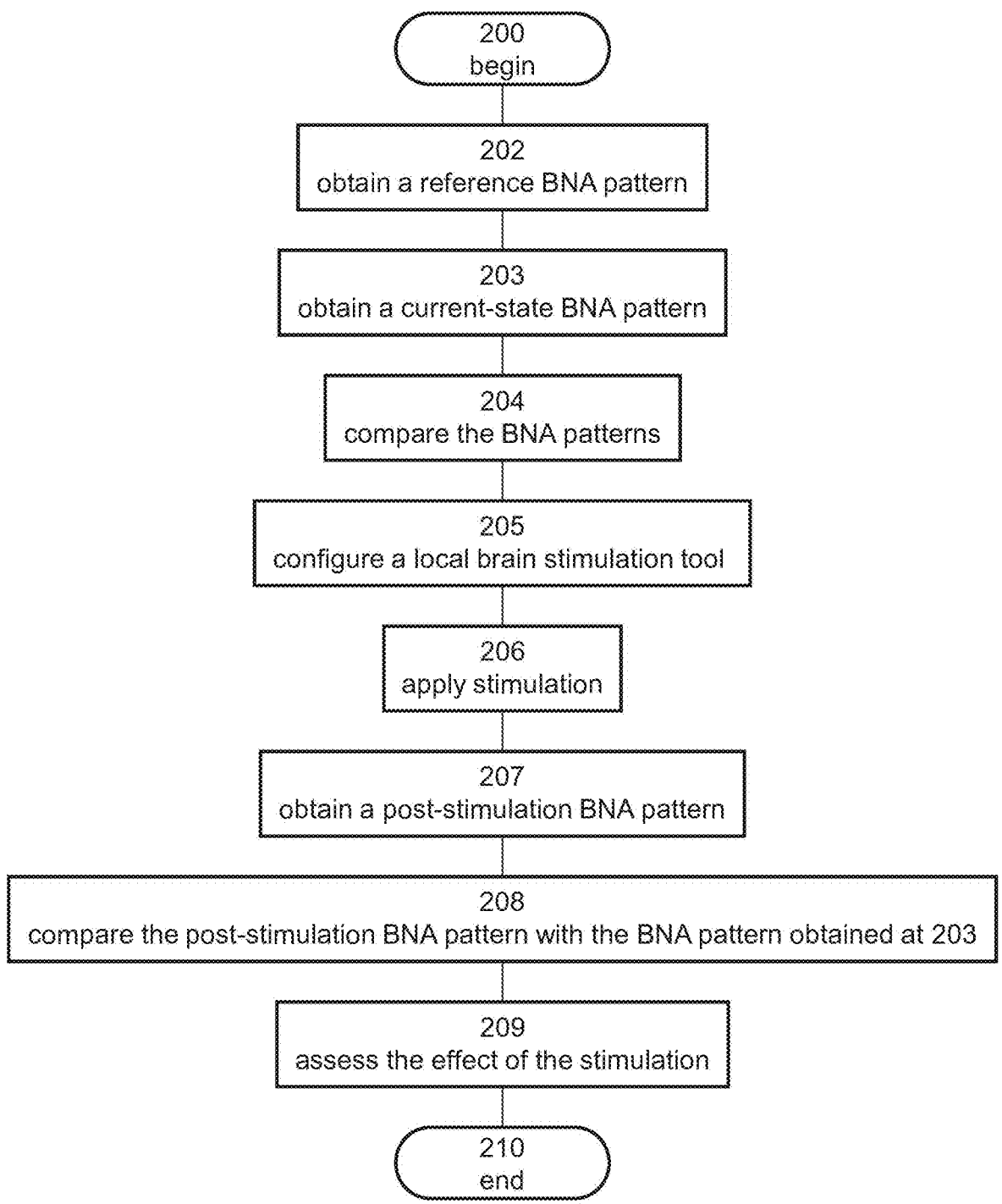

FIG. 37 is a flowchart diagram of a method suitable for configuring a local brain stimulation tool, according to various exemplary embodiments of the present invention.

DESCRIPTION OF SPECIFIC EMBODIMENTS OF THE INVENTION

The present invention, in some embodiments thereof, relates to neurophysiology and, more particularly, but not exclusively, to method and system for configuring a brain stimulation tool.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Embodiments of the present invention are directed to a technique for configuring a brain stimulation tool. Optionally, but not necessarily, the brain stimulation tool is thereafter used for stimulating the brain of an individual, for example, for the purpose of treating a brain disorder or condition.

The brain stimulation tool is configured based on information pertaining to, e.g., behavior, condition, brain function, and other characteristics of the subject. In various exemplary embodiments of the invention the information is expressed as one or more data objects. In some embodiments of the present invention the data object is a brain network activity (BNA) pattern, in some embodiments the data object is a spatiotemporal activity region in the brain, and in some embodiments the data object is a BNA pattern corresponding to spatiotemporal activity regions.

It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

At least part of the operations can be implemented by a data processing system, e.g., a dedicated circuitry or a general purpose computer, configured for receiving the data and executing the operations described below.

Computer programs implementing the method of the present embodiments can commonly be distributed to users on a distribution medium such as, but not limited to, a floppy disk, a CD-ROM, a flash memory device and a portable hard drive. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The method of the present embodiments can be embodied in many forms. For example, it can be embodied in on a tangible medium such as a computer for performing the method operations. It can be embodied on a computer readable medium, comprising computer readable instructions for carrying out the method operations. In can also be embodied in electronic device having digital computer capabilities arranged to run the computer program on the tangible medium or execute the instruction on a computer readable medium.

Reference is now made to FIG. 37 which is a flowchart diagram of a method suitable for configuring a local brain stimulation tool, according to various exemplary embodiments of the present invention.

Optionally, the method is suitable for treating a subject, but this is not necessary, since the method can be executed only for configuring the stimulation tool, without treating the subject.

The method begins at 200 and continues to 202 at which a reference brain network activity (BNA) pattern, is obtained, and to 203 at which a BNA pattern describing a neurophysiological state of the subject is obtained. The BNA pattern obtained at 203 is referred to herein as a "current-state BNA pattern" to indicate that it describes the current state of the subject under analysis. The BNA patterns can be constructed by the method, or they can be provided from an external source, such as, but not limited to, a local or remote data processor. Also contemplated are embodiments in which one of the BNA patterns (e.g., the current-state BNA pattern) is constructed by the method, and the other BNA pattern (e.g., the reference BNA pattern) is received from an external source. For example, the reference BNA pattern can be an entry of a database of reference BNA patterns, as further detailed hereinbelow.

Figure 2:
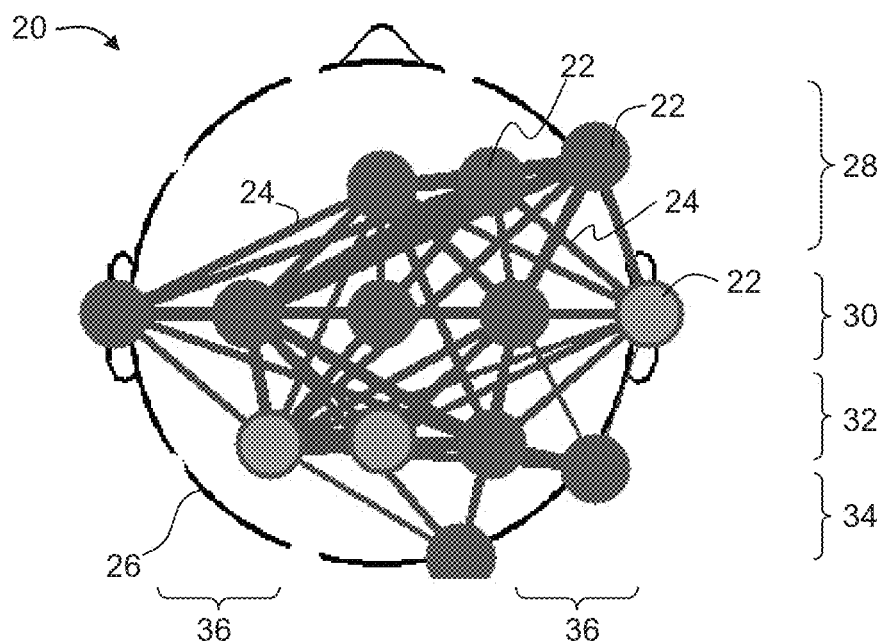

The concept of BNA pattern can be better understood with reference to FIG. 2 which is a representative example of a BNA pattern 20 which may be received as input or extracted from neurophysiological data. BNA pattern 20 has a plurality of nodes 22, each representing a particular brain wave frequency band (optionally two or more particular frequency bands) at a particular brain or skull location, and optionally within a particular time-window or latency range, and further optionally with a particular range of amplitudes.

Some of nodes 22 are connected by edges 24 each can represent, for example, the causal relation between the nodes at the ends of the respective edge. Thus, the BNA pattern according to some embodiments of the present invention is represented as a graph having nodes and edges. In various exemplary embodiments of the invention the BNA pattern includes plurality of discrete nodes, wherein information pertaining to features of the data (frequency band(s), location, time-window, amplitude range) is represented only by the nodes and information pertaining to relations among the features is represented only by the edges.

FIG. 2 illustrates BNA pattern 20 within a template 26 of a scalp, allowing relating the location of the nodes to the various lobes of the brain (frontal 28, central 30, parietal 32, occipital 34 and temporal 36). The nodes in the BNA pattern can be labeled by their various characteristics. A color coding or shape coding visualization technique can also be employed, if desired. For example, nodes corresponding to a particular frequency band can be displayed using one color or shape and nodes corresponding to another frequency band can be displayed using another color or shape. In the representative example of FIG. 2, two colors are presented. Red nodes correspond to Delta waves and green nodes correspond to Theta waves.

In some embodiments of the present invention the nodes of the BNA patterns are capsule objects (hereinafter "capsules"), each representing at least a spatiotemporal activity region in the brain. The spatiotemporal activity region defines a spatiotemporal neighborhood of a respective feature of the neurophysiological data from which the BNA is constructed. In some embodiments of the present invention the neighborhood is a spectral-spatiotemporal neighborhood, these embodiments are detailed hereinafter.

The neighborhood can be defined as a spatial region (two- or three-dimensional) in which a data extremum (peak, troughs, etc.) is located and/or a time-interval during which the extremum occurs. Preferably each capsule defines both a spatial region and time-interval. The advantage of such capsules is that they provide information regarding the spreading structure of the neurophysiological data over time and/or space. The size of the neighborhood (in terms of the respective dimension) can be determined based on the property of the extremum. For example, in some embodiments, the size of the neighborhood equals the full width at half maximum (FWHM) of the extremum. Other definitions of the neighborhood are also contemplated. BNA pattern 20 can also be a connected capsule BNA pattern, in which case the nodes are connected by edges, wherein the nodes represent capsules and the edges represent inter-capsule relations among capsules, as further detailed hereinbelow.

BNA pattern 20 can describe brain activity of a single subject or a group or sub-group of subjects. A BNA pattern which describes the brain activity of a single subject is referred to herein as a subject-specific BNA pattern, and BNA pattern which describes the brain activity of a group or sub-group of subjects is referred to herein as a group BNA pattern.

When the subject under analysis has a brain disorder or condition, the reference BNA pattern obtained at 202 preferably corresponds to a subject or group of subject who have been diagnosed as not having this brain disorder. For example, the reference BNA pattern can be annotated as "normal." A normal BNA pattern corresponds to a subject or group of subject who have been diagnosed as having normal brain function.

The reference BNA pattern can also include a BNA pattern associated with annotation information pertaining to a specific brain related disorder or condition of a group of subjects in relation to a treatment applied to the subjects in the group. Such baseline BNA pattern can also be annotated with the characteristics of the treatment, including dosage, duration, and elapsed time following the treatment. A comparison of the current-state BNA pattern to such type of reference BNA patterns (see 204 below), can provide information regarding the responsiveness of the subject to treatment and/or the efficiency of the treatment for that particular subject. Such comparison can optionally and preferably be used for extracting prognostic information in connection to the specific treatment. A BNA pattern that is complementary to such a reference BNA pattern is a BNA pattern that is annotated as corresponding to an untreated brain related disorder.

The reference BNA pattern can, in some embodiments of the present invention, be a single subject BNA pattern, which describes a previous neurophysiological state of the same subject, and which can therefore serve as a baseline against which the current-state BNA pattern can compared (see 204, below). The advantage of such baseline is that variability among data obtained within the subject is typically smaller than the variability between subjects. Thus, according to some embodiments of the present invention the BNA pattern of the subject is compared to a BNA pattern that corresponds to the same subject.

The method continues to 204 at which the BNA patterns are compared. The comparison is optionally and preferably node-wise, wherein the method determines, for each node in the current-state BNA pattern whether it exists in the reference BNA pattern, and vice versa. The method can also compare the nodes themselves in terms of the features they represent. For example, when the method determines that both BNA patterns have a node that represents some particular location, the method can determine whether those nodes are associated with the same frequency band and to what extent (e.g., whether the amplitudes of the peak of the brain waves at the particular frequency band are similar).

In some embodiments of the present invention the BNA patterns are weighted BNA patterns. In these embodiments, the method optionally and preferably uses the weights either for the comparison or for the comparison or for selecting the reference BNA pattern from the database. When the weights are used for the comparison, the method can compute the similarity between nodes based on the weights. Techniques for comparing BNA patterns are described hereinunder.

The method optionally and preferably continues to 205 at which the local brain stimulation tool is configured to apply local brain stimulation at a frequency selected based on comparison.

As used herein "local brain stimulation" refers to any brain stimulation protocol, which requires knowledge of coordinates relative to the brain, cortex or skull in order to apply the stimulation.

As used herein "local brain stimulation tool" refers to any brain stimulation system that requires input regarding the coordinates relative to the brain, cortex or skull.

As used herein "coordinates relative to the brain, cortex or skull" refer to coordinates that define one or more points or regions within the brain, cortex or skull, where each point or region (or the collection of all points or regions, when the coordinates define more than one point or region) form portion of the brain, cortex or skull.

The terms "local brain stimulation" and "local brain stimulation tool" exclude procedures and systems which do not require any particular input regarding the coordinates over the brain, cortex or skull at which the stimulation is applied.

The term "coordinates relative to the brain, cortex or skull" exclude coordinates that define any region or collection of regions that encompasses the entire brain, the entire cortex or the entire skull.

It is to be understood that while the local brain stimulation tool is configured to apply local brain stimulation at a particular frequency, the duration of the stimulation applied by the tool is not necessarily longer than the period that corresponds to that particular frequency. Specifically, denoting the stimulation frequency to which the tool is configured by f, the duration of the stimulation can be less than 1/f, or equal to 1/for larger than 1/f.

The local brain stimulation can be a single focal stimulation or a multi-focal stimulation. Single focal stimulation is a stimulation for which the coordinates define a single stimulation region or point, and optionally also a single reference region or point. Multi-focal stimulation is a stimulation for which the coordinates define a multiplicity of non-overlapping stimulation regions or points, and optionally also one or more reference region or point.

Optionally, the local brain stimulation tool is also configured to apply local brain stimulation at a location selected based on comparison. In some embodiments of the present invention the location is corrected using a technique selected from the group consisting of a source localization procedure, Cortical Potential Imaging (CPI), and Cortical Source Density (CSD). These techniques are described hereinunder.

The selected frequency correlates with the frequency band associated with one or more nodes of the BNA patterns, preferably the reference BNA pattern. Thus, for example, suppose that a particular node n in the reference BNA pattern is associated with a particular brain location x, say a particular location within the occipital lobe of the brain, and is also associated with a particular frequency band f, say the characteristic frequency band of a Delta waves. Suppose further that the current-state BNA pattern also has that particular node n (namely a node that is associated with the same location x) except that in the current-state BNA pattern the frequency f is missing or suppressed in the node n. In this case, the tool is configured to apply frequency f. Suppose alternatively that node n (associated with location x and frequency f) exists in the reference BNA pattern but is missing in the current-state BNA pattern. In this case also, the tool is configured to apply frequency f.

In embodiments in which the tool is also configured to apply the stimulation at a specific location, the selected location correlates with the location associated with the same node or nodes. Thus, in the above examples, the tool can be configured to apply the stimulation at the location x and at the frequency f.

For those nodes in the two BNA patterns that are alike both with respect to the location and with respect to the frequency, operation 205 is preferably skipped.

Aside from the location and frequency, the nodes of the BNA pattern can also be associated with a latency parameter, as further detailed below. In these embodiments, the local brain stimulation tool is optionally configured to apply local brain stimulation at a time or synchronization selected based on the comparison, wherein the time of stimulation refers to the elapsed time from a reference time point to a time point at which the stimulation begin. When the local brain stimulation tool is configured to apply local brain stimulation at a particular time or synchronization, the method can executed 205 (configuring the tool to a particular frequency) or not executed 205, as desired.

The reference time point can be a time point at which the local brain stimulation was applied at a different location. In these embodiments, the stimulation aids in improving the synchronization among different brain regions. For example, consider a situation in which a pair of nodes $n_1$ and $n_2$ in the reference BNA pattern is respectively associated with a pair of particular brain locations $x_1$ and $x_2$, and a pair of latency parameters $t_1$ and $t_2$. Suppose that the nodes $n_1$ and $n_2$ are related to each other in the sense that the difference $\Delta t_R = t_1 - t_2$ satisfies some criteria as further detailed hereinbelow (for example, suppose that $n_1$ and $n_2$ are connected by an edge over the BNA tern). Suppose further that the current-state BNA pattern also has that particular nodes $n_1$ and $n_2$ (namely a pair of nodes that is associated with the same pair of locations $x_1$ and $x_2$) except that in the current-state BNA pattern the latency difference between these nodes is different from $\Delta t_R$. In this case, the tool is configured to apply stimulation to locations $x_1$ and $x_2$ at different times such that the time difference between the stimulation applied to $x_1$ and the stimulation applied to $x_2$ approximately equals $\Delta t_R$. Typically, but not necessarily, the stimulation is applied so as to shorten the latency difference between the respective nodes in the current-state BNA pattern.

The frequency at which the stimulation at locations $x_1$ and $x_2$ is applied is optionally and preferably the same, and can be selected to be equal to the frequency associated with nodes $n_1$ and $n_2$ of the reference BNA pattern. Alternatively, different frequencies can be applied to locations $x_1$ and $x_2$. These embodiments are particularly useful when nodes n1 and n2 of the reference BNA pattern are associated with different frequencies.

The reference time point can be a time point at which the subject was presented with a sensible (e.g., visual or audio) stimulus, for example, during a cognitive test wherein the subject is asked to perform or conceptualize a task in response to the sensible stimulus.

For example, consider a situation in which a node n in the reference BNA pattern is associated with a particular brain location $x_1$, and a latency parameter $t_R$. Suppose further that the current-state BNA pattern also has that particular node n (namely a node that is associated with the same location x) except that in the current-state BNA pattern the latency parameter is different from $t_R$. In this case, the stimulation can be executed during a cognitive test, wherein the time difference between the time point at which the stimulation is applied and the time point at which the subject was presented with the sensible stimulus approximately equals $t_R$. Typically, but not necessarily, the stimulation is applied so as to shorten the latency parameter in the current-state BNA pattern. The frequency at which the stimulation at location x is applied is optionally and preferably selected to be equal to the frequency associated with node n of the reference BNA pattern.

The present embodiments contemplate the configuration of tools that apply many types of local brain stimulations, including tools that apply more than one type of stimulation. Typically, the local brain stimulation tool is configured to apply stimulation in pulses and not in a continuous wave (CW) mode.

The tool can apply either non-invasive or invasive stimulations.

Representative examples of types of non-invasive local brain stimulations suitable for the present embodiments include, without limitation transcranial magnetic stimulation (TMS), Transcranial Electrical Stimulation (tES), focused ultrasound stimulation (FUS) and electroconvulsive therapy (ECT).

Representative examples of types of transcranial magnetic stimulations suitable for the present embodiments include, without limitation, repetitive Transcranial Magnetic Stimulation (rTMS), deep Transcranial magnetic stimulation (dTMS), multichannel TMS and multichannel (dTMS). Representative examples of types of transcranial electrical stimulations suitable for the present embodiments include, without limitation, Transcranial direct current stimulation (tDCS), Transcranial alternate current stimulation (tACS), Transcranial random noise stimulation (tRNS), High definition tES (HD-tES), High definition tDCS (HD-tDCS), and multichannel tES. Also contemplated are optical stimulations, such as, but not limited to, transcranial infrared laser stimulation or the like.

Representative examples of types of invasive local brain stimulations suitable for the present embodiments include, without limitation electrical invasive stimulation, such as, but not limited to, Deep brain stimulation (DBS) and multifocal DBS.

tES can be either multi-focal or single focal. tES can be employed using any number of electrodes. Typically, the number of electrodes is from 1 to 256, but use of more than 256 electrodes is also contemplated in some embodiments of the present invention.

tDCS and HD-tDCS suitable for the present embodiments are found for example, in Edwards et al., NeuroImage 74 (2013) 266-275; Kuo et al., Brain Stimulation, Volume 6, Issue 4 (2013) 644-648; and Villamar et al., J Pain. (2013) 14(4):371-83, the contents of which are hereby incorporated by reference.

Also contemplated is invasive or no-invasive stimulation by a laser beam, as described, for example, in U.S. Pat. Nos. 8,498,708 and 8,506,613, and combination of any of the above stimulations with invasive or no-invasive stimulation by a laser beam.

The frequencies associated with the nodes of the BNA patterns are characteristic to brain waves (typically less than 100 Hz or less than 80 Hz or less that 30 Hz). These frequencies are relatively low and are not to be confused with the frequencies of the waves that are generated by the local brain stimulation tool. Thus, the frequency for which the tool is configured for typically corresponds to a pulse repetition rate of the local brain stimulation tool, rather than the frequency of the wave generated by the tool.

In some embodiments of the present invention the method continues to 206 at which the local brain stimulation tool is operated to apply local brain stimulation to the subject, for example, to treat a brain disorder of the subject. Operation 206 can be executed either when the subject remains conscious, or with application of local anesthesia or mild sedation or general anesthesia.

Representative examples of brain disorders or conditions treatable by operation 206 include, without limitation, attention deficit hyperactivity disorder (ADHD), stroke, traumatic brain injury (TBI), mild TBI (commonly known as brain concussion), posttraumatic stress disorder (PTSD), pain (e.g., labor pain, acute pain, chronic pain, mechanical pain, static allodynia, dynamic allodynia, bone cancer pain, headache, osteoarthritic pain, inflammatory pain, and pain associated with autoimmune disorders or fibromyalgia), epilepsy, Parkinson, multiple sclerosis, agitation, abuse, Alzheimer's disease/dementia, anxiety, panic, phobic disorder, bipolar disorder, borderline personality disorder, behavior control problems, body dysmorphic disorder, cognitive problems (e.g., mild cognitive impairment), depression, dissociative disorders, eating disorder, appetite disorder, fatigue, hiccups, impulse-control problems, irritability, mood problems, movement problems, obsessive-compulsive disorder, personality disorders, schizophrenia and other psychotic disorders, seasonal affective disorder, sexual disorders, sleep disorders, stuttering, substance abuse, Tourette's Syndrome, Trichotillomania, or violent/self-destructive behaviors.

The phrase "inflammatory pain" means pain due to edema or swelling of any inflamed tissue, including inflammatory joint pain. Inflammatory joint pain includes rheumatoid arthritic pain.

The phrase "acute pain" means any pain, including, but not limited to, joint pain, osteoarthritic pain, rheumatoid arthritic pain, inflammatory pain, pain from a burn, pain from a cut, surgical pain, pain from fibromyalgia, bone cancer pain, menstrual pain, back pain, headache, static allodynia, and dynamic allodynia, that lasts from 1 minute to 91 days, 1 minute to 31 days, 1 minute to 7 days, 1 minute to 5 days, 1 minute to 3 days, 1 minute to 2 days, 1 hour to 91 days, 1 hour to 31 days, 1 hour to 7 days, 1 hour to 5 days, 1 hour to 3 days, 1 hour to 2 days, 1 hour to 24 hours, 1 hour to 12 hours, or 1 hour 15 to 6 hours, per occurrence if left untreated. Acute pain includes, but is not limited to, joint pain, osteoarthritic pain, rheumatoid arthritic pain, inflammatory pain, pain from a burn, pain from a cut, surgical pain, pain from fibromyalgia, bone cancer pain, menstrual pain, back pain, headache, static allodynia, dynamic allodynia, acute joint pain, acute osteoarthritic pain, acute rheumatoid arthritic pain, acute inflammatory pain, acute headache, acute menstrual pain, acute back pain, and acute pain from fibromyalgia. Acute pain may be selected from acute joint pain, acute osteoarthritic pain, acute rheumatoid arthritic pain, acute inflammatory pain, acute headache, acute menstrual pain, and acute back pain. Acute pain may be selected from acute joint pain, acute osteoarthritic pain, acute rheumatoid arthritic pain, and acute inflammatory pain. Acute pain may be selected from acute joint pain, acute osteoarthritic pain, and acute rheumatoid arthritic pain. Acute pain may be selected from acute joint pain and acute osteoarthritic pain.

It is to be understood that operation 206 is optional and in some embodiments it is not executed at all.

In embodiments in which operation 206 is employed, both the frequency and the location of the stimulation is preferably selected based on the comparison between the reference BNA pattern and the current-state BNA pattern. In some embodiments of the present invention the local brain stimulation tool is operated to apply local brain stimulation at a plurality of different brain locations and a plurality of different frequencies, wherein each location and each frequency is optionally and preferably selected based on the comparison.

The present embodiments also contemplate combining both transcranial stimulation and deep brain stimulation (DBS). These embodiments are useful since the transcranial stimulation (e.g., tDCS or HD-tDCS) can improve the effectiveness of DBS. In some embodiments the transcranial stimulation (e.g., tDCS or HD-tDCS) is executed before the DBS, wherein the closed-loop with a BNA pattern analysis or capsule analysis as further detailed hereinbelow is used for identifying the effect of the stimulation on the brain. Once the effect is established DBS can be applied at locations at which the transcranial stimulation (e.g., tDCS or HD-tDCS) is more effective (e.g., most effective).

In some embodiments of the present invention the transcranial stimulation (e.g., tDCS or HD-tDCS) is applied simultaneously or intermittently with the DBS. This improves the effectiveness of the treatment by DBS. The combined stimulation (transcranial and DBS, e.g., tES and DBS) can optionally and preferably be achieved by means of the BNA pattern analysis or capsule analysis, described in more detail below, wherein regions on the BNA pattern that are far from the location of the DBS electrodes are stimulated transcranially, and regions on the BNA pattern that are near the location of the DBS electrodes are stimulated by the DBS electrodes. The combined stimulation (transcranial and DBS, e.g., tES and DBS) can be employed for activating and/or inhibiting activities in various regions in the brain, as manifested by the BNA pattern, either synchronously or independently. In some exemplary embodiments of the invention the combined stimulation (transcranial and DBS, e.g., tES and DBS) is employed such that the transcranial stimulation (e.g., tDCS or HD-tDCS) is executed to control activation thresholds for the DBS. For example, the transcranial stimulation can lower the activation threshold at brain regions that are peripheral to the brain regions affected by DBS, thereby extending the effective range of the DBS. The transcranial stimulation can also increases the activation threshold at brain regions affected by DBS thereby controlling the stimulation path of the DBS.

DBS can optionally and preferably be employed to obtain neurophysiological data from the brain. These data can according to some embodiments of the present invention be used by the method to update the BNA pattern.

In some embodiments of the present invention the stimulation also includes a technique known as electroconvulsive therapy (ECT).

The local stimulation can be at one or more locations corresponding to a spatial location of at least one of the nodes of the BNA pattern. For example, the BNA pattern can be analyzed to identify locations that correspond to a brain disorder. At these locations, local stimulation can be applied to reduce or eliminate the disorder. Alternatively, the local stimulation can be applied at locations corresponding to other nodes of the BNA pattern. These other locations can be locations at which previous stimulations for the same subject or group of subjects have been proven to be successful in reducing or eliminating the disorder.

Optionally, the stimulation is executed immediately before, during or after the subject performs a task and/or action. In some embodiments of the present invention the stimulation is executed immediately before, during or after the subject conceptualizes a task and/or action but has not actually performed the task. These embodiments are useful when the subject is suffering from some type of physical and/or cognitive deficit that may prevent actual execution of a task and/or action, as for example may be seen in response to various brain injuries such as stroke. Nevertheless, these embodiments can be employed for any subject, if desired.

After the task is completed, a BNA pattern is reconstructed for the subject. The reconstructed BNA pattern can be compared to the BNA pattern before the task or the reference BNA pattern, and the parameters of the tasks can be varied based on the comparison.

Various types of tasks are contemplated, both lower-level and higher-level cognitive tasks and/or actions. The task/action can be single, serial or on-going. An example of an on-going lower-level cognitive task/action includes, without limitation, watching a movie; an example of a single lower-level cognitive task/action includes, without limitation, providing an audible signal (e.g., a simple sound) to the subject; and an example of a serial lower-level cognitive task/action includes, without limitation, playing an audible signal repeatedly. It is appreciated that for a repetitive task the subject may eventually be conditioned and will pay less attention (a process known as habituation), but there still will be a response from the brain. An example of a higher-level cognitive task/action includes, without limitation, the so called "Go/NoGo task" in which the subject is requested to push a button if a high pitch sound is heard, wherein if a low pitch sound is heard then the subject is not to push the button. This task is known in the art and is used in many cognitive studies.

Many task protocols are known in the art, all of which are contemplated by some embodiments of the present invention. For example, a stimulus-response neuropsychological test can be employed. Representative example of such tests include, without limitation, the Stroop task, the Wisconsin card sorting test, and the like; stimulus-only based tests include, without limitation, mismatch negativity, brain-stem-evoked response audiometry (BERA), and the like. Also contemplated are response-only based tests, such as, but not limited to, saccade analysis, movement related potentials (MRP), N-back memory tasks and other working memory tasks, the "serial seven" test (counting back from 100 in jumps of seven), the Posner attention tasks and the like.

In addition or instead of cognitive tasks, the present embodiments also contemplate identification of potentials evoked responsively to neurostimulation. A representative example including, without limitation, TMS evoked potentials.

Following stimulation (which is not necessarily applied by the method), the method optionally and preferably continues to 207 at which a post-stimulation BNA pattern is obtained. The post-stimulation BNA pattern describes the neurophysiological state of the subject following the stimulation. The method can then continue to 208 at which the post-stimulation BNA pattern is compared with the BNA pattern obtained at 203, and to 209 at which the effect of stimulation is assessed based on the comparison. When the stimulation is executed immediately before, during or immediately after the subject performs or conceptualize a task, the parameters of the tasks can be varied based on the comparison 208.

The results of the assessment can be displayed on a display device, printed or transmitted to a computer readable medium.

The method ends at 210.

FIG. 32 is a schematic illustration of a system 430 suitable for treating a subject, according to some embodiments of the present invention. System 430 typically comprises a data processing system 431 and a controller 450. System 431 comprises a computer 433, which typically comprises an input/output (I/O) circuit 434, a data processor, such as a central processing unit (CPU) 436 (e.g., a microprocessor), and a memory 446 which typically includes both volatile memory and non-volatile memory. I/O circuit 434 is used to communicate information in appropriately structured form to and from other CPU 436 and other devices or networks external to system 430. CPU 436 is in communication with I/O circuit 434 and memory 438. These elements are those typically found in most general purpose computers and are known per se.

A display device 440 is shown in communication with computer 433, typically via I/O circuit 434. Computer 433 issues to display device 440 graphical and/or textual output images generated by CPU 436. A keyboard 442 is also shown in communication with computer 433, typically I/O circuit 434.

It will be appreciated by one of ordinary skill in the art that system 431 can be part of a larger system. For example, system 431 can also be in communication with a network, such as connected to a local area network (LAN), the Internet or a cloud computing resource of a cloud computing facility.

Controller 450 can be connected to a brain stimulation tool 452 which can be configured to apply any of the aforementioned types of local brain stimulations, and combinations of local brain stimulations.

Data processing system 431 is preferably configured for obtaining a reference BNA pattern and a current-state BNA pattern, and for comparing the BNA patterns as further detailed hereinabove.

Controller 450 is preferably configured for controlling brain stimulation tool 452 to apply the local brain stimulation at a location and a frequency selected based on comparison, as further detailed hereinabove.

In some optional embodiments of the present invention, system 430 comprises a sensing system 424 configured for sensing and/or recording the neurophysiological data and feeding data processor 433 with the data. In these embodiments, data processor 433 is also configured for constructing at least one of the BNA patterns based on the received data. Representative examples how to construct a BNA pattern by analyzing neurophysiological data is provided hereinbelow.

In some embodiments of the present invention sensing system 424 processor 433 and controller 450 operate in a closed loop, wherein processor 433 constructs, based on the data from sensing system 442, a post-stimulation BNA pattern which provides indication regarding the effectiveness of the stimulation, and compares between the BNA patterns of the subject before and after the stimulation, and wherein controller 450 adjusts the parameters of the stimulation (e.g., frequency, location) responsively to the comparison. Such a closed loop can be used to effect many types of changes in brain function. Representative examples include, without limitation, inducing of local neuroplasticity, inhibition of local activity, synchronization among different brain regions (nearby or remote from each other), and the like.

Figure 1:
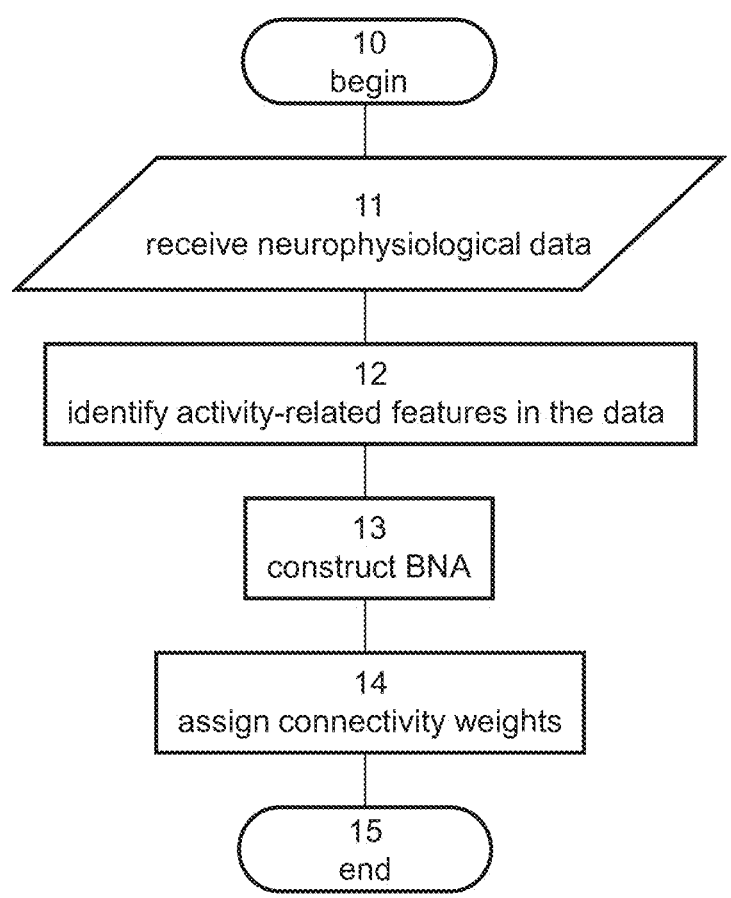

FIG. 1 is a flowchart diagram of a method suitable for analyzing neurophysiological data, according to various exemplary embodiments of the present invention. The method can be used for constructing a BNA pattern.

The neurophysiological data to be analyzed can be any data acquired directly from the brain of the subject under investigation. The data acquired "directly" in the sense that it shows electrical, magnetic, chemical or structural features of the brain tissue itself. The neurophysiological data can be data acquired directly from the brain of a single subject or data acquired directly from multiple brains of respective multiple subjects (e.g., a research group), not necessarily simultaneously.

Analysis of data from multiple brains can be done by performing the operations described below separately for each portion of the data that correspond to a single brain. Yet, some operations can be performed collectively for more than one brain. Thus, unless explicitly state otherwise, a reference to "subject" or "brain" in the singular form does not necessarily mean analysis of data of an individual subject. A reference to "subject" or "brain" in the singular form encompasses also analysis of a data portion which corresponds to one out of several subjects, which analysis can be applied to other portions as well.

The data can be analyzed immediately after acquisition ("online analysis"), or it can be recorded and stored and thereafter analyzed ("offline analysis").

Representative example of neurophysiological data types suitable for the present invention, including, without limitation, electroencephalogram (EEG) data, magnetoencephalography (MEG) data, computer-aided tomography (CAT) data, positron emission tomography (PET) data, magnetic resonance imaging (MRI) data, functional MRI (fMRI) data, ultrasound data, single photon emission computed tomography (SPECT) data, Brain Computer Interface (BCI) data, and data from neuroprostheses at the neural level.

In various exemplary embodiments of the invention the neurophysiological data are associated with signals collected using a plurality of measuring devices respectively placed at a plurality of different locations on the scalp of the subject. In these embodiments, the data type is preferably EEG or MEG data. The measuring devices can include electrodes, superconducting quantum interference devices (SQUIDs), and the like. The portion of the data that is acquired at each such location is also referred to as "channel." In some embodiments, the neurophysiological data are associated with signals collected using a plurality of measuring devices placed in the brain tissue itself. In these embodiments, the data type is preferably invasive EEG data, also known as electrocorticography (ECoG) data. Also contemplated are data acquired by invasive devices implanted in the cortex itself. For example, when the subject is implanted with DBS electrodes, these DBS electrodes can be used also for collecting data.

Optionally, the data include combination of two or more different types of data. In a preferred embodiment, the data include EEG data and, in addition, data of type other than EEG. In a preferred embodiment, the data include MEG data and, in addition, data of type other than MEG.

Optionally and preferably, the neurophysiological data is collected at least before and after the subject has performed a task and/or action. In some embodiments of the present invention the neurophysiological data is collected at least before and after the subject has conceptualized a task and/or action but has not actually performed the task. These embodiments are useful when the subject is suffering from some type of physical and/or cognitive deficit that may prevent actual execution of a task and/or action, as for example may be seen in response to various brain injuries such as stroke. Nevertheless, these embodiments can be employed for any subject, if desired.

Neurophysiological data which is associated with a task and/or action (whether actually performed or conceptualized) can be used as event related measures, such as event related potentials (ERPs) or event related fields (ERFs). The task and/or action (whether actually performed or conceptualized) is preferably in response to a stimulus or stimuli, and the acquisition of data is synchronized with the stimulus to establish a timeline of the response and extract data features responsively to this timeline. Typically, but not necessarily, the data collection is on-going such that neurophysiological data are collected continuously before, during and after performance or conceptualization of the task and/or action.

Any of the aforementioned types of tasks and task protocols is contemplated.

It is to be understood that it is not intended to limit the scope of the present invention only to neurophysiological data associated with stimulus, task and/or action. Embodiments of the present invention can be applied also to neurophysiological data describing spontaneous brain activity. Also contemplated are embodiments in which the neurophysiological data are acquired during particular activities, but the acquisition is not synchronized with a stimulus.

Referring now to FIG. 1, the method begins at 10 and optionally and preferably continues to 11 at which the neurophysiological data are received. The data can be recorded directly from the subject or it can be received from an external source, such as a computer readable memory medium on which the data are stored.

The method continues to 12 at which relations between features of the data are determined so as to identify activity-related features. This can be done using any procedure known in the art. For example, procedures as described in International Publication Nos. WO 2007/138579, WO 2009/069134, WO 2009/069135 and WO 2009/069136, the contents of which are hereby incorporated by reference, can be employed. Broadly speaking, the extraction of activity-related features includes multidimensional analysis of the data, wherein the data is analyzed to extract spatial and non-spatial characteristics of the data.

The spatial characteristics preferably describe the locations from which the respective data were acquired. For example, the spatial characteristics can include the locations of the measuring devices (e.g., electrode, SQUID) on the scalp of the subject.

Also contemplated are embodiments in which the spatial characteristics estimate the locations within the brain tissue at which the neurophysiological data were generated. In these embodiments, a source localization procedure, which may include, for example, low resolution electromagnetic tomography (LORETA), is employed. A source localization procedure suitable for the present embodiments is described in the aforementioned international publications which are incorporated by reference. Other source localization procedure suitable for the present embodiments are found in Greenblatt et al., 2005, "Local Linear Estimators for the Bioelectromagnetic Inverse Problem," IEEE Trans. Signal Processing, 53(9):5430; Sekihara et al., "Adaptive Spatial Filters for Electromagnetic Brain Imaging (Series in Biomedical Engineering)", Springer, 2008; and Sekihara et al., 2005, "Localization bias and spatial resolution of adaptive and non-adaptive spatial filters for MEG source reconstruction", NeuroImage 25:1056; the contents of which are hereby incorporated by reference.

Additionally contemplated are embodiments in which the spatial characteristics estimate locations on the epicortical surface. In these embodiments, data collected at locations on the scalp of the subject are processed so as to map the scalp potential distribution onto the epicortical surface. The technique for such mapping is known in the art and referred to in the literature as Cortical Potential Imaging (CPI) or Cortical Source Density (CSD). Mapping techniques suitable for the present embodiments are found in Kayser et al., 2006, "Principal Components Analysis of Laplacian Waveforms as a Generic Method for Identifying ERP Generator Patterns: I. Evaluation with Auditory Oddball Tasks," Clinical Neurophysiology 117(2):348; Zhang et al., 2006, "A Cortical Potential Imaging Study from Simultaneous Extra- and Intra-cranial Electrical Recordings by Means of the Finite Element Method," Neuroimage, 31(4): 1513; Perrin et al., 1987, "Scalp Current Density Mapping: Value and Estimation from Potential Data," IEEE transactions on biomedical engineering, BME-34(4):283; Ferree et al., 2000, "Theory and Calculation of the Scalp Surface Laplacian", www(dot)csi(dot)uoregon(dot)edu/members/ferree/tutorials/SurfaceLaplacian; and Babiloni et al., 1997, "High resolution EEG: a new model-dependent spatial deblurring method using a realistically-shaped MR-constructed subject's head model", Electroencephalography and clinical Neurophysiology 102:69.

In any of the above embodiments, the spatial characteristics can be represented using a discrete or continuous spatial coordinate system, as desired. When the coordinate system is discrete, it typically corresponds to the locations of the measuring devices (e.g., locations on the scalp, epicortical surface, cerebral cortex or deeper in the brain). When the coordinate system is continuous, it preferably describes the approximate shape of the scalp or epicortical surface, or some sampled version thereof. A sampled surface can be represented by a point-cloud which is a set of points in a three-dimensional space, and which is sufficient for describing the topology of the surface. For a continuous coordinate system, the spatial characteristics can be obtained by piecewise interpolation between the locations of the measuring devices. The piecewise interpolation preferably utilizes a smooth analytical function or a set of smooth analytical functions over the surface.

In some embodiments of the invention the non-spatial characteristics are obtained separately for each spatial characteristic. For example, the non-spatial characteristics can be obtained separately for each channel. When the spatial characteristics are continuous, the non-spatial characteristics are preferably obtained for a set of discrete points over the continuum. Typically, this set of discrete points includes at least the points used for the piecewise interpolation, but may also include other points over the sampled version of the surface.

The non-spatial characteristics preferably include temporal characteristics, which are obtained by segmenting the data according to the time of acquisition. The segmentation results in a plurality of data segments each corresponding to an epoch over which the respective data segment was acquired. The length of the epoch depends on the temporal resolution characterizing the type of neurophysiological data. For example, for EEG or MEG data, a typical epoch length is approximately 1000 ms.

Other non-spatial characteristics can be obtained by data decomposing techniques. In various exemplary embodiments of the invention the decomposition is performed separately for each data segment of each spatial characteristic. Thus, for a particular data channel, decomposition is applied, e.g., sequentially to each data segment of this particular channel (e.g., first to the segment that corresponds to the first epoch, then to the segment that correspond to the second epoch and so on). Such sequential decomposition is performed for other channels as well.

The neurophysiological data can be decomposed by identifying a pattern of extrema (peaks, troughs, etc.) in the data, or, more preferably by means of waveform analysis, such as, but not limited to, wavelet analysis. In some embodiments of the present invention the extremum identification is accompanied by a definition of a spatiotemporal neighborhood of the extremum. The neighborhood can be defined as a spatial region (two- or three-dimensional) in which the extremum is located and/or a time-interval during which the extremum occurs. Preferably, both a spatial region and time-interval are defined, so as to associate a spatiotemporal neighborhood for each extremum. The advantage of defining such neighborhoods is that they provide information regarding the spreading structure of the data over time and/or space. The size of the neighborhood (in terms of the respective dimension) can be determined based on the property of the extremum. For example, in some embodiments, the size of the neighborhood equals the full width at half maximum (FWHM) of the extremum. Other definitions of the neighborhood are not excluded from the scope of the present invention.

The waveform analysis is preferably accompanied by filtering (e.g., bandpass filtering) such that the wave is decomposed to a plurality of overlapping sets of signal extrema (e.g., peaks) which together make up the waveform. The filters themselves may optionally be overlapping.

When the neurophysiological data comprise EEG data, one or more of the following frequency bands can be employed during the filtering: delta band (typically from about 1 Hz to about 4 Hz), theta band (typically from about 3 to about 8 Hz), alpha band (typically from about 7 to about 13 Hz), low beta band (typically from about 12 to about 18 Hz), beta band (typically from about 17 to about 23 Hz), and high beta band (typically from about 22 to about 30 Hz). Higher frequency bands, such as, but not limited to, gamma band (typically from about 30 to about 80 Hz), are also contemplated.

Following the waveform analysis, waveform characteristics, such as, but not limited to, time (latency), frequency and optionally amplitude are preferably extracted. These waveform characteristics are preferably obtained as discrete values, thereby forming a vector whose components are the individual waveform characteristics. Use of discrete values is advantageous since it reduces the amount of data for further analysis. Other reduction techniques, such as, but not limited to, statistical normalization (e.g., by means of standard score, or by employing any statistical moment) are also contemplated. Normalization can be used for reducing noise and is also useful when the method is applied to data acquired from more than one subject and/or when the interfaces between the measuring device and the brain vary among different subjects or among different locations for a single subject. For example, statistical normalization can be useful when there is non-uniform impedance matching among EEG electrodes.

The extraction of characteristics results in a plurality of vectors, each of which includes, as the components of the vector, the spatial characteristics (e.g., the location of the respective electrode or other measuring device), and one or more non-spatial characteristics as obtained from the segmentation and decomposition. Each of these vectors is a feature of the data, and any pair of vectors whose characteristics obey some relation (for example, causal relation wherein the two vectors are consistent with flow of information from the location associated with one vector to the location associated with the other vector) constitutes two activity-related features.

The extracted vectors thus define a multidimensional space. For example, when the components include location, time and frequency, the vectors define a three-dimensional space, and when the components include location, time, frequency and amplitude, the vectors define a four-dimensional space. Higher number of dimensions is not excluded from the scope of the present invention.

When the analysis is applied to neurophysiological data of one subject, each feature of the data is represented as a point within the multidimensional space defined by the vectors, and each set of activity-related features is represented as a set of points such that any point of the set is within a specific distance along the time axis (also referred to hereinbelow as "latency-difference") from one or more other points in the set.

When the analysis is applied to neurophysiological data acquired from a group or sub-group of subjects, a feature of the data is preferably represented as a cluster of discrete points in the aforementioned multidimensional space. A cluster of points can also be defined when the analysis is applied to neurophysiological data of a single subject. In these embodiments, vectors of waveform characteristics are extracted separately for separate stimuli presented to the subject, thereby defining clusters of points within the multidimensional space, where each point within the cluster corresponds to a response to a stimulus applied at a different time. The separate stimuli optionally and preferably form a set of repetitive presentations of the same or similar stimulus, or a set of stimuli which are not necessarily identical but are of the same type (e.g., a set of not-necessarily identical visual stimuli). Use of different stimuli at different times is not excluded from the scope of the present invention.

Also contemplated are combinations of the above representations, wherein data are collected from a plurality of subjects and for one or more of the subjects, vectors of waveform characteristics are extracted separately for time-separated stimuli (i.e., stimuli applied at separate times). In these embodiments, a cluster contains points that correspond to different subjects as well as points that correspond to a response to a separated stimulus. Consider, for example, a case in which data were collected from 10 subjects, wherein each subject was presented with 5 stimuli during data acquisition. In this case, the dataset includes 5×10=50 data segment, each corresponding to a response of one subject to one stimulus. Thus, in a cluster within the multidimensional space may include up to 5×10 points, each representing a vector of characteristics extracted from one of the data segments.

Whether representing characteristics of a plurality of subjects and/or characteristics of a plurality of responses to stimuli presented to a single subject the width of a cluster along a given axis of the space describes a size of an activity window for the corresponding data characteristic (time, frequency, etc). As a representative example, consider the width of a cluster along the time axis. Such width is optionally and preferably used by the method to describe the latency range within which the event occurs across multiple subjects. Similarly, the width of a cluster along the frequency axis can be used for describing the frequency band indicating an occurrence of an event occurring across multiple subjects; the widths of a cluster along the location axes (e.g., two location axes for data corresponding to a 2D location map, and three location axes for data corresponding to a 3D location map) can be used to define a set of adjoining electrodes at which the event occurs across multiple subjects, and the width of a cluster along the amplitude axis can be used to define an amplitude range indicating an occurrence of event across multiple subjects.

For a group or sub-group of subjects, activity-related features can be identified as follows. A single cluster along the time axis is preferably identified as representing a unitary event occurring within a time window defined, as stated, by the width of the cluster. This window is optionally and preferably narrowed to exclude some outlier points, thereby redefining the latency range characterizing the respective data feature. For a succession of clusters along the time axis, wherein each cluster in the series has a width (along the time axis) within a particular constraint, a pattern extraction procedure is preferably implemented for identifying those clusters which obey connectivity relations thereamongst. Broadly speaking such procedure can search over the clusters for pairs of clusters in which there are connectivity relations between a sufficient number of points between the clusters.

The pattern extraction procedure can include any type of clustering procedures, including, without limitation, a density-based clustering procedure, a nearest-neighbor-based clustering procedure, and the like. A density-based clustering procedure suitable for the present embodiments is described in Cao et al., 2006, "Density-based clustering over an evolving data stream with noise," Proceedings of the Sixth SIAM International Conference on Data Mining. Bethesda, Md., p. 328-39. A nearest-neighbor clustering procedure suitable for the present embodiments is described in [R. O. Duda, P. E. Hart and D. G. Stork, "Pattern Classification" (2nd Edition), A Wiley-Interscience Publication, 2000]. When nearest-neighbor clustering procedure is employed, clusters are identified and thereafter gathered to form meta-clusters based on spatiotemporal distances among the clusters. The meta-clusters are, therefore, clusters of the identified clusters. In these embodiments, the meta-clusters are the features of the data, and activity-related features are identified among the meta-clusters.

FIG. 3A is a flowchart diagram describing a procedure for identifying activity-related features for a group of subjects, according to some embodiments of the present invention. The procedure begins at 40 and continues to 41 at which isolated clusters are identified. The present embodiments contemplate both subspace clustering, wherein clusters are identified on a particular projection of the multidimensional space, and full-space clustering wherein clusters are identified on the entire multidimensional space. Subspace clustering is preferred from the standpoint of computation time, and full-space clustering is preferred from the standpoint of features generality.

One representative example of subspace clustering includes identification of clusters along the time axis, separately for each predetermined frequency band and each predetermined spatial location. The identification optionally and preferably features a moving time-window with a fixed and predetermined window width. A typical window width for EEG data is about 200 ms for the delta band. A restriction on a minimal number of points in a cluster is optionally applied so as not to exclude small clusters from the analysis. Typically cluster with less than X points, where X equals about 80% of the subjects in the group, are excluded. The minimal number of points can be updated during the procedure. Once an initial set of clusters is defined, the width of the time window is preferably lowered.

Another representative example of subspace clustering includes identification of clusters over a space-time subspace, preferably separately for each predetermined frequency band. In this embodiment, the extracted spatial characteristics are represented using a continuous spatial coordinate system, e.g., by piecewise interpolation between the locations of the measuring devices, as further detailed hereinabove. Thus, each cluster is associated with a time window as well as a spatial region, wherein the spatial region may or may not be centered at a location of a measuring device. In some embodiments, at least one cluster is associated with a spatial region which is centered at a location other than a location of a measuring device. The space-time subspace is typically three-dimensional with one temporal dimension and two spatial dimensions, wherein each cluster is associated with a time-window and a two-dimensional spatial region over a surface which may correspond, e.g., to the shape of the scalp surface, the epicortical surface and the like. Also contemplated is a four-dimensional space-time space wherein each cluster is associated with a time-window and a three-dimensional spatial region over a volume corresponding, at least in part, to internal brain.

Another representative example of subspace clustering includes identification of clusters over a frequency-space-time subspace. In this embodiment, instead of searching for clusters separately for each predetermined frequency band, the method allows identification of clusters also at frequencies which are not predetermined. Thus, the frequency is considered as a continuous coordinate over the subspace. As in the embodiment of space-time subspace, the extracted spatial characteristics are represented using a continuous spatial coordinate system. Thus, each cluster is associated with a time window, a spatial region and a frequency band. The spatial region can be two- or three-dimensional as further detailed hereinabove. In some embodiments, at least one cluster is associated with a spatial region which is centered at a location other than a location of a measuring device, and at least one cluster is associated with a frequency band which includes frequencies of two or more of the delta, theta, alpha, low beta, beta, high beta and gamma bands. For example, a cluster can be associated with a frequency band spanning over part of the delta band and part of the theta band, or part of the theta band and part of the alpha band, or part of the alpha band and part of the low beta band, etc.

The procedure optionally and preferably continues to 42 at which, a pair of clusters is selected. The procedure optionally and preferably continues to 43 at which, for each subject that is represented in the selected pair, latency difference (including zero difference) between the corresponding events is optionally calculated. The procedure continues to 44 at which a constraint is applied to the calculated latency differences such that latency differences which are outside a predetermined threshold range (e.g., 0-30 ms) are rejected while latency differences which are within the predetermined threshold range are accepted. The procedure continues to decision 45 at which the procedure determines whether the number of accepted differences is sufficiently large (i.e., above some number, e.g., above 80% of the subjects in the group). If the number of accepted differences is not sufficiently large the procedure proceeds to 46 at which the procedure accepts the pair of clusters and identifies it as a pair of activity-related features. If the number of accepted differences is sufficiently large the procedure proceeds to 47 at which the procedure reject the pair. From 46 or 47 the procedure of the present embodiments loops back to 42.

An illustrative example for determining relations among the data features and identification of activity-related features is shown in FIG. 3B. The illustration is provided in terms of a projection onto a two-dimensional space which includes time and location. The present example is for an embodiment in which the spatial characteristics are discrete, wherein the identification of clusters is along the time axis, separately for each predetermined frequency band and each predetermined spatial location. The skilled person would know how to adapt the description for the other dimensions, e.g., frequency, amplitude, etc. FIG. 3B illustrates a scenario in which data are collected from 6 subjects (or from a single subject, presented with 6 stimuli at different times), enumerated 1 through 6. For clarity of presentation, different data segments data (e.g., data collected from different subjects, or from the same subject but for stimuli of different times) are separated along a vertical axis denoted "Data Segment No." For each segment, an open circle represents an event recorded at one particular location (by means of a measuring device, e.g., EEG electrode) denoted "A", and a solid disk represents an event recorded at another particular location denoted "B".

The time axis represents the latency of the respective event, as measured, e.g., from a time at which the subject was presented with a stimulus. The latencies of the events are denoted herein $t^{(i)}_A$ and $t^{(i)}_B$, where i represents the segment index (i=1, . . . , 6) and A and B represent the location. For clarity of presentation, the latencies are not shown in FIG. 3B, but one of ordinary skills in the art, provided with the details described herein would know how to add the latencies to the drawing.

For each of locations A and B, a time window is defined. These time windows, denoted $\Delta t_A$ and $\Delta t_B$, correspond to the width of the clusters along the time axis and they can be the same or different from one another, as desired. Also defined is a latency difference window $\Delta t_{AB}$, between the two unitary events. This window corresponds to the separation along the time axis between the clusters (e.g., between their centers). The window $\Delta t_{AB}$ is illustrated as an interval having a dashed segment and a solid segment. The length of the dashed segment represents the lower bound of the window and the overall length of the interval represents the upper bound of the window. $\Delta t_A$, $\Delta t_B$ and $\Delta t_{AB}$ are part of the criteria for determining whether to accept the pair of events recorded at A and B as activity-related features.

The time windows $\Delta t_A$ and $\Delta t_B$ are preferably used for identifying unitary events in the group. As shown, for each of segment Nos. 1, 2, 4 and 5 both events fall within the respective time windows (mathematically, this can be written as follows: $t^{(i)}_A \in \Delta t_A$, $t^{(i)}_B \in \Delta t_A$, i=1, 2, 4, 5). On the other hand, for segment No. 3 the event recorded at A falls outside $\Delta t_A (t^{(3)}_A \notin \Delta t_A)$ while the event recoded at B falls within $\Delta t_B (t^{(3)}_B \in \Delta t_B)$, and for segment No. 6 the event recorded at A falls within $\Delta t_A (t^{(6)}_A \in \Delta t_A)$ while the event recoded at B falls outside $\Delta t_B$ $(t^{(6)}_B \notin \Delta t_B)$. Thus, for location A, a unitary event is defined as a cluster of data points obtained from segment Nos. 1, 2, 4, 5 and 6, and for location B, a unitary event is defined as a cluster of data points obtained from segment Nos. 1-5.

The latency difference window $\Delta t_{AB}$ is preferably used for identifying activity-related features. In various exemplary embodiments of the invention the latency difference $\Delta t^{(i)}_{AB}$ (i=1, 2, . . . , 5) of each segment is compared to the latency difference window $\Delta t_{AB}$. In various exemplary embodiments of the invention a pair of features is accepted as an activity-related pair if (i) each of the features in the pair belongs to a unitary event, and (ii) the corresponding latency difference falls within $\Delta t_{AB}$. In the illustration of FIG. 3B, each of the pairs recorded from segment Nos. 4 and 5 is accepted as a pair of activity-related features, since both criteria are met for each of those segment ($\Delta t^{(i)}_{AB} \in \Delta t_{AB}$, $t^{(i)}_A \in \Delta t_A$, $t^{(i)}_B \in \Delta t_A$, i=4, 5). The pairs recorded from segment Nos. 1-3 do not pass the latency difference criterion since each of $\Delta t^{(1)}_{AB}$, $\Delta t^{(2)}_{AB}$ and $\Delta t^{(3)}_{AB}$ is outside $\Delta t_{AB}$ ($\Delta t^{(i)}_{AB} \notin \Delta t_{AB}$, i=1, 2, 3). These pairs are, therefore, rejected. Notice that in the present embodiment, even though the pair obtained from segment No. 6 passes the latency difference criterion, the pair is rejected since it fails to pass the time-window criterion ($\Delta t^{(6)}_{AB} \notin \Delta t_{AB}$).

In various exemplary embodiments of the invention the procedure also accepts pairs corresponding to simultaneous events of the data that occur at two or more different locations. Although such events are not causal with respect to each other (since there is no flow of information between the locations), the corresponding features are marked by the method. Without being bounded to any particular theory, the present inventors consider that simultaneous events of the data are causally related to another event, although not identified by the method. For example, the same physical stimulus can generate simultaneous events in two or more locations in the brain.

The identified pairs of activity-related features, as accepted at 46, can be treated as elementary patterns which can be used as elementary building blocks for constructing complex patterns within the feature space. In various exemplary embodiments of the invention, the method proceeds to 48 at which two or more pairs of activity-related features are joined (e.g., concatenated) to form a pattern of more than two features. The criterion for the concatenation can be similarity between the characteristics of the pairs, as manifested by the vectors. For example, in some embodiments, two pairs of activity-related features are concatenated if they have a common feature. Symbolically, this can be formulated as follows: the pairs "A-B" and "B-C" have "B" as a common feature and are concatenated to form a complex pattern A-B-C.

Preferably, the concatenated set of features is subjected to a thresholding procedure, for example, when X % or more of the subjects in the group are included in the concatenated set, the set is accepted, and when less than X % of the subjects in the group are included in the concatenated set, the set is rejected. A typical value for the threshold X is about 80.

Each pattern of three or more features thus corresponds to a collection of clusters defined such that any cluster of the collection is within a specific latency-difference from one or more other clusters in the collection. Once all pairs of clusters are analyzed the procedures continues to terminator 49 at which it ends.

Referring again to FIG. 1, at 13 a brain network activity (BNA) pattern is constructed.

When BNA pattern 20 is a subject-specific BNA pattern, only vectors extracted from data of the respective subject are used to construct the BNA pattern. Thus, each node corresponds to a point in the multidimensional space and therefore represents an activity event in the brain. When BNA pattern 20 is a group BNA pattern, some nodes can correspond to a cluster of points in the multidimensional space and therefore represents an activity event which is prevalent in the group or sub-group of subjects. Due to the statistical nature of a group BNA pattern, the number of nodes (referred to herein as the "order") and/or edges (referred to herein as the "size") in a group BNA pattern is typically, but not necessarily, larger than the order and/or size of a subject-specific BNA pattern.

As a simple example for constructing a group BNA pattern, the simplified scenario illustrated in FIG. 3B is considered, wherein a "segment" corresponds to a different subject in a group or sub-group of subjects. The group data include, in the present example, two unitary events associated with locations A and B. Each of these events forms a cluster in the multidimensional space. In various exemplary embodiments of the invention each of the clusters, referred to herein as clusters A and B, is represented by a node in the group BNA. The two clusters A and B are identified as activity-related features since there are some individual points within these clusters that pass the criteria for such relation (the pairs of Subject Nos. 4 and 5, in the present example). Thus, in various exemplary embodiments of the invention the nodes corresponding to clusters A and B are connected by an edge. A simplified illustration of the resulting group BNA pattern is illustrated in FIG. 3C.

A subject-specific BNA pattern is optionally and preferably constructed by comparing the features and relations among features of the data collected from the respective subject to the features and relations among features of reference data, which, in some embodiments of the present invention comprise group data. In these embodiments, points and relations among points associated with the subject's data are compared to clusters and relations among clusters associated with the group's data. Consider, for example, the simplified scenario illustrated in FIG. 3B, wherein a "segment" corresponds to a different subject in a group or sub-group of subjects. Cluster A does not include a contribution from Subject No. 3, and cluster B does not include a contribution from Subject No. 6, since for these subjects the respective points fail to pass the time-window criterion. Thus, in various exemplary embodiments of the invention when a subject-specific BNA pattern is constructed for Subject No. 3 it does not include a node corresponding to location A, and when a subject-specific BNA pattern is constructed for Subject No. 6 it does not include a node corresponding to location B. On the other hand, both locations A and B are represented as nodes in the subject-specific BNA patterns constructed for any of Subject Nos. 1, 2, 4 and 5.

For those subjects for which the respective points are accepted as a pair of activity-related features (Subject Nos. 4 and 5, in the present example), the corresponding nodes are preferably connected by an edge. A simplified illustration of a subject-specific BNA pattern for such a case is shown in FIG. 3D.

Note that for this simplified example of only two nodes, the subject-specific BNA of FIG. 3D is similar to the group BNA of FIG. 3C. For a larger number of nodes, the order and/or size of the group BNA pattern is, as stated, typically larger than the order and/or size of the subject-specific BNA pattern. An additional difference between the subject-specific and group BNA patterns can be manifested by the degree of relation between the activity-related features represented by the edges, as further detailed hereinbelow.

For subjects for which the respective points were rejected (Subject Nos. 1 and 2, in the present example), the corresponding nodes are preferably not connected by an edge. A simplified illustration of a subject-specific BNA pattern for such case is shown in FIG. 3E.

It is to be understood, however, that although the above technique for constructing a subject-specific BNA pattern is described in terms of the relation between the data of a particular subject to the data of a group of subjects, this need not necessarily be the case, since in some embodiments, a subject-specific BNA pattern can be constructed only from the data of a single subject. In these embodiments, vectors of waveform characteristics are extracted separately for time-separated stimuli, to define clusters of points where each point within the cluster corresponds to a response to a stimulus applied at a different time, as further detailed hereinabove. The procedure for constructing subject-specific BNA pattern in these embodiments is preferably the same as procedure for constructing a group BNA pattern described above. However, since all data are collected from a single subject, the BNA pattern is subject-specific.

Thus, the present embodiments contemplate two types of subject-specific BNA patterns: a first type that describes the association of the particular subject to a group or sub-group of subjects, which is a manifestation of a group BNA pattern for the specific subject, and a second type that describes the data of the particular subject without associating the subject to a group or sub-group of subjects. The former type of BNA pattern is referred to herein as an associated subject-specific BNA pattern, and the latter type of BNA pattern is referred to herein as an unassociated subject-specific BNA pattern.

For unassociated subject-specific BNA pattern, the analysis is preferably performed on the set of repetitive presentations of a single stimulus, namely on a set of single trials, optionally and preferably before averaging the data and turning it to one single vector of the data. For group BNA patterns, on the other hand, the data of each subject of the group is optionally and preferably averaged and thereafter turned into vectors of the data.

Note that while the unassociated subject-specific BNA pattern is generally unique for a particular subject (at the time the subject-specific BNA pattern is constructed), the same subject may be characterized by more than one associated subject-specific BNA patterns, since a subject may have different associations to different groups. Consider for example a group of healthy subjects and a group of non-healthy subjects all suffering from the same brain disorder. Consider further a subject Y which may or may not belong to one of those groups. The present embodiments contemplate several subject-specific BNA patterns for subject Y. A first BNA pattern is an unassociated subject-specific BNA pattern, which, as stated is generally unique for this subject, since it is constructed from data collected only from subject Y. A second BNA pattern is an associated subject-specific BNA pattern constructed in terms of the relation between the data of a subject Y to the data of the healthy group. A third BNA pattern is an associated subject-specific BNA pattern constructed in terms of the relation between the data of a subject Y to the data of the non-healthy group. Each of these BNA patterns are useful for assessing the condition of subject Y. The first BNA pattern can be useful, for example, for monitoring changes in the brain function of the subject over time (e.g., monitoring brain plasticity or the like) since it allows comparing the BNA pattern to a previously constructed unassociated subject-specific BNA pattern. The second and third BNA pattern can be useful for determining the level of association between subject Y and the respective group, thereby determining the likelihood of brain disorder for the subject.

Also contemplated are embodiments in which the reference data used for constructing the subject-specific BNA pattern corresponds to history data previously acquired from the same subject. These embodiments are similar to the embodiments described above regarding the associated subject-specific BNA pattern, except that the BNA pattern is associated to the history of the same subject instead of to a group of subjects.

Additionally contemplated are embodiments in which the reference data corresponds to data acquired from the same subject at some later time. These embodiments allow investigating whether data acquired at an early time evolve into the data acquired at the later time. A particular and non-limiting example is the case of several treatment sessions, e.g., N sessions, for the same subject. Data acquired in the first several treatment sessions (e.g., from session 1 to session $k_1 < N$) can be used as reference data for constructing a first associated subject-specific BNA pattern corresponding to mid sessions (e.g., from session $k_2 > k_1$ to session $k_3 > k_2$), and data acquired in the last several treatment sessions (e.g., from session $k_4$ to session N) can be used as reference data for constructing a second associated subject-specific BNA pattern corresponding to the aforementioned mid sessions, where $1 < k_1 < k_2 < k_3 < k_4$. Such two associated subject-specific BNA patterns for the same subject can be used for determining data evolution from the early stages of the treatment to the late stages of the treatment.

The method proceeds to 14 at which a connectivity weight is assigned to each pair of nodes in the BNA pattern (or, equivalently, to each edge in the BNA) pattern, thereby providing a weighted BNA pattern. The connectivity weight is represented in FIGS. 2, 3C and 3D by the thickness of the edges connecting two nodes. For example, thicker edges can correspond to higher weights and thinner edges can correspond to lower weights.

In various exemplary embodiments of the invention the connectivity weight comprises a weight index WI calculated based on at least one of the following cluster properties: (i) the number of subjects participating in the corresponding cluster pair, wherein greater weights are assigned for larger number of subjects; (ii) the difference between the number of subjects in each cluster of the pair (referred to as the "differentiation level" of the pair), wherein greater weights are assigned for lower differentiation levels; (iii) the width of the time windows associated with each of the corresponding clusters (see, e.g., $\Delta t_A$ and $\Delta t_B$ in FIG. 3A), wherein greater weights are assigned for narrower windows; (iv) the latency difference between the two clusters (see $\Delta t_{AB}$ in FIG. 3A), wherein greater weights are assigned for narrower windows; (v) the amplitude of the signal associated with the corresponding clusters; (vi) the frequency of the signal associated with the corresponding clusters; and (vii) the width of a spatial window defining the cluster (in embodiments in which the coordinate system is continuous). For any of the cluster properties, except properties (i) and (ii), one or more statistical observables of the property, such as, but not limited to, average, median, supremum, infimum and variance over the cluster are preferably used.

For a group BNA pattern or an unassociated subject-specific BNA pattern, the connectivity weight preferably equals the weight index WI as calculated based on the cluster properties.

For an associated subject-specific BNA pattern, the connectivity weight of a pair of nodes is preferably assigned based on the weight index WI as well as one or more subject-specific and pair-specific quantities denoted SI. Representative examples of such quantities are provided below.

In various exemplary embodiments of the invention a pair of nodes of the associated subject-specific BNA pattern is assigned with a connectivity weight which is calculated by combining WI with SI. For example, the connectivity weight of a pair in the associated subject-specific BNA pattern can be given by WI·SI. When more than one quantities (say N quantities) are calculated for a given pair of nodes, the pair can be assigned with more than one connectivity weights, e.g., WI·SI$_1$, WI·SI$_2$, ..., WI·SI$_N$, wherein SI$_1$, SI$_2$, ..., SI$_N$, are N calculated quantities. Alternatively or additionally, all connectivity weights of a given pair can be combined, e.g., by averaging, multiplying and the like.

The quantity SI can be, for example, a statistical score characterizing the relation between the subject-specific pair and the corresponding clusters. The statistical score can be of any type, including, without limitation, deviation from average, absolute deviation, standard-score and the like. The relation for whom the statistical score is calculated can pertain to one or more properties used for calculating the weight index WI, including, without limitation, latency, latency difference, amplitude, frequency and the like.

A statistical score pertaining to latency or latency difference is referred to herein as a synchronization score and denoted SIs. Thus, a synchronization score according to some embodiments of the present invention can be obtained by calculating a statistical score for (i) the latency of the point as obtained for the subject (e.g., $t^{(i)}_A$ and $t^{(i)}_B$, in the above example) relative to the group-average latency of the corresponding cluster, and/or (ii) the latency difference between two points as obtained for the subject (e.g., $\Delta t^{(i)}_{AB}$), relative to the group-average latency difference between the two corresponding clusters.

A statistical score pertaining to amplitude is referred to herein as an amplitude score and denoted SIa. Thus an amplitude score according to some embodiments of the present invention is obtained by calculating a statistical score for the amplitude as obtained for the subject relative to the group-average amplitude of the corresponding cluster.

A statistical score pertaining to frequency is referred to herein as a frequency score and denoted SIf. Thus a frequency score according to some embodiments of the present invention is obtained by calculating a statistical score for the frequency as obtained for the subject relative to the group-average frequency of the corresponding cluster.

A statistical score pertaining to the location is referred to herein as a location score and denoted SIl. These embodiments are particularly useful in embodiments in which a continuous coordinate system is employed, as further detailed hereinabove. Thus a location score according to some embodiments of the present invention is obtained by calculating a statistical score for the location as obtained for the subject relative to the group-average location of the corresponding cluster.

Calculation of statistical scores pertaining to other properties is not excluded from the scope of the present invention.

Following is a description of a technique for calculating the quantity SI, according to some embodiments of the present invention.

When SI is a synchronization score SIs the calculation is optionally and preferably based on the discrete time points matching the spatiotemporal constraints set by the electrode pair (Time$_{subj}$), if such exist. In these embodiments, the times of these points can are compared to the mean and standard deviation of the times of the discrete points participating in the group pattern (Time$_{pat}$), for each region to provide a regional synchronization score SIs$_r$. The synchronization score SIs can then be calculated, for example, by averaging the regional synchronization scores of the two regions in the pair. Formally, this procedure can be written as:

$$SIs_r = 0.5 + \frac{std(Time_{pat})}{2*(abs(\overline{Time_{pat}} - Time_{subj}) + std(Time_{pat}))};$$

$$SIs = \frac{1}{r}\sum SIs_r$$

An amplitude score SIa, is optionally and preferably calculated in a similar manner. Initially the amplitude of the discrete points of the individual subject (Amp$_{subj}$) is compared to the mean and standard deviation of the amplitudes of the discrete points participating in the group pattern (Amp$_{pat}$), for each region to provide a regional amplitude score SIa$_r$. The amplitude score can then be calculated, for example, by averaging the regional amplitude scores of the two regions in the pair:

$$SIa_r = 0.5 + \frac{std(Amp_{pat})}{2*(abs(\overline{Amp_{pat}} - Amp_{subj}) + std(Amp_{pat}))};$$

$$SIa = \frac{1}{r}\sum SIa_r$$

One or more BNA pattern similarities S can then be calculated as a weighted average over the nodes of the BNA pattern, as follows:

$$Ss = \frac{\sum_i (W_i * SIs_i)}{\sum_i W_i}$$

$$Sa = \frac{\sum_i (W_i * SIa_i)}{\sum_i W_i}$$

$$Sf = \frac{\sum_i (W_i * SIf_i)}{\sum_i W_i}$$

$$Sl = \frac{\sum_i (W_i * SIl_i)}{\sum_i W_i}$$

Formally, an additional similarity, Sc, can be calculated, as follows:

$$Ic = \frac{\sum_i (W_i * SIc_i)}{\sum_i W_i},$$

where $SIc_i$ is a binary quantity which equals 1 if pair i exists in the subject's data and 0 otherwise.

In some embodiments of the present invention the quantity SI comprises a correlation value between recorded activities. In some embodiments, the correlation value describes correlation between the activities recorded for the specific subject at the two locations associated with the pair, and in some embodiments the correlation value describes correlation between the activities recorded for the specific subject at any of the locations associated with the pair and the group activities as recorded at the same location. In some embodiments, the correlation value describes causality relations between activities.

Procedures for calculating correlation values, such as causality relations, are known in the art. In some embodiments of the present invention the Granger theory is employed [Granger C W J, 1969, "Investigating Causal Relations By Econometric Models And Cross-Spectral Methods," Econometrica, 37(3):242]. Other techniques suitable for the present embodiments are found in Durka et al., 2001, "Time-frequency microstructure of event-related electroencephalogram desynchronisation and synchronisation," Medical & Biological Engineering & Computing, 39:315; Smith Bassett et al., 2006, "Small-World Brain Networks" Neuroscientist, 12:512; He et al., 2007, "Small-World Anatomical Networks in the Human Brain Revealed by Cortical Thickness from MRI," Cerebral Cortex 17:2407; and De Vico Fallani et al., "Extracting Information from Cortical Connectivity Patterns Estimated from High Resolution EEG Recordings: A Theoretical Graph Approach," Brain Topogr 19:125; the contents of all of which are hereby incorporated by reference.

The connectivity weights assigned over the BNA pattern can be calculated as a continuous variable (e.g., using a function having a continuous range), or as a discrete variable (e.g., using a function having a discrete range or using a lookup table). In any case, connectivity weights can have more than two possible values. Thus, according to various exemplary embodiments of the present invention the weighted BNA pattern has at least three, or at least four, or at least five, or at least six edges, each of which being assigned with a different connectivity weight.

In some embodiments of the present invention the method proceeds to 16 at which a feature selection procedure is applied to the BNA pattern to provide at least one sub-set of BNA pattern nodes.

Feature selection is a process by which the dimensionality of the data is reduced by selecting the best features of the input variables from a large set of candidates that are most relevant for the learning process of an algorithm. By removing irrelevant data the accuracy of representing the original features of a data set is increased thereby enhancing the accuracy of data mining tasks such as predictive modeling. Existing feature selection methods fall into two broad categories known as forward selection and backward selection. Backward selection (e.g., Marill et al., IEEE Tran Inf Theory 1963, 9:11-17; Pudil et al., Proceedings of the 12th International Conference on Pattern Recognition (1994). 279-283; and Pudil et al., Pattern Recognit Lett (1994) 15:1119-1125) starts with all the variables and removes them one by one in a step-wise fashion to be left with the top-ranked variables. Forward selection (e.g. Whitney et al., IEEE Trans Comput 197; 20:1100-1103; Benjamini et al., Gavrilov Ann Appl Stat 2009; 3:179-198) starts with an empty variable set and adds the best variable at each step until any further addition does not improve the model.

In some embodiments of the present invention a forward selection of features is employed and in some embodiments of the present invention a backward selection features is employed. In some embodiments of the present invention the method employs a procedure for controlling the fraction of false positives that may lead to poor selection, such procedure is known as false discovery rate (FDR) procedure, and is found, for example, in Benjamini et al. supra, the contents of which are hereby incorporated by reference.

A representative example of a feature selection procedure suitable for the present embodiments is illustrated in FIG. 33. Initially, a group of subjects is considered (for example, either healthy controls or diseased subjects), optionally and preferably using a sufficiently large dataset to as to provide relatively high accuracy in representing the group. The group can be represented using a BNA pattern. The feature selection procedure is then applied on a training set of the dataset in order to evaluate each feature characterizing the group's dataset, wherein the evaluated feature can be a node of the BNA pattern or a pair of nodes of the BNA pair pattern or any combinations of nodes of the BNA pattern. The input to the feature selection algorithm is preferably evaluation scores (e.g., the score for each participant in the training set on each of the features) calculated using the training set. Feature selection can also be applied, on other features, such as, but not limited to, EEG and ERP features such as, but not limited to, coherence, correlation, timing and amplitude measures. Feature selection can also be applied on different combinations of these features.

The outcome of this procedure can be a set of supervised BNA patterns (denoted "supervised networks" in FIG. 33), each suitable to describe a different sub-group of the population with a specific set of features. The supervised BNA patterns obtained during the procedure can allow a comparison of the BNA pattern obtained for a single subject to a specific network or networks. Thus, the supervised BNA patterns can serve as biomarkers.

Once the BNA pattern is constructed it can be transmitted to a display device such as a computer monitor, or a printer.

Alternatively or additionally, the BNA pattern can be transmitted to a computer-readable medium.

The method ends at 15.

FIG. 4 is a flowchart diagram describing a method suitable for analyzing a subject-specific BNA pattern, according to various exemplary embodiments of the present invention. The method begins at 50 and continues to 51 at which a BNA pattern, more preferably a weighted BNA pattern, of the subject is obtained, for example, by following the operations described above with reference to FIGS. 1, 2 and 3A-E. The BNA pattern obtained at 51 is referred to below as BNA pattern 20. BNA pattern 20 can be displayed on a display device such as a computer monitor, printed, and/or stored in a computer-readable medium, as desired.

In various exemplary embodiments of the invention BNA pattern 20 is an associated subject-specific BNA pattern, constructed based on relations between the data of the subject to group data represented by a previously annotated BNA pattern. The previously annotated BNA pattern can optionally and preferably be an entry in a database of previously annotated BNA patterns, in which case the method preferably obtains an associated subject-specific BNA pattern for each BNA pattern of the database.

The term "annotated BNA pattern" refers to a BNA pattern which is associated with annotation information. The annotation information can be stored separately from the BNA pattern (e.g., in a separate file on a computer readable medium). The annotation information is preferably global annotation wherein the entire BNA pattern is identified as corresponding to a specific brain related disorder or condition. Thus, for example, the annotation information can pertain to the presence, absence or level of the specific disorder, condition or brain function. Also contemplated are embodiments in which the annotation information pertains to a specific brain related disorder or condition in relation to a treatment applied to the subject. For example, a BNA pattern can be annotated as corresponding to a treated brain related disorder. Such BNA pattern can also be annotated with the characteristics of the treatment, including dosage, duration, and elapsed time following the treatment. A BNA pattern can optionally and preferably be annotated as corresponding to an untreated brain related disorder.

As used herein, the term "treatment" includes abrogating, substantially inhibiting, slowing or reversing the progression of a condition, substantially ameliorating clinical or aesthetical symptoms of a condition or substantially preventing the appearance of clinical or aesthetical symptoms of a condition. Treatment can include any type of intervention, both invasive and noninvasive, including, without limitation, pharmacological, surgical, irradiative, rehabilitative, and the like.

Alternatively or additionally, the BNA pattern can be identified as corresponding to a specific group of individuals (e.g., a specific gender, ethnic origin, age group, etc.), wherein the annotation information pertains to the characteristics of this group of individuals. In some embodiments of the present invention the annotation information includes local annotation wherein nodes at several locations over the BNA pattern are identified as indicative of specific disorder, condition and/or group.

The method proceeds to 52 at which BNA pattern 20 is compared to the previously annotated BNA pattern. In embodiments in which several subject-specific BNA patterns are obtained for the same subject, each of the subject-specific BNA patterns are preferably compared to the corresponding annotated BNA pattern. The method optionally and preferably selects the pair of BNA patterns which best match each other. Optionally, the method can assign a score to each pair of BNA patterns being compared. Such score can be, for example, one or more BNA pattern similarity S, as further detailed hereinabove. Thus, in various exemplary embodiments of the invention 52 includes calculation of at least one BNA pattern similarity S, describing the similarity between BNA pattern 20 and the previously annotated BNA pattern.

In various exemplary embodiments of the invention BNA pattern 20 is compared to at least one BNA pattern annotated as abnormal, and at least one BNA pattern annotated as normal. A BNA pattern annotated as abnormal is a BNA pattern which is associated with annotation information pertaining to the presence, absence or level of a brain related disorder or condition. A BNA pattern annotated as normal is a BNA pattern which was extracted from a subject, or more preferably, a group of subjects, identified as having normal brain function. Comparison to a BNA pattern annotated as abnormal and a BNA pattern annotated as normal is useful for classifying BNA pattern 20 according to the respective brain related disorder or condition. Such classification is optionally and preferably provided by means of likelihood values expressed using similarities between a subject-specific BNA pattern and a group BNA pattern.

A subject-specific BNA pattern can be classified according to any of the aforementioned brain related disorder or conditions.

The previously annotated BNA pattern can optionally and preferably be a baseline annotated BNA pattern characterizing a group of subjects identified as having normal brain function or having the same brain disorder. Such baseline annotated BNA pattern is optionally larger than BNA pattern 20 in terms of the order (namely the number of nodes in the BNA pattern) and and/or size of (namely the number of edges in the BNA pattern). Representative examples of baseline BNA patterns and techniques for constructing and annotating such baseline BNA patterns are described in the Examples section that follows.

The comparison between BNA patterns, according to some embodiments of the present invention is preferably quantitative. In these embodiments the comparison between the BNA patterns comprises calculating BNA pattern similarity. The BNA pattern similarity is optionally and preferably calculated based on the values of the connectivity weights of the BNA patterns. For example, BNA pattern similarity can be obtained by averaging the connectivity weights over the subject-specific BNA pattern. When more than one type of connectivity weight is assigned for each pair of nodes in BNA pattern 20, the averaging is preferably performed over the BNA pattern separately for each type of connectivity weight. Optionally and preferably one or more of the averages can be combined (e.g., summed, multiplied, averaged, etc.) to provide a combined BNA pattern similarity. Alternatively, a representative of the averages (e.g., the largest) can be defined as the BNA pattern similarity.

The BNA pattern similarity can be used as a classification score which describes, quantitatively, the membership level of the subject to the respective group. This embodiment is particularly useful when more than one subject-specific BNA patterns are constructed for the same subject using different group data, wherein the classification score can be used to assess the membership level of the subject to each of the groups.

The similarity can be expressed as a continuous or discrete variable. In various exemplary embodiments of the invention the similarity is a non-binary number. In other words, rather than determining whether the two BNA patterns are similar or dissimilar, the method calculates the degree by which the two BNA patterns are similar or dissimilar. For example, the similarity can be expressed as percentage, as a non-integer number between 0 and 1 (e.g., 0 corresponding to complete dissimilarity and 1 corresponding to comparison between a BNA pattern and itself), and the like.

The above procedure for calculating the similarity can be performed both for the comparison between the subject-specific BNA pattern 20 and a BNA pattern annotated as abnormal, and for the comparison between the subject-specific BNA pattern 20 and a BNA pattern annotated as normal.

The comparison between the subject's BNA pattern and the reference BNA pattern is optionally and preferably with respect to the supervised BNA patterns obtained during the feature selection procedure (see, for example, FIG. 33).

Several comparison protocols are contemplated, and are schematically illustrated in FIGS. 34A-C. These comparison protocols are particularly useful to construct a single subject BNA pattern that can be used as a baseline against which the subject can be scored across multiple tests. The advantage of such baseline is that variability among data obtained within the subject is typically smaller than the variability between subjects. Thus, according to some embodiments of the present invention the BNA pattern of the subject is compared to a BNA pattern that corresponds to the same subject.

In the comparison illustrated in FIG. 34A, a matching process that allows quantifying the degree of similarity between the brain activity of the single subject and that represented by the BNA pattern(s) of the group is employed. The overall degree of similarity can be quantified, according to some embodiments of the present invention, by a score which is a weighted sum of the separated similarity scores associated with all of the compared features. In embodiments in which several BNA patterns are obtained, each BNA pattern characterizes a specific sub-group in the population. In these embodiments, the subject can be matched against a BNA pattern or BNA patterns associated with a sub-group that most resemble the characteristics of the subject.

In the comparison illustrated in FIG. 34B, the BNA pattern of the subject is compared against the group BNA pattern and representative matching features (e.g., best matching features) of the single subject to those of the group network are preferably selected. These representative matching features can be used as an approximation of the intersection between the single-subject BNA pattern and the group BNA pattern and constitute a personalized single-subject BNA sub-pattern that serves as a reference baseline used in multiple tests of the same subject.

In some embodiments, the single subject may be compared against several group BNA sub-pattern describing homogeneous subtypes enabling fine-tuning in choosing a single subject BNA pattern that can serve as a reference. Thus, matching individual features to the features of the group's BNA pattern allows the extraction of a customized BNA pattern and a comparison of the individual to a sub-set of features most characterizing their condition (e.g., healthy, diseased).

In the comparison illustrated in FIG. 34C, various combination of comparisons are shown. These include, but are not limited to, single subject BNA pattern against another single subject BNA pattern, BNA pattern against the intersection between the BNA pattern and the single subject BNA pattern, and the like.

At 53 the method extracts information pertaining to the condition of the subject, responsively to the comparison between BNA pattern 20 and the annotated BNA pattern(s). Once the information is extracted, it can be transmitted to a computer-readable medium or a display device or a printing device, as desired. Many types of information are contemplated by the present inventors. Representative examples of such types are further detailed hereinbelow.

The method ends at 54.

In various exemplary embodiments of the invention, the extracted information pertains to the likelihood of abnormal brain function for the subject. Additionally, the BNA pattern comparison can optionally and preferably be used for extracting prognostic information. For example, BNA pattern 20 can be compared to a baseline annotated BNA pattern that characterizes a group of subject all suffering from the same abnormal brain function with similar rehabilitation history, wherein the baseline annotated BNA pattern is constructed from neurophysiological data acquired at the beginning of the rehabilitation process. The similarity level between BNA pattern 20 and that baseline annotated BNA pattern can be used as a prognosis indicator for the particular abnormal brain function and the particular rehabilitation process.

The likelihood of abnormal brain function is optionally and preferably extracted by determining a brain-disorder index based, at least in part, on the similarity between BNA pattern 20 and the annotated BNA pattern(s). For example, when a similarity between BNA pattern 20 and a BNA pattern annotated as corresponding to ADHD is calculated, the similarity can be used for calculating an ADHD index. The brain-disorder index can be the similarity itself or it can be calculated based on the similarity.

In various exemplary embodiments of the invention the brain-disorder index is calculated based on the similarity between BNA pattern 20 and a BNA pattern annotated as abnormal, as well as the similarity between BNA pattern 20 and a BNA pattern annotated as normal. For example, denoting the former similarity by $S_{abnormal}$ and the latter similarity by $S_{normal}$, where both $S_{abnormal}$ and $S_{normal}$ are between 0 and 1, the brain-disorder index $I_{disorder}$ can be calculated as:

$$I_{disorder} = (S_{abnormal} + (1 - S_{normal}))/2.$$

Variations of the above formula are not excluded from the scope of the present invention.

A representative example for a process for determining a brain-disorder index for the case of an ADHD is illustrated in FIGS. 5A-F, showing BNA patterns constructed from EEG data. In FIGS. 5A-F, red nodes correspond to ERP at the Delta frequency band, green nodes correspond to ERP at the Theta frequency band, and yellow nodes correspond to ERP at the Alpha frequency band. The BNA patterns also include nodes corresponding to locations where ERPs at more than one frequency band have been recorded. These nodes are shown as mixed colors. Specifically, green-red nodes correspond to ERP at the Delta and Theta frequency bands, and yellow-green nodes correspond to ERP at the Alpha and Theta frequency bands.

FIG. 5A shows a baseline BNA pattern annotated as normal, and FIG. 5D shows a baseline BNA pattern annotated as corresponding to ADHD. Each of these two BNA patterns was constructed from a group of adult subject identified as normal and having ADHD, respectively. As shown in FIG. 5A the baseline BNA pattern for normal brain function has nodes that represent ERPs, predominantly at the delta frequency band (red nodes), at a plurality of frontal-posterior locations at the right hemisphere. The characteristic time window of the delta nodes has a width of about 50 ms. The characteristic latencies of the delta nodes are, on the average, about 90-110 ms and about 270-330 ms. As shown in FIG. 5D the baseline BNA pattern for ADHD has nodes that represent ERPs, predominantly at the theta and alpha frequency bands (green and yellow nodes), at a plurality of frontocentral locations. The BNA pattern for ADHD may also include nodes in the central-parietal locations. The characteristic time window $\Delta t_A$ of the theta and alpha nodes is from about 100 ms to about 200 ms.

FIGS. 5B and 5E show associated subject-specific BNA patterns constructed based on comparison to the normal and ADHD baseline group BNA patterns, respectively. The similarity values, calculated as described above, are $S_{normal}$=0.76 (FIG. 5B) and $S_{ADHD}$=0.47 (FIG. 5E). Thus the BNA pattern of this subject is more similar to the normal baseline BNA pattern than to the ADHD baseline BNA pattern. The ADHD index of this subject can be set to 0.47, or, more preferably, (0.47+(1−0.76))/2=0.355.

FIGS. 5C and 5F show the results of a comparison between a subject-specific BNA pattern (constructed for another single subject) to the normal and ADHD baseline BNA patterns, respectively. The similarity values, calculated as described above, are $S_{normal}$=0.32 (FIG. 5C) and $S_{ADHD}$=0.68 (FIG. 5F). Thus the BNA pattern of this subject is more similar to the ADHD baseline BNA pattern than to the normal baseline BNA pattern, and the ADHD index of this subject can be set to 0.68, or, more preferably, (0.68+(1−0.32))/2=0.68.

The brain-disorder index can be presented to the user graphically on a scale-bar. A representative example of such graphical presentation for the case of ADHD is shown in FIG. 11.

While the embodiments above were described with a particular emphasis to ADHD, it is to be understood that more detailed reference to this disorder is not to be interpreted as limiting the scope of the invention in any way. Thus, the BNA pattern comparison technique can be used for assessing likelihood of many brain related disorders, including any of the aforementioned brain related disorders. Further examples regarding the assessment of likelihood of brain related disorders are provided in the Examples section that follows (see Example 1 for ADHD and Example 5 for Mild Cognitive Impairment and Alzheimer's Disease).

A baseline annotated BNA pattern can also be associated with annotation information pertaining to a specific brain related disorder or condition of a group of subjects in relation to a treatment applied to the subjects in the group. Such baseline BNA pattern can also be annotated with the characteristics of the treatment, including dosage, duration, and elapsed time following the treatment. A comparison of BNA pattern 20 to such type of baseline BNA patterns, can provide information regarding the responsiveness of the subject to treatment and/or the efficiency of the treatment for that particular subject. Such comparison can optionally and preferably be used for extracting prognostic information in connection to the specific treatment. A BNA pattern that is complementary to such baseline BNA pattern is a BNA pattern that is annotated as corresponding to an untreated brain related disorder.

Optionally and preferably, the method compares BNA pattern 20 to at least one baseline BNA pattern annotated as corresponding to a treated brain related disorder, and at least one baseline BNA pattern annotated as corresponding to an untreated brain related disorder. Representative examples for a process for assessing the responsiveness of a subject to treatment using such two baseline BNA patterns is illustrated in FIGS. 6A-F, 7A-D and 8A-E.

Figure 6A:
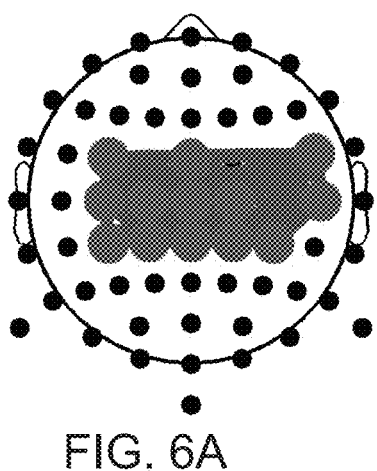
Figure 6B:
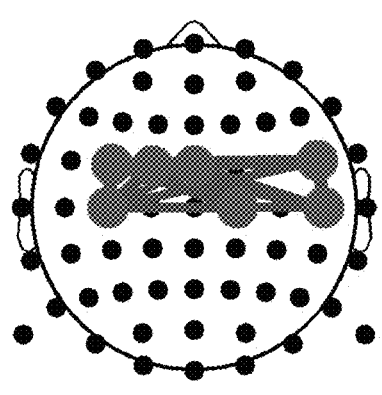
Figure 6C:
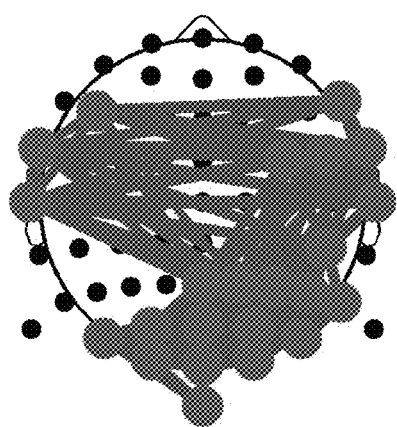
Figure 6D:
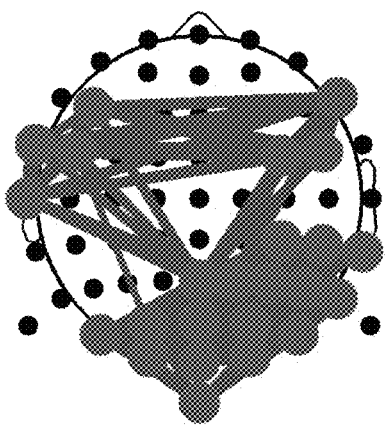

The BNA patterns shown in FIGS. 6A-D are associated subject-specific BNA patterns constructed from EEG data recorded from a particular ADHD subject. The black dots in FIGS. 6A-D show the locations of the EEG electrodes. The color codes in these BNA patterns are the same as defined above. The subject-specific BNA patterns shown in FIGS. 6A-B describe the association of the ADHD subject to a group of untreated ADHD subjects, and the BNA patterns shown in FIGS. 6C-D describe the association of the ADHD subject to a group of ADHD subjects all treated with methylphenidate (MPH). The subject-specific BNA patterns shown in FIGS. 6A and 6C are based on EEG data recorded from the ADHD subject before any treatment, and subject-specific BNA patterns shown in FIGS. 6B and 6D are based on EEG data recorded from the ADHD subject following a treatment with MPH.

Figure 6E:
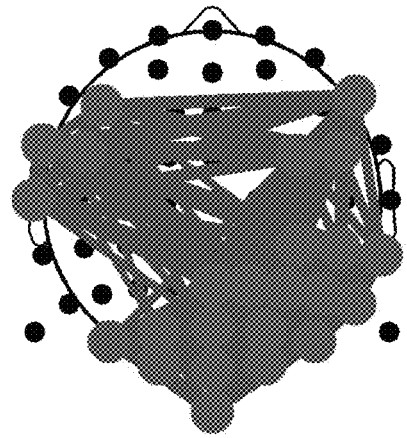
Figure 6F:
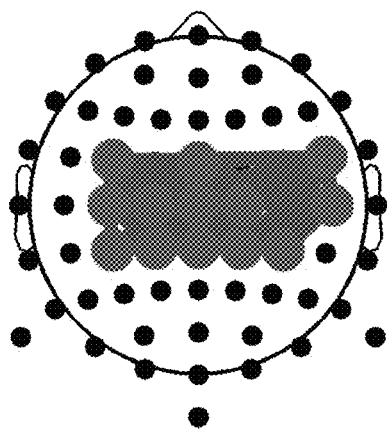

The baseline annotated BNA pattern constructed from the group of untreated ADHD subjects, and the baseline annotated BNA pattern constructed from the same group of subjects, but following treatment with MPH are shown in FIGS. 6E and 6F, respectively.

A BNA pattern similarity was calculated for each of the subject-specific BNA patterns shown in FIGS. 6A-D. The calculated similarity corresponding to the BNA pattern of FIG. 6A is 0.73, the calculated similarity corresponding to the BNA pattern of FIG. 6B is 0.19, the calculated similarity corresponding to the BNA pattern of FIG. 6C is 0.56, and the calculated similarity corresponding to the BNA pattern of FIG. 6D is 0.6. It is recognized by the present inventors that these similarity values indicate that the subject is responsive to the treatment. Before treatment, the subject's BNA pattern had a relatively high similarity (0.73) to the baseline BNA pattern for the group of untreated ADHD subjects and a relatively low similarity (0.56) to the baseline BNA pattern for the group of treated ADHD subjects, meaning that this subject can be classified with that the group of untreated ADHD subjects. Following a single dose treatment with MPH, the similarity value to the baseline BNA pattern for untreated ADHD group was scientifically reduced from 0.73 to 0.19, while the similarity value to the baseline BNA pattern for the treated ADHD group was increased from 0.56 to 0.6, meaning that after treatment a single dose, the subject's brain activity no longer has the characteristics of untreated ADHD activity, but rather has the characteristics of treated ADHD activity.

Some results of the MPH study for ADHD subjects are summarized in FIG. 12. For each subject, two associated subject-specific BNA patterns were constructed. A first BNA pattern described the association of the subject to a group of untreated ADHD subjects, and a second BNA pattern described the association of the subject to a group of healthy subjects (control). The left bar shows average score for subjects before treatment with MPH, the middle bar shows average score for subjects after treatment with MPH, and the rightmost bar shows the score of the control group.

A representative example of the evolution of the group BNA patterns over time is shown in FIG. 13. Shown in FIG. 13 are three columns of BNA patterns, corresponding to the groups of untreated ADHD subjects (left column), ADHD subjects following treatment with MPH (middle column), and control (right column). The evolution is shown at intervals of 50 ms. The topmost BNA pattern at each column is formed by a superposition of the other patterns in that column.

Further details regarding analysis of neurophysiological data acquired from ADHD subjects are provided in the Examples section that follows (see Example 1).

The BNA pattern technique of the present embodiments can also be used for determining a recommended dose for the subject. Specifically, the dose can be varied until a sufficiently high or maximal similarity to the baseline BNA pattern for treated subjects is obtained. Once such similarity is achieved, the method can determine that the dose achieving such similarity is the recommended dose for this subject.

Figure 7A:
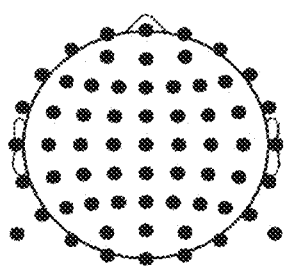
Figure 7B:
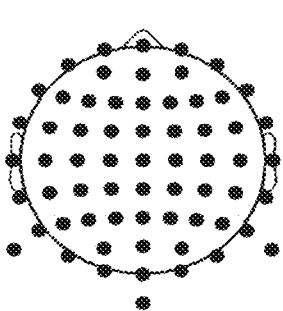
Figure 7C:
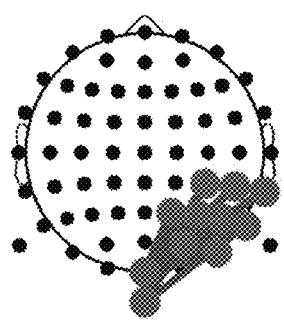
Figure 7D:
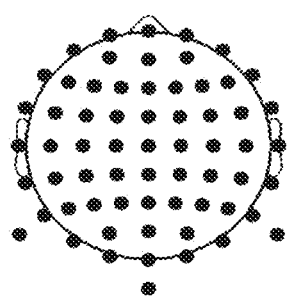

The BNA patterns shown in FIGS. 7A-D were constructed from EEG data recorded from a different ADHD subject, which was also treated with MPH according to the same protocol as described above with respect to the responder subject of FIGS. 6A-D. The black dots in FIGS. 7A-D show the locations of the EEG electrodes, and the color codes in these BNA patterns is the same as defined above. Thus, the subject-specific BNA patterns shown in FIGS. 7A-B describe the association of the ADHD subject to a group of untreated ADHD subjects, and the BNA patterns shown in FIGS. 7C-D describe the association of the ADHD subject to a group of ADHD subjects all treated with methylphenidate (MPH). The subject-specific BNA patterns shown in FIGS. 7A and 7C are based on EEG data recorded from the ADHD subject before any treatment, and subject-specific BNA patterns shown in FIGS. 7B and 7D are based on EEG data recorded from the ADHD subject following a treatment with MPH.

Note that the BNA patterns of FIGS. 7A and 7D do not include any nodes and edges. This, however, does not mean that the subjects had no brain activity. A void associated subject-specific BNA pattern means that none of data features of the respective subject was member of a cluster in the group to which the subject is attempted to be associated with.

A BNA pattern similarity was calculated for each of the subject-specific BNA patterns shown in FIGS. 7A-D. The calculated similarity corresponding to the BNA pattern of FIG. 7A is 0, the calculated similarity corresponding to the BNA pattern of FIG. 7B is 0, the calculated similarity corresponding to the BNA pattern of FIG. 7C is 0.06, and the calculated similarity corresponding to the BNA pattern of FIG. 7D is 0. It is recognized by the present inventors that these similarity values indicate that the subject is not responsive to the treatment.

FIGS. 8A-D show associated subject-specific BNA patterns constructed from EEG data recorded from two healthy volunteer subjects. The black dots in FIGS. 8A-D show the locations of the EEG electrodes, and the color codes in these BNA patterns are the same as defined above. The subject-specific BNA patterns shown in FIGS. 8A-D describe the association of the subjects to a group of healthy subjects following treatment with a placebo drug and while performing an attention task related oddball task. The baseline annotated BNA pattern of this group is shown in FIG. 8E.

Figure 8A:
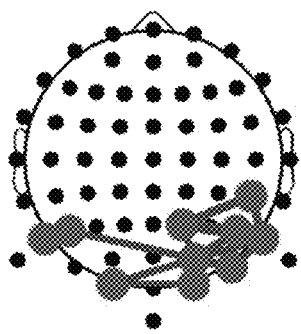
Figure 8B:
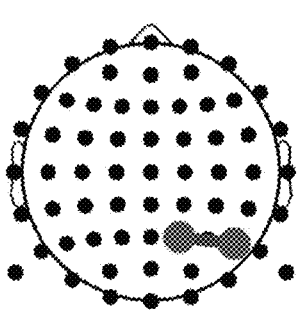
Figure 8C:
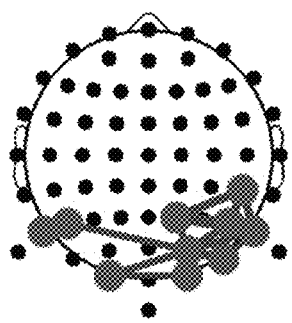
Figure 8D:
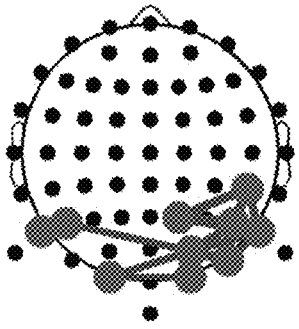
Figure 8E:
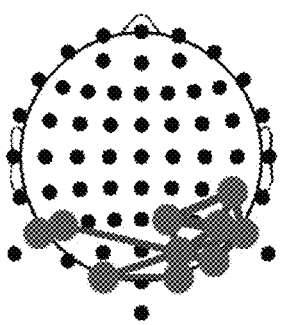

FIGS. 8A and 8C are subject-specific BNA patterns constructed from EEG data collected from a first subject (FIG. 8A) and a second subject (FIG. 8C) following treatment with a placebo, and FIGS. 8B and 8D are subject-specific BNA patterns constructed from EEG data collected from the first subject (FIG. 8B) and the second subject (FIG. 8D) following treatment with a scopolamine drug. Scopolamine is an anticholinergic drug with inhibitory effect on M2-cholinergic receptors of excited type. It has an inhibitory effect on the cerebral cortex, typically inducing slight-anesthetic effect.

A BNA pattern similarity was calculated for each of the subject-specific BNA patterns shown in FIGS. 8A-D. The calculated similarities are 0.937, 0.079, 1.0 and 0.94, respectively. It is recognized by the present inventors that these similarity values indicate that the responsivity to scopolamine is high for the first subject (FIGS. 8A and 8B) and low for the second subject (FIGS. 8C and 8D). These conclusions were also confirmed in clinical observations wherein, following treatment with the scopolamine, a 70% decrease in behavioral endpoint was observed for the first subject, but no change in behavioral endpoint was observed for the second subject.

Further details regarding analysis of neurophysiological data acquired from subjects administered with scopolamine are provided in the Examples section that follows (see Example 4).

The above examples demonstrate that the BNA pattern comparison technique of the present embodiments can be used for quantitative assessment of the responsivity to treatment. While the embodiments above were described with a particular emphasis to treatments with MPH and scopolamine, it is to be understood that more detailed reference to these treatments is not to be interpreted as limiting the scope of the invention in any way. Thus, the BNA pattern comparison technique can be used for assessing responsiveness to and efficacy of many types of treatments.

In various exemplary embodiments of the invention, the extracted information pertains to the level of pain the subject is experiencing. Preferably, the information includes an objective pain level. Pain level assessment according to some embodiments of the present invention is particularly useful in institutions that provide treatment or rehabilitation for subjects suffering from chronic pain. A representative example for the use of BNA pattern for measuring pain is illustrated in FIGS. 9A and 9B, showing BNA patterns constructed from EEG data during a pain study which is further detailed in the Examples sections that follows (see Example 3). FIG. 9A is a subject-specific BNA pattern constructed from a subject who declared that the pain was relatively high, and FIG. 9B is a subject-specific BNA pattern constructed from a subject who declared that the pain was relatively low. As shown, the difference in pain level is expressed in the BNA patterns, wherein for subjects experiencing low pain the size of the BNA pattern is smaller than for subjects experiencing high pain. Thus, the size of the BNA pattern can be used as an indicator for the level of pain.

In some embodiments of the present invention BNA pattern 20 is compared to a BNA pattern constructed for the same subjects at a different time. These embodiments are useful for many applications.

For example, in some embodiments, the comparison is used for determining presence, absence and/or level of neural plasticity in the brain.

Brain plasticity relates to the ability of the brain to adapt (functionally and/or structurally) to changed conditions, sometimes after injury or strokes, but more commonly in acquiring new skills. Brain plasticity has been demonstrated in many basic tasks, with evidence pointing to physical modifications in the cortex during repetitive performance. The plasticity of neural interactions resulting from repetitive performance of specific tasks is known to lead to improved performance.

Determination of neural plasticity is particularly useful for subjects suffering a stroke, wherein part of the brain is damaged and other parts begin to function or change their function. A comparison between two BNA's of a subject after a stroke can be used to identify a change in brain activity hence also to assess neural plasticity in the brain. In some embodiments of the present invention a late stage BNA pattern is constructed for a subject during the subject's rehabilitation. A late stage BNA pattern is optionally from data acquired during several rehabilitation sessions, preferably at a sufficiently advanced stage of the rehabilitation. Such BNA pattern can be viewed as a neural network pathway achieved by the brain in order to overcome motor dysfunction. A subject-specific BNA pattern, constructed during an individual session can then be compared to the late stage BNA pattern, thereby establishing a learning curve for the subject.

Determination of neural plasticity is particularly useful for subjects suffering from chronic pain. It is recognized by the present inventors that, the presence of chronic pain is perceived and established in the brain, and is oftentimes accompanied by chemical changes in the brain. For example, there is a decrease in N-acetyl aspartate and changes in other brain metabolites. The chemical changes result in depression, anxiety and/or a loss of cognitive memory functions. A comparison between two BNA's of the subject can be used to identify a change in brain activity hence also to assess those chemical changes. Such assessment can be used, for example, in combination with a pain stimulus, to determine the likelihood that the subject is a chronic pain sufferer or having normal response to the pain stimulus.

In some embodiments, a BNA pattern constructed from neurophysiological data acquired following a treatment is compared to a BNA pattern constructed from neurophysiological data acquired before a treatment. Such comparison can be used for assessing responsiveness to and optionally efficacy of the treatment. This can be done generally as described above with respect to FIGS. 6A-D, 7A-D and 8A-D, except that the comparisons are between two BNA patterns of the same subject instead of between a BNA pattern of the subject and a baseline BNA pattern of a group.

In some embodiments, a BNA pattern constructed from neurophysiological data acquired while the subject performs a particular task is compared to a BNA pattern constructed from neurophysiological data acquired while the subject is not performing the particular task and/or while the subject performs another particular task. A representative example for these embodiments will now be described with reference to FIGS. 10A-H.

FIGS. 10A-H show group BNA patterns constructed from EEG data recorded from two groups of subjects during a working memory test. The black dots in FIGS. 10A-H show the locations of the EEG electrodes, and the color codes in these BNA patterns is the same as defined above. During the test, each subject of the group was asked to memorize an image of a human face (referred to as the "cue"). Two seconds later, the subject was again presented with an image of a human face (referred to as the "probe") and was asked to determine whether the probe matches the cue.

Figure 10E:
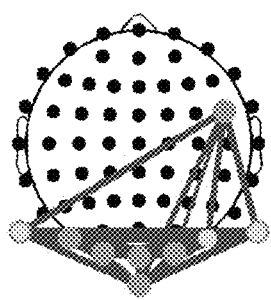
Figure 10F:
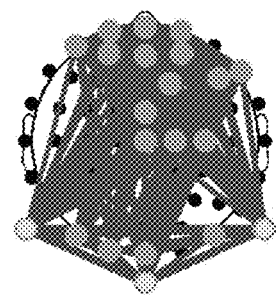
Figure 10G:
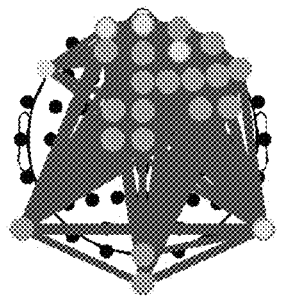
Figure 10H:
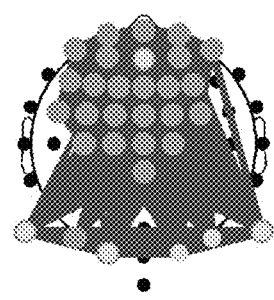

The BNA patterns of the first group are shown in FIGS. 10A-D. FIGS. 10A and 10B are group BNA patterns constructed following treatment with a placebo (referred to below as placebo A), and FIGS. 10C and 10D are group BNA patterns constructed following treatment with a Scopolamine. The BNA patterns of the second group are shown in FIGS. 10E-H, where FIGS. 10E and 10F are group BNA patterns constructed following treatment with a placebo (referred to below as placebo B), and FIGS. 10G and 10H are BNA patterns constructed following treatment with a Ketamine.

The effect of scopolamine is explained above. Ketamine is widely recognized as a general nonbarbiturate anesthetic that acts quickly to produce an anesthetic state. More specifically, ketamine is an acrylcycloalkylamine used traditionally in the induction of dissociative anesthesia. Ketamine has been used to induce anesthesia prior to elective surgery in healthy children, and also to induce anesthesia in elderly subjects who could not tolerate general anesthesia.

The BNA pattern of FIGS. 10A, 10C, 10E and 10G were constructed from the data acquired during the time at which the cue was presented and are recognized by the present inventor as containing information pertaining to the memorization process in the brain (also known in the literature as "encoding"). The BNA patterns of FIGS. 10B, 10D, 10F and 10H were constructed from the data acquired during the time at which the probe was presented, and are recognized by the present inventor as containing information pertaining to the retrieval process in the brain. It is noted that the BNA patterns of FIGS. 10A-H describe differentiating activity networks. Thus, for example, the BNA pattern of FIG. 10A describes the brain activity during cue that most differentiated between placebo A and Scopolamine, and the BNA pattern of FIG. 10B describes the brain activity during cue that most differentiated between placebo B and Ketamine.

As shown in FIGS. 10A-B and 10E-F, following treatment with placebo, the BNA pattern during retrieval is substantially larger in both the order and the size than the BNA pattern during memorization. The situation is different following treatment with Scopolamine and Ketamine. The scopolamine (FIGS. 10C-D) induced (i) low connectivity between frontal and parietal regions, and (ii) extensive compensatory central and frontal activation. The ketamine (FIGS. 10G-H) induced increased central and frontal activation, and decreased right lateralization. No significant change in the fronto-parietal part of the BNA pattern was observed.

Further details regarding analysis of neurophysiological data acquired from subjects administered with scopolamine are provided in the Examples section that follows (see Example 4).

The BNA pattern comparison technique of the present embodiments can also be used for inducing improvement in brain function. In some embodiments of the present invention associated subject-specific BNA patterns are constructed for a subject during a higher-level cognitive test, generally in real time. The subject can be presented with the constructed BNA patterns or some representation thereof and use them as a feedback. For example, when, as a result of the cognitive action, the BNA pattern of the subject becomes more similar to a characteristic BNA pattern of a healthy group, presentation of such a result to the subject can be used by the subject as a positive feedback. Conversely, when, as a result of the cognitive action, the BNA pattern of the subject becomes more similar to a characteristic BNA pattern of a brain-disorder group, presentation of such a result to the subject can be used by the subject as a negative feedback. Real time analysis of BNA patterns in conjunction with neurofeedback can optionally and preferably be utilized to achieve improved cortical stimulation using external stimulating electrodes.

The BNA pattern comparison technique of the present embodiments can also be used for assessing responsiveness to and optionally efficacy of a phototherapy. Phototherapy is the application of light energy to biological tissue for the purpose of stimulating certain biological functions, such as natural tissue healing and regrowth processes. Alternatively, a higher power level of phototherapy may inhibit natural biological functions of the tissue or destroy the tissue, as may be applied in the case of cancerous tissue.

Generally, phototherapy is accomplished by radiating light energy into a subject's tissue at or below the skin or surface of the tissue. The radiation is applied at wavelengths either in the visible range or the invisible infrared (IR) range. Phototherapy may also be accomplished by applying coherent and non-coherent light energy, laser and non-laser light energy, and narrow and broadband light energy, in either a continuous or pulsed manner. The radiation energy is also typically applied at a low power intensity, typically measured in milliwatts. The relatively low radiation energy applied in therapy is called low level light therapy (LLLT). LLLT has also been suggested for neurological disorders in the CNS, for the prevention and/or repair of damage, relief of symptoms, slowing of disease progression, and correction of genetic abnormalities. In particular, phototherapy can be used following a cerebrovascular accident (stroke).

The present embodiments can be used for assessing the responsiveness to and optionally the efficacy of phototherapy, particularly LLLT of neurological disorders. Such assessment can be done by constructing BNA patterns from neurophysiological data acquired before, after and optionally during phototherapy and comparing those BNA patterns among themselves and/or to baseline BNA pattern as further detailed hereinabove.

The BNA pattern comparison technique of the present embodiments can also be used for assessing responsiveness to and optionally efficacy of hyperbaric therapy. Hyperbaric therapy is indicated for many medical conditions, therapeutic purposes, and training regimens. Hyperbaric treatment can aid in the treatment of many oxygen dependent diseases as well as sports injuries. Some of the ailments that can be effectively treated by hyperbaric therapy include: cerebral edema, traumatic head and spinal cord injury, chronic stroke, post stroke, early organic brain syndrome, brain stem syndromes, brain ischemia, brain blood circulation disturbances and headache disorder. Typically, treatment in a hyperbaric chamber is provided by administering oxygen to the user via a closed-circuit mask, hood, or other device while a hyperbaric chamber is maintained at pressures above ambient pressure. The oxygen is supplied to the user from a supply source external to the chamber. The subject exhales through a closed system back outside the chamber such that the ambient air in the chamber remains less than 23.5% oxygen or is not oxygen enriched. The environment within the chamber is also generally maintained by a source external to the chamber and is generally controlled by a thermostat.

Assessment of responsiveness to and/or efficacy of hyperbaric therapy can be done by constructing BNA patterns from neurophysiological data acquired before, after and optionally during hyperbaric therapy and comparing those BNA patterns among themselves and/or to baseline BNA pattern as further detailed hereinabove.

Additional examples of treatments which may be assessed by the BNA pattern comparison technique of the present embodiments include, without limitation, ultrasound treatment, rehabilitative treatment, and neural feedback, e.g., EMG biofeedback, EEG neurofeedback, transcranial magnetic stimulation (TMS), and direct electrode stimulation (DES).

In some embodiments of the present invention local stimulation is applied to the brain responsively to the information extracted from the BNA comparison. The local stimulation is optionally and preferably at one or more locations corresponding to a spatial location of at least one of the nodes of the BNA pattern. Operations 51, 52 and 53 of the method can be executed repeatedly, and the local stimulation can be varied according to some embodiments of the present invention responsively to variations in the extracted information. Thus, the stimulation and BNA pattern analysis can be employed in a closed loop, wherein the BNA pattern analysis can provide indication regarding the effectiveness of the treatment. The closed loop can be realized within a single session with the subject, e.g., while the electrodes that are used to collect the data from the brain and the system that is used for applying the stimulation engage the head of the subject. Any of the aforementioned types of local stimulations can be employed.

A representative example of application of local stimulation is in the case of pain. In these embodiments the local stimulation is applied to reduce or eliminate the pain. Thus, the BNA pattern can be analyzed to identify nodes that correspond to pain, and the stimulation can be applied to locations that correspond to these nodes.

In some embodiments, a pain stimulus (such as heat stimulus) can be applied to the subject prior to or while acquiring the neurophysiological data. The BNA pattern can be analyzed to identify nodes that correspond to the applied pain stimulus and the local stimulation can be at one or more locations corresponding to those identified nodes. These embodiments are useful particularly, but not exclusively, for situations of chronic pain (e.g., fibromyalgia).

Aside for MPH, scopolamine and ketamine described above, the BNA pattern comparison technique can be used for assessing responsiveness to and optionally efficacy of many other types of pharmacological treatments.

For example, when the subject suffers from a neurodegenerative disorder such as Alzheimer's disease, the treatment can include use of pharmacologically active agent selected from the group consisting of donepezil, physostigmine, tacrine, pharmaceutically acceptable acid addition salts thereof, and combinations of any of the foregoing; when the subject suffers from a neurodegenerative disorder such as Huntington's disease, the treatment can include use of pharmacologically active agent selected from the group consisting of fluoxetine, carbamazepine, and pharmaceutically acceptable acid addition salts and combinations thereof; when the subject suffers from a neurodegenerative disorder such as Parkinson's disease, the treatment can include use of pharmacologically active agent selected from the group consisting of amantadine, apomorphine, bromocriptine, levodopa, pergolide, ropinirole, selegiline, trihexyphenidyl, atropine, scopolamine, glycopyrrolate, pharmaceutically acceptable acid addition salts thereof, and combinations of any of the foregoing; and when the subject suffers from a neurodegenerative disorder such as amyotrophic lateral sclerosis (ALS) the treatment can include use of pharmacologically active agent selected from the group consisting of baclofen, diazepam, tizanidine, dantrolene, pharmaceutically acceptable acid addition salts thereof, and combinations of any of the foregoing.

Generally, pharmacological treatments can include use of a pharmacologically active agent, e.g., centrally acting drugs, particularly CNS active agents and other nervous system agents, including, but not limited to, the following: sympathomimetic amines; neuroprotective and neuroregenerative agents, including neurotrophic factors; neuroactive amino acids and peptides; neurotransmitters; muscarinic receptor agonists and antagonists; anticholinesterases; neuromuscular blocking agents; ganglionic stimulating drugs; agents to treat neurodegenerative disorders such as Alzheimer's disease, Huntington's disease, Parkinson's disease, and amyotrophic lateral sclerosis (ALS); anti-epileptic agents;

CNS and respiratory stimulants; and drugs that selectively modify CNS function, including anesthetic agents, analgesic agents, antiemetic agents, antihypertensive agents, cerebral vasodilators, hypnotic agents and sedatives, anxiolytics and tranquilizers, neuroleptic agents, anti-microbial agents, alpha adrenergic receptor antagonists, and appetite suppressants. Some agents, as will be appreciated by those of ordinary skill in the art, are encompassed by two or more of the aforementioned groups.

Examples of these pharmacologically active agents include, without limitation, sympathomimetic amines (e.g., include albuterol, amphetamine, benzphetamine, colterol, diethylpropion, dopamine, dopamine hydrochloride, dobutamine, ephedrine, epinephrine, epinephrine bitartrate, ethylnorepinephrine, ethylnorepinephrine hydrochloride, fenfluramine, fenoldapam, fenoldopam, fenoldopam mesylate, hydroxyamphetamine, hydroxyamphetamine hydrobromide, ibopamine, isoetharine, isoproterenol, isoproterenol hydrochloride, mephentermine, mephentermine sulfate, metaproterenol, metaraminol, metaraminol bitartrate, methoxamine, methoxamine hydrochloride, midodrine, norepinephrine, norepinephrine bitartrate, phendimetrazine, phenmetrazine, phentermine, phenylephrine, phenylephrine hydrochloride, phenylethylamine, phenylpropanolamine, prenalterol, propylhexedrine, ritodrine, terbutaline, terbutaline sulfate, and tyramine); Neuroprotective and neuroregenerative agents (e.g., excitatory amino acid antagonists and neurotrophic factors, e.g., brain derived neurotrophic factor, ciliary neurotrophic factor, and nerve growth factor, neurotrophin(NT) 3 (NT3), NT4 and NT5); Neuroactive amino acids andpeptides (e.g., γ-aminobutyric acid (GABA), glycine, β-alanine, taurine, and glutamate, and the neuroactive peptides include bradykinin, kallidin, des-Arg.sup.9-bradykinin, des-Arg.sup.10-kallidin, des-Arg.sup.9-[Leu.sup.8]-bradykinin, [D-Phe.sup.7]-bradykinin, HOE 140, neuropeptide Y, enkaphalins and related opioid peptides such as Met.sup.5-enkaphalin, Leu.sup.5-enkephalin, α-, β- and γ-endorphin, α- and ↑-neo-endorphin, and dynorphin; neurotransmitters (e.g., GABA (γ-aminobutyric acid), glycine, glutamate, acetylcholine, dopamine, epinephrine, 5-hydroxytryptamine, substance P, serotonin, enkaphalins and related opioid peptides as above, and catecholamines; Muscarinic receptor agonists and antagonists (e.g., choline esters such as acetylcholine, methacholine, carbachol, bethanechol (carbamylmethylcholine), bethanechol chloride; cholinomimetic natural alkaloids and synthetic analogs thereof, including arecoline, pilocarpine, muscarine, McN-A-343, and oxotremorine. Muscarinic receptor antagonists are generally belladonna alkaloids or semisynthetic or synthetic analogs thereof, such as atropine, scopolamine, homatropine, homatropine methylbromide, ipratropium, methantheline, methscopolamine and tiotropium; anticholinesterases (e.g., ambenonium, ambenonium chloride, demecarium, demecarium bromide, echothiophate iodide, edrophonium, edrophonium chloride, neostigmine, neostigmine bromide, neostigmine methylsulfate, physostigmine, physostigmine salicylate, pyridostigmine, and pyridostigmine bromide); neuromuscular blocking agents and ganglionic blocking drugs (e.g., dicholine esters (e.g., succinylcholine), benzylisoquinolines (d-tubocurarine, atracurium, doxacurium, mivacurium) and pipecuronium, rocuronium, vecuronium), hexamethonium, trimethaphan, and mecamylamine; agents to treat neurodegenerative diseases (e.g., active agents for treating Alzheimer's disease, such as Donezepil, donepezil hydrochloride, physostigmine, physostigmine salicylate, tacrine and tacrine hydrochloride, active agents for treating Huntington's Disease such as, but not limited to, fluoxetine and carbamazepine, anti-Parkinsonism drugs such as, but not limited to, amantadine, apomorphine, bromocriptine, levodopa (particularly a levodopa/carbidopa combination), pergolide, ropinirole, selegiline, trihexyphenidyl, trihexyphenidyl hydrochloride, and anticholinergic agents; and agents for treating ALS such as, but not limited to, spasmolytic (anti-spastic) agents, e.g., baclofen, diazepam, tizanidine, and dantrolene); anti-epileptic agents (e.g., anti-convulsant (anti-seizure) drugs such as azetazolamide, carbamazepine, clonazepam, clorazepate, ethosuximide, ethotoin, felbamate, gabapentin, lamotrigine, mephenytoin, mephobarbital, phenytoin, phenobarbital, primidone, trimethadione, vigabatrin, and the benzodiazepines which are useful for a number of indications, including anxiety, insomnia, and nausea); and CNS and respiratory stimulants (e.g., xanthines such as caffeine and theophylline; amphetamines such as amphetamine, benzphetamine hydrochloride, dextroamphetamine, dextroamphetamine sulfate, levamphetamine, levamphetamine hydrochloride, methamphetamine, and methamphetamine hydrochloride; and miscellaneous stimulants such as methylphenidate, methylphenidate hydrochloride, modafinil, pemoline, sibutramine, and sibutramine hydrochloride).

Also contemplated are drugs that selectively modify CNS function. These include, without limitation, anesthetic agents such as ketamine; opioid analgesics such as alfentanil, buprenorphine, butorphanol, codeine, drocode, fentanyl, hydrocodone, hydromorphone, levorphanol, meperidine, methadone, morphine, nalbuphine, oxycodone, oxymorphone, pentazocine, propoxyphene, sufentanil, and tramadol; nonopioid analgesics such as apazone, etodolac, diphenpyramide, indomethacine, meclofenamate, mefenamic acid, oxaprozin, phenylbutazone, piroxicam, and tolmetin; antiemetics such as chlorpromazine, cisapride, domperidone, granisetron, metoclopramide, ondansetron, perphenazine, prochlorperazine, promethazine, thiethylperazine, and triflupromazine; antihypertensive agents such as apraclonidine, clonidine, guanfacine, and guanabenz; cerebral vasodilators such as vincamine, naftidrofuryl oxalate, papaverine, and nicotinic acid; hypnotic agents and sedatives such as clomethiazole, ethinamate, etomidate, glutethimide, meprobamate, methyprylon, zolpidem, and barbiturates (e.g., amobarbital, apropbarbital, butabarbital, butalbital, mephobarbital, methohexital, pentobarbital, phenobarbital, secobarbital, thiopental); anxiolytics and tranquilizers such as benzodiazepines (e.g., alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, triazolam), buspirone, and droperidol; neuroleptic agents, including antidepressant drugs, antimanic drugs, and antipsychotic agents, wherein antidepressant drugs include (a) the tricyclic antidepressants such as amoxapine, amitriptyline, clomipramine, desipramine, doxepin, imipramine, maprotiline, nortryptiline, protryptiline, and trimipramine, (b) the serotonin reuptake inhibitors citalopram, fluoxetine, fluvoxamine, paroxetine, sertraline, and venlafaxine, (c) monoamine oxidase inhibitors such as phenelzine, tranylcypromine, and (−)-selegiline, and (d) other, "atypical" antidepressants such as bupropion, nefazodone, and trazodone venlafaxine, and antimanic and antipsychotic agents include (a) phenothiazines such as acetophenazine, acetophenazine maleate, chlorpromazine, chlorpromazine hydrochloride, fluphenazine, fluphenazine hydrochloride, fluphenazine enanthate, fluphenazine decanoate, mesoridazine, mesoridazine besylate, perphenazine, thioridazine, thioridazine hydrochloride, trifluoperazine, and trifluoperazine hydrochloride, (b) thioxanthenes such as chlorprothixene, thiothixene, and thiothixene hydrochloride, and (c) other heterocyclic drugs such as carbamazepine, clozapine, droperidol, haloperidol, haloperidol decanoate, loxapine succinate, molindone, molindone hydrochloride, olanzapine, pimozide, quetiapine, risperidone, and sertindole; anticholinergic drugs such as atropine, scopolamine and glycopyrrolate; anti-microbial agents such as (a) tetracycline antibiotics and related compounds (chlortetracycline, oxytetracycline, demeclocycline, methacycline, doxycycline, rolitetracycline), (b) macrolide antibiotics such as erythromycin, clarithromycin, and azithromycin, (c) streptogramin antibiotics such as quinupristin and dalfopristin, (d) beta-lactam antibiotics, including penicillins (e.g., penicillin G, penicillin VK), antistaphylococcal penicillins (e.g., cloxacillin, dicloxacillin, nafcillin, and oxacillin), extended spectrum penicillins (e.g., aminopenicillins such as ampicillin and amoxicillin, and the antipseudomonal penicillins such as carbenicillin), and cephalosporins (e.g., cefadroxil, cefepime, cephalexin, cefazolin, cefoxitin, cefotetan, cefuroxime, cefotaxime, ceftazidime, and ceftriazone), and carbapenems such as imiprenem, meropenem and aztreonam, (e) aminoglycoside antibiotics such as streptomycin, gentamicin, tobramycin, amikacin, and neomycin, (f) glycopeptide antibiotics such as vancomycin, and teicoplanin; (g) sulfonamide antibiotics such as sulfacetamide, sulfabenzamide, sulfadiazine, sulfadoxine, sulfamerazine, sulfamethazine, sulfamethizole, and sulfamethoxazole, (h) quinolone antibiotics such as ciprofloxacin, nalidixic acid, and ofloxacin; (i) anti-mycobacterials such as isoniazid, rifampin, rifabutin, ethambutol, pyrazinamide, ethionamide, aminosalicylic, and cycloserine, (j) systemic antifungal agents such as itraconazole, ketoconazole, fluconazole, and amphotericin B, (k) antiviral agents such as acyclovir, famcicylovir, ganciclovir, idoxuridine, sorivudine, trifluridine, valacyclovir, vidarabine, didanosine, stavudine, zalcitabine, zidovudine, amantadine, interferon alpha, ribavirin and rimantadine, and (1) miscellaneous antimicrobial agents such as chloramphenicol, spectinomycin, polymyxin B (colistin), and bacitracin; alpha adrenergic receptor antagonists such as doxazosin, indoramine, phenoxybenzamine, phentolamine, prazosin, tolazoline, terazosin, trimazosin, and yohimbine; and appetite suppressants such as amphetamine, dextroamphetamine, dextroamphetamine sulfate, diethylpropion hydrochloride, mazindol, methamphetamine hydrochloride, phentermine, and phentennine hydrochloride.

FIG. 14 is a flowchart diagram illustrating a method suitable for constructing a database from neurophysiological data recorded from a group of subjects, according to some embodiments of the present invention. The method can be used for constructing a BNA pattern in embodiments in which the nodes of the BNA pattern are capsule objects.

The neurophysiological data to be analyzed can be any data acquired directly from the brain of the subject under investigation, as further detailed hereinabove. The data can be analyzed immediately after acquisition ("online analysis"), or it can be recorded and stored and thereafter analyzed ("offline analysis"). The neurophysiological data can include any of the data types described above. In some embodiments of the present invention the data are EEG data. The neurophysiological data can be collected before and/or after the subject has performed or conceptualized a task and/or action, as further detailed hereinabove. The neurophysiological data can be used as event related measures, such as ERPs or ERFs, as further detailed hereinabove.

The method begins at 140 and optionally and preferably continues to 141 at which the neurophysiological data are received. The data can be recorded directly from the subject or it can be received from an external source, such as a computer readable memory medium on which the data are stored.

The method continues to 142 at which relations between features of the data are determined so as to identify activity-related features. The activity-related features can be extrema (peaks, trough, etc.) and they can be identified as further detailed hereinabove.

The method continues to 143 at which a parcellation procedure is employed according to the identified activity-related features so as to define a plurality of capsules, each representing at least a spatiotemporal activity region in the brain. Each or some of the capsules can be defined as nodes of the BNA pattern, thereby providing a BNA pattern.

Broadly speaking, parcellation procedure defines a neighborhood of each identified feature. The neighborhood is optionally and preferably a spatiotemporal neighborhood. In some embodiments of the present invention the neighborhood is a spectral-spatiotemporal neighborhood, these embodiments are detailed hereinafter.

The neighborhood can be defined as a spatial region (two- or three-dimensional) in which the extremum is located and/or a time-interval during which the extremum occurs. Preferably, both a spatial region and time-interval are defined, so as to associate a spatiotemporal neighborhood for each extremum. The advantage of defining such neighborhoods is that they provide information regarding the spreading structure of the data over time and/or space. The size of the neighborhood (in terms of the respective dimension) can be determined based on the property of the extremum. For example, in some embodiments, the size of the neighborhood equals the full width at half maximum (FWHM) of the extremum. Other definitions of the neighborhood are not excluded from the scope of the present invention.

In various exemplary embodiments of the invention a spatial grid is built over a plurality of grid elements. The input to the spatial grid built is preferably the locations of the measuring devices (e.g., locations on the scalp, epicortical surface, cerebral cortex or deeper in the brain). In various exemplary embodiments of the invention a piecewise interpolation is employed so as to build a spatial grid having a resolution which is higher than the resolution characterizing the locations of the measuring devices. The piecewise interpolation preferably utilizes a smooth analytical function or a set of smooth analytical functions.

In some embodiments of the present invention the spatial grid is a two-dimensional spatial grid. For example, the spatial grid can describe the scalp, or an epicortical surface or an intracranial surface of the subject.

In some embodiments of the present invention the spatial grid is a three-dimensional spatial grid. For example, the spatial grid can describe an intracranial volume of the subject.

Once the spatial grid is built, each identified activity-related feature is preferably associated with a grid element x (x can be surface element or a point location in embodiments in which a 2D grid is built, or a volume element or a point location in embodiments in which a 3D grid is built) and a time point t. A capsule corresponding to the identified activity-related feature can then be defined as a spatiotemporal activity region encapsulating grid elements nearby the associated grid element x and time points nearby the associated time point t. In these embodiments, the dimensionality of a particular capsule is D+1, where D is the spatial dimensionality.

The nearby grid elements optionally and preferably comprise all the grid elements at which an amplitude level of the respective activity-related feature is within a predetermined threshold range (for example, above half of the amplitude at the peak). The nearby time points optionally and preferably comprise all time points at which the amplitude level of the activity-related feature is within a predetermined threshold range, which can be the same threshold range used for defining the nearby grid elements.

The parceling 143 can optionally and preferably includes applying frequency decomposition to the data to provide a plurality of frequency bands, including, without limitation, delta band, theta band, alpha band, low beta band, beta band, and high beta band, as further detailed hereinabove. Higher frequency bands, such as, but not limited to, gamma band are also contemplated. In these embodiments, the capsules can be defined separately for each frequency band.

The present inventors also contemplate a parceling procedure in which each identified activity-related feature is associated with a frequency value f, wherein the capsule corresponding to an identified activity-related feature is defined as spectral-spatiotemporal activity region encapsulating grid elements nearby x, time points nearby t, and frequency values nearby f. Thus, in these embodiments, the dimensionality of a particular capsule is D+2, where D is the spatial dimensionality.

The definition of capsules according to some embodiments of the present invention is executed separately for each subject. In these embodiments, the data used for defining the capsules for a particular subject includes only the data collected from that particular subject, irrespective of data collected from other subjects in the group.

In various exemplary embodiments of the invention the method continues to 144 at which the data are clustered according to the capsules, to provide a set of capsule clusters. When the capsules are defined separately for each frequency band, the clustering is preferably also executed separately for each frequency band. The input for the clustering procedure can include some or all the capsules of all subjects in the group. A set of constraints is preferably defined, either a priori or dynamically during the execution of the clustering procedure, which set of constraints is selected to provide a set of clusters each representing a brain activity event which is common to all members of the cluster. For example, the set of constraints can include a maximal allowed events (e.g., one or two or three) per subject in a cluster. The set of constraints can also include a maximal allowed temporal window and maximal allowed spatial distance in a cluster. A representative example of a clustering procedure suitable for the present embodiments is provided in the Examples section that follows.

Once the clusters are defined, they can optionally and preferably be processed to provide a reduced representation of the clusters. For example, in some embodiments of the present invention a capsular representation of the clusters is employed. In these embodiments, each cluster is represented as a single capsule whose characteristics approximate the characteristics of the capsules that are the members of that cluster.

In some embodiments, the method proceeds to 145 at which inter-capsule relations among capsules are determined. This can be done using the procedure described above with respect to the determination of the edges of the BNA pattern (see, for example, FIGS. 3B-E). Specifically, the inter-capsule relations can represent causal relation between two capsules. For example, for each of a given pair of capsules, a time window can be defined. These time windows correspond to the width of the capsule along the time axis. A latency difference window between the two capsules can also be defined. This latency difference window corresponds to the separation along the time axis between the capsules.

The individual time windows and latency difference window can be used to define the relation between the pair of capsules. For example, a threshold procedure can be applied to each of these windows, so as to accept, reject or quantify (e.g., assign weight to) a relation between the capsules. The threshold procedure can be the same for all windows, or, more preferably, it can be specific to each type of window. For example, one threshold procedure can be employed to the width of the capsule along the time axis, and another threshold procedure can be employed to the latency difference window. The parameters of the thresholding are optionally dependent on the spatial distance between the capsules, wherein for shorter distance lower time thresholds are employed.

The present embodiments contemplate many types of inter-capsule relations, including, without limitation, spatial proximity between two defined capsules, temporal proximity between two defined capsules, spectral (e.g., frequency of signal) proximity between two defined capsules, and energetic (e.g., power or amplitude of signal) proximity between two defined capsules.

In some embodiments, a group capsule is defined for a group of subjects each having capsule and spatiotemporal peak. The relation between two group capsules is optionally and preferably defined based on the time difference between the respective group capsules. This time difference is preferably calculated between the corresponding two spatiotemporal peaks of subjects from both group capsules. This time difference can alternatively be calculated between the onsets of the spatiotemporal event activations of each of the capsules (rather than the time differences between peaks).

For example, the two group capsules can be declared as a pair of related capsules if the time difference between the capsules among subjects having those capsules is within a predefined time window. This criterion is referred to as the time-window constraint. A typical time-window suitable for the present embodiments is several milliseconds.

In some embodiments, the relation between two group capsules is defined based on the number of subjects having time those capsules. For example, the two group capsules can be declared as a pair of related capsules if the number of subjects having the capsules is above a predetermined threshold. This criterion is referred to as the subject number constraint. In various exemplary embodiments of the invention the both time window constraint and the subject number constraint are used in addition, wherein two group capsules are declared as a pair of related capsules when both the time window constraint and the subject number constraint are fulfilled. The maximum number of subjects that can create a particular pair of capsules is referred to as the intersection of subjects of the two groups.

Thus, in the present embodiments a capsule network pattern is constructed, which capsule network pattern can be represented as a graph having nodes corresponding to capsules and edges corresponding to inter-capsule relations. Such a capsule network pattern is referred to herein as a connected capsule BNA pattern.

In some embodiments of the present invention the method applies (operation 149) a feature selection procedure to the capsules to provide at least one sub-set of capsules.

In some embodiments of the present invention a forward selection of features is employed and in some embodiments of the present invention a backward selection features is employed. In some embodiments of the present invention the method employs a procedure for controlling the fraction of false positives that may lead to poor selection, such procedure is known as false discovery rate (FDR) procedure, and is found, for example, in Benjamini et al. supra, the contents of which are hereby incorporated by reference.

A representative example of a feature selection procedure suitable for the present embodiments is illustrated in FIG. 33. Initially, a group of subjects is considered (for example, either healthy controls or diseased subjects), optionally and preferably using a sufficiently large dataset to as to provide relatively high accuracy in representing the group. The group can be represented using a set of capsules. The feature selection procedure is then applied on a training set of the dataset in order to evaluate each feature or various combinations of features characterizing the group's dataset. The input to the feature selection algorithm is preferably evaluation scores (e.g., the score for each participant in the training set on each of the features) calculated using the training set. Feature selection can also be applied, on other features, such as, but not limited to, BNA pattern event-pairs, and EEG and ERP features such as, but not limited to, coherence, correlation, timing and amplitude measures. Feature selection can also be applied on different combinations of these features.

The outcome of this procedure can be a set of supervised network of capsules, each suitable to describe a different sub-group of the population with a specific set of features. The networks obtained during the procedure can allow a comparison of the capsules obtained for a single subject to a specific network or networks. Thus, the obtained networks obtained can serve as biomarkers.

In some embodiments of the invention, the method continues to 146 at which weights are defined for each cluster (or capsular representation thereof) and/or each pair of clusters (or capsular representations thereof). Weights for pairs of clusters can be calculated as described above with respect to the weights assigned to the edges of the BNA.

Weights for individual capsules or clusters can describe the existence level of the particular capsule in the database. For example, the weight of a cluster can be defined as the mean amplitude as calculated over all the capsules in the cluster. The weight is optionally and preferably normalized by the sum of all amplitude means of all clusters.

Also contemplated is a weight that describes the statistical distribution or density of one or more of the parameters that define the capsules in the cluster. Specifically, the weight can include at least one of: the distribution or density of the amplitudes over the cluster, the spatial distribution or spatial density over the cluster, the temporal distribution or temporal density over the cluster, and the spectral distribution or spectral density over the cluster.

At 147 the method stores the clusters and/or representations and/or capsule network pattern in a computer readable medium. When weights are calculated, they are also stored.

The method ends at 148.

FIG. 15 is a flowchart diagram illustrating a method suitable for analyzing neurophysiological data recorded from a subject, according to some embodiments of the present invention.

The neurophysiological data to be analyzed can be any data acquired directly from the brain of the subject under investigation, as further detailed hereinabove. The data can be analyzed immediately after acquisition ("online analysis"), or it can be recorded and stored and thereafter analyzed ("offline analysis"). The neurophysiological data can include any of the data types described above. In some embodiments of the present invention the data are EEG data. The neurophysiological data can be collected before and/or after the subject has performed or conceptualized a task and/or action, as further detailed hereinabove. The neurophysiological data can be used as event related measures, such as ERPs or ERFs, as further detailed hereinabove.

The method begins at 150 and optionally and preferably continues to 151 at which the neurophysiological data are received. The data can be recorded directly from the subject or it can be received from an external source, such as a computer readable memory medium on which the data are stored.

The method continues to 152 at which relations between features of the data are determined so as to identify activity-related features. The activity-related features can be extrema (peaks, trough, etc.) and they can be identified as further detailed hereinabove.

The method continues to 153 at which a parcellation procedure is employed according to the identified activity-related features so as to define a plurality of capsules, as further detailed hereinabove. The capsules and the relations between capsules define a capsule network pattern of the subject, as further detailed hereinabove.

In some embodiments, the method proceeds to 157 at which a feature selection procedure is employed as further detailed hereinabove.

The method optionally and preferably continues to 154 at which a database having a plurality of entries, each having an annotated database capsule is accessed. The database can be constructed as described above with respect to FIG. 14.

The term "annotated capsule" refers to a capsule which is associated with annotation information. The annotation information can be stored separately from the capsule (e.g., in a separate file on a computer readable medium). The annotation information can be associated with a single capsule or a collection of capsules. Thus, for example, the annotation information can pertain to the presence, absence or level of the specific disorder or condition or brain function. Also contemplated are embodiments in which the annotation information pertains to a specific brain related disorder or condition in relation to a treatment applied to the subject. For example, a capsule (or collection of capsules) can be annotated as corresponding to a treated brain related disorder. Such capsule (or collection of capsules) can also be annotated with the characteristics of the treatment, including dosage, duration, and elapsed time following the treatment. A capsule (or collection of capsules) can optionally and preferably be annotated as corresponding to an untreated brain related disorder. Any of the disorders, conditions brain functions, and treatments described above can be included in the annotation information.

Alternatively or additionally, the capsule (or collection of capsules) can be identified as corresponding to a specific group of individuals (e.g., a specific gender, ethnic origin, age group, etc.), wherein the annotation information pertains to the characteristics of this group of individuals.

The database can include capsules defined using data acquired from a group of subjects, or it can capsules defined using data acquired from the same subject at a different time, for example, an earlier time. In the latter case, the annotation of the capsules can include the acquisition date instead or in addition to the aforementioned types of annotations.

The method proceeds to 155 at which at least some (e.g., all) of the defined capsules are compared to one or more reference capsules.

The present embodiments contemplate more than one type of reference capsules.

In some embodiments of the present invention the reference capsules are baseline capsules defined using neurophysiological data acquired from the same subject at a different time, for example, an earlier time.

A particular and non-limiting example for these embodiments is the case of several treatment sessions, e.g., N sessions, for the same subject. Data can be acquired before and after each session and capsules can be defined for each data acquisition. The capsules defined before treatment can be used as baseline capsules to which capsules acquired from post treatment acquisition can be compared. In some embodiments of the present invention the baseline capsules are capsules defined from acquisition before the first session, wherein capsules defined from each successive acquisition are compared to the same baseline capsules. This embodiment is useful for assessing the effect of the treatment over time. In some embodiments of the present invention the baseline capsules are capsules defined from acquisition before the kth session, wherein capsules defined from an acquisition following the kth session are compared to these baseline capsules. This embodiment is useful for assessing the effect of one or more particular sessions.

The comparison can optionally be used for determining presence, absence and/or level of neural plasticity in the brain.

Determination of neural plasticity is particularly useful for subjects suffering a stroke, wherein part of the brain is damaged and other parts begin to function or change their function. A comparison between two capsules or set of capsules of a subject after a stroke can be used to identify a change in brain activity hence also to assess neural plasticity in the brain. Determination of neural plasticity is particularly useful for subjects suffering from chronic pain. A comparison between two capsules or set of capsules can be used to identify a change in brain activity hence also to assess those chemical changes. Such assessment can be used, for example, in combination with a pain stimulus, to determine the likelihood that the subject is a chronic pain sufferer or having normal response to the pain stimulus.

The comparison can optionally be used for of estimating the likelihood of Traumatic brain injury (TBI). TBI is often classified into mild, moderate and severe TBI based on three parameters: 1) the quality and length of change in consciousness, 2) the length of amnesia (memory loss), and 3) the Glasgow Coma Scale (GCS). Traditionally, a brain injury is classified as concussion (mTBI) is the length of consciousness is less than 20 minutes and amnesia is 24 hours or less, and is the GCS score is above 13. A comparison between two capsules or set of capsules of the same subject can be used to identify a change in brain activity hence also to assess the presence absence or likelihood of TBI, e.g., brain concussion.

In some embodiments of the present invention the reference capsules are capsules defined using neurophysiological data acquired form a different subject.

The variation of a particular capsule as defined from the data relative to the baseline capsule (for example, as defined previously, or as defined from previously acquired data), can be compared according to some embodiments of the present invention to variations among two or more capsules annotated as normal. For example, the variation of a particular capsule relative to the baseline capsule can be compared to a variation of a first capsule annotated as normal and a second capsule also annotated as normal. These annotated capsules are optionally and preferably defined from neurophysiological data acquired from different subjects identified as having normal brain function.

The advantage of these embodiments is that they allow assessing the diagnostic extent of the observed variations of a particular capsule relative to a baseline capsule.

For example, when the variation relative to the baseline capsule are similar to the variations obtained from neurophysiological data among two or more different subjects identified as having normal brain functions, the method can assess that the observed variation relative to the baseline capsule are of reduced or no significance.

On the other hand, when the variation relative to the baseline capsule are substantive compared to the variations among normal subjects, the method can assess that the observed variation relative to the baseline capsule are diagnostically significant.

In embodiments in which a database of previously annotated capsules is accessed (operation 154) the reference capsules are optionally and preferably the capsules of the database. The capsules can be compared to at least one database capsule annotated as abnormal, and at least one database capsule annotated as normal. A database capsule annotated as abnormal is a capsule which is associated with annotation information pertaining to the presence, absence or level of a brain related disorder or condition. A database capsule annotated as normal is a capsule which was defined using data acquired from a subject or a group of subjects identified as having normal brain function. Comparison to a database capsule annotated as abnormal and a database capsule annotated as normal is useful for classifying the subject according to the respective brain related disorder or condition. Such classification is optionally and preferably provided by means of likelihood values expressed using similarities between the respective capsules.

The comparison between capsules is typically for the purpose of determining similarity between the compared capsules. The similarity can be based on correlation between the capsules along any number of dimensions. In experiments performed by the present inventors, correlation between two capsules that were not even in their size was employed. These experiments are described in more detail in the Examples section that follows.

The comparison between capsules can comprise calculating a score describing the degree of similarity between the defined capsule and the capsules of the data base. When the database corresponds to a group of subjects having a common disorder, condition, brain function, treatment, or other characteristic (gender, ethnic origin, age group, etc.), the degree of similarity can express, for example, the membership level of the subject in this group. In other words, the degree of similarity expresses how close or how far are the disorder, condition, brain function, treatment, or other characteristic of the subject from that of the group.

The score calculation can include calculating of a statistical score (e.g., z-score) of a spatiotemporal vector corresponding to the subject's capsule using multidimensional statistical distribution (e.g., multidimensional normal distribution) describing the respective database capsule. In some embodiments of the present invention, the statistical score is weighed using the weights in the database. The score calculation can also include calculation of a correlation between capsule and a respective database capsule. A representative example of a scoring procedure suitable for the present embodiments is provided in the Examples section that follows.

The score of a particular score relative to the database can also be used for comparing two capsules two each other. For example, consider a first capsule C1 and a second capsule C2 which, a priori, is not the same as C1. Suppose that C1 is compared to database X and is assigned with a score S1. Suppose further that C2 is compared to a database Y (which, in some embodiments is database X, but may also be a different database) and is assigned with a score S2. The comparison between C1 and C2 is achieved according to some embodiments of the present invention by comparing S1 to S2. These embodiments are particularly useful when one of C1 and C2 is a baseline capsule, and when C1 and C2 are defined from neurophysiological data collected from different subjects.

The comparison between the subject's capsule and database capsules can be executed irrespective of any inter-capsule relation of any type. In these embodiments the subject's capsule is compared to the database capsules without taking into account whether a particular pair of database capsules has a relation in terms of time, space, frequency or amplitude.

Alternatively, the method can determine inter-capsule relations among the defined capsules, and construct a capsule network pattern responsively to the inter-capsule relations, as further detailed hereinabove. In these embodiments, the comparison is between the constructed pattern and the database pattern.

The comparison between the subject's capsule and database capsules is optionally and preferably with respect to the supervised network of capsules obtained during the feature selection procedure (see, for example, FIG. 33).

Several comparison protocols are contemplated, and are schematically illustrated in FIGS. 34A-C.

In the comparison illustrated in FIG. 34A, a matching process that allows quantifying the degree of similarity between the brain activity of the single subject and that represented by the network(s) is employed. The overall degree of similarity can be quantified, according to some embodiments of the present invention, by a score which is a weighted sum of the separated similarity scores associated with all of the compared features. In embodiments in which several networks are obtained, each network characterizes a specific sub-group in the population. In these embodiments, the subject can be matched against a network or networks associated with a sub-group that most resemble the characteristics of the subject.

In the comparison illustrated in FIG. 34B, the capsule network pattern of the subject is compared against the group network and the representative matching features (e.g., best matching features) of the single subject to those of the group network are preferably selected. These representative matching features can be used as an approximation of the intersection between the single-subject capsule network and the group network and constitute a personalized single-subject sub-network that serves as a reference baseline used in multiple tests of the same subject.

In some embodiments, the single subject may be compared against several group sub-networks describing homogeneous subtypes enabling fine-tuning in choosing a single subject network that can serve as a reference. Thus, matching individual features to the features of the group's network allows the extraction of a customized network and a comparison of the individual to a sub-set of features most characterizing their condition (e.g., healthy, diseased).

In the comparison illustrated in FIG. 34C, various combination of comparisons are shown. These include, but are not limited to, single subject network against another single subject network, network against the intersection between the network and the single subject network, and the like.

The method ends at 156.

In various exemplary embodiments of the invention, the information extracted from the comparison 155 pertains to the likelihood of abnormal brain function for the subject. Additionally, the comparison can optionally and preferably be used for extracting prognostic information. For example, the capsules can be compared to a reference (e.g., baseline) set of capsules that characterizes a group of subject all suffering from the same abnormal brain function with similar rehabilitation history, wherein the baseline set of capsules is constructed from neurophysiological data acquired at the beginning of the rehabilitation process. The similarity level between the capsules obtained at 153 and the reference set of capsules can be used as a prognosis indicator for the particular abnormal brain function and the particular rehabilitation process.

The likelihood of abnormal brain function is optionally and preferably extracted by determining a brain-disorder index based, at least in part, on the similarity between the capsules obtained at 153 and the reference set of capsules, as further detailed hereinabove with respect to the comparison of BNA pattern 20 and the annotated BNA pattern(s).

It is to be understood that the capsules of the present embodiments can be used for assessing likelihood of many brain related disorders, including any of the aforementioned brain related disorders.

A baseline set of capsules can also be associated with annotation information pertaining to a specific brain related disorder or condition of a group of subjects in relation to a treatment applied to the subjects in the group. Such baseline set of capsules can also be annotated with the characteristics of the treatment, including dosage, duration, and elapsed time following the treatment. A comparison of the capsules obtained at 153 to such type of baseline set of capsules can provide information regarding the responsiveness of the subject to treatment and/or the efficiency of the treatment for that particular subject. Such comparison can optionally and preferably be used for extracting prognostic information in connection to the specific treatment. A set of capsules that is complementary to such baseline set of capsules is a set of capsules that is annotated as corresponding to an untreated brain related disorder.

Optionally and preferably, the method compares the capsules obtained at 153 to at least one baseline set of capsules annotated as corresponding to a treated brain related disorder, and at least one baseline set of capsules annotated as corresponding to an untreated brain related disorder.

The capsules of the present embodiments can also be used for determining a recommended dose for the subject. Specifically, the dose can be varied until a sufficiently high or maximal similarity to the baseline set of capsules for treated subjects is obtained. Once such similarity is achieved, the method can determine that the dose achieving such similarity is the recommended dose for this subject.

In various exemplary embodiments of the invention, the comparison between capsules is used to extract information pertaining to the level of pain the subject is experiencing. Preferably, the information includes an objective pain level. Pain level assessment according to some embodiments of the present invention is particularly useful in institutions that provide treatment or rehabilitation for subjects suffering from chronic pain.

In some embodiments of the present invention the capsules obtained at 153 are compared to a set of capsules constructed for the same subjects at a different time. These embodiments are useful for many applications.

For example, in some embodiments, the comparison is used for determining presence, absence and/or level of neural plasticity in the brain, as further detailed hereinabove with respect to the comparison between BNA patterns.

In some embodiments, a set of capsules obtained from neurophysiological data acquired following a treatment is compared to a set of capsules obtained before a treatment. Such comparison can be used for assessing responsiveness to and optionally efficacy of the treatment.

In some embodiments, a set of capsules obtained from neurophysiological data acquired while the subject performs a particular task is compared to a set of capsules obtained from neurophysiological data acquired while the subject is not performing the particular task and/or while the subject performs another particular task.

The capsules of the present embodiments can also be used for inducing improvement in brain function. In some embodiments of the present invention a set of capsules is obtained for a subject during a higher-level cognitive test, generally in real time. The subject can be presented with the set of capsules (for example, a graphical presentation can be used) and use them as a feedback. For example, when, as a result of the cognitive action, the set of capsules of the subject becomes more similar to a characteristic set of capsules of a healthy group, presentation of such a result to the subject can be used by the subject as a positive feedback. Conversely, when, as a result of the cognitive action, the set of capsules of the subject becomes more similar to a characteristic set of capsules of a brain-disorder group, presentation of such a result to the subject can be used by the subject as a negative feedback. Real time analysis of BNA patterns in conjunction with neurofeedback can optionally and preferably be utilized to achieve improved cortical stimulation using external stimulating electrodes.

The capsules of the present embodiments can also be used for assessing responsiveness to and optionally efficacy of a phototherapy and/or hyperbaric therapy, as further detailed hereinabove with respect to the comparison between BNA patterns.

Additional examples of treatments which may be assessed by the capsules comparison technique of the present embodiments include, without limitation, ultrasound treatment, rehabilitative treatment, and neural feedback, e.g., EMG biofeedback, EEG neurofeedback, transcranial magnetic stimulation (TMS), and direct electrode stimulation (DES).

In some embodiments of the present invention local stimulation is applied to the brain responsively to the information extracted from the comparison 155. The local stimulation is optionally and preferably at one or more locations corresponding to a spatial location of at least one of the nodes of the BNA pattern. Operations 151, 152 and 153 of the method can be executed repeatedly, and the local stimulation can be varied according to some embodiments of the present invention responsively to variations in the extracted information. Thus, the stimulation and capsule analysis can be employed in a closed loop, wherein the capsule analysis can provide indication regarding the effectiveness of the treatment. The closed loop can be realized within a single session with the subject, e.g., while the electrodes that are used to collect the data from the brain and the system that is used for applying the stimulation engage the head of the subject.

The present embodiments contemplate many types of local stimulation, including any of the aforementioned types of local stimulation and combinations of local stimulations.

The local stimulation can be at one or more locations corresponding to a spatial location of at least one of the capsules of the capsule network pattern. For example, the capsule network pattern can be analyzed to identify locations that correspond to a brain disorder. At these locations, local stimulation can be applied to reduce or eliminate the disorder. Alternatively, the local stimulation can be applied at locations corresponding to other capsules of the capsule network pattern. These other locations can be locations at which previous stimulations for the same subject or group of subjects have been proven to be successful in reducing or eliminating the disorder.

A representative example of application of local stimulation is in the case of pain. In these embodiments the local stimulation is applied to reduce or eliminate the pain. Thus, the capsule network pattern can be analyzed to identify capsules that correspond to pain, and the stimulation can be applied to locations that correspond to these capsules.

In some embodiments, a pain stimulus (such as heat stimulus) can be applied to the subject prior to or while acquiring the neurophysiological data. The capsule network pattern can be analyzed to identify capsules that correspond to the applied pain stimulus and the local stimulation can be at one or more locations corresponding to those identified capsules. These embodiments are useful, particularly, but not exclusively, for situations of chronic pain (e.g., fibromyalgia).

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Exemplified Spatio-Temporal Parcellation (STEP) Procedure

The STEP Procedure of the present embodiments parcels the full spatial and temporal dimensions of the ERP into a set of unitary events, for example, extremum points and their surroundings. The challenge of matching two or more biological time series collected from different subjects derives from the accepted existence of common hidden functional microstates and shifting times among subjects performing a common task. The parcellation definition of STEP allows matching different signals without distorting signal shape and time dependency. Thus, a pool of microstate sets of group members can undergo clustering in order to define and isolate group-common templates.

The STEP Procedure of the present embodiments translates the relevant spatial spread and temporal dynamics in a natural way into a set of microstates, thereby addressing two drawbacks in conventional spatiotemporal analysis methods: the constraint of using the entire spatiotemporal map as a global state and the loss of time dynamics in the microstate.

Methods

Subjects

Two groups of healthy right handed male and female subjects, from two different centers, participated in the study. The first group included 40 subjects (17 males) with an age range of 23-64 years from Ra'anana, Israel and the second group included 60 subjects (30 males) with an age range of 15-24 years from Kansas, USA. All participants signed informed consent forms for undergoing the procedures, which were approved by the Ethics Committee of the respective centers.

Task and Data Acquisition

All subjects underwent an auditory oddball task. In the auditory oddball target detection test, the subjects were requested to respond to auditory target stimuli that occur infrequently and irregularly within a series of standard stimuli. There were 600 trials of which 80% were 2000 Hz stimuli (Frequent), 10% were 1000 Hz rare stimuli requiring a response (Target) and 10% were rare non-targets composed of various sounds (Novel). Stimuli were separated by 1500 ms intervals.

Subjects were requested to fixate on a sign in the middle of a screen. Sound was delivered using a headset and the sound level was set to 70 dB. Subjects of the first group went through three repeated sessions spaced one week apart.

EEG recordings were obtained using a 64-channel Biosemi Active Two system (Amsterdam, Netherlands). The sampling rate was 256 Hz. The second group went through two repeated sessions and recordings were obtained using a HydroCel Geodesic Sensor Net of 128-channels and net amps 300 amplifier of EGI (Eugene, Oreg.). The sampling rate was 250 Hz.

Artifact removal procedure included noisy electrode removal (extensive ranges of amplitude outside the range of ±100 V or high dissimilarity to neighbor electrodes), noisy epoch removal (epochs with amplitude outside the range of ±100 V or if a channel's amplitude deviated from 7 STDs from its mean) and eye artifact correction using ICA. All artifact removal stages were done using EEGLAB software (v. 9.0.4s).

Data Analysis

The data analysis procedure used in the present example according to some embodiments of the invention is illustrated in the block diagram of FIG. 15. The procedure included pre-processing, single subject feature extraction, group clustering and single subject scoring (relative to group characteristics). Each of those stages can stand on its own, depending on different types of analysis.

For each subject, the ERPs were first decomposed into four conventional frequency bands, $\delta$ (0.5-4 Hz), $\theta$ (3-8 Hz), $\alpha$ (7-13 Hz) and $\beta$ (12-30 Hz). Linear-phase FIR filter design using least-squares error minimization and reverse digital filtering was used. Next, a high resolution spatial grid of the brain activity (33*37 pixels) was calculated. For each time sample, the activity of all recording electrodes was interpolated to a 2D grid according to the estimated projection of the 3D electrode array by use of cubic splines interpolation.

After pre-processing, the procedure extracted spatio-temporal events and their associated surroundings. A spatiotemporal event was defined as an extremum amplitude point (peak). The peak's surrounding was defined as all voxels around the peak (on the spatial 2D grid as well as on the time dimension) with activity higher than half the amplitude absolute value of the peak. The ensuing features that characterized each subject's brain activity were sets of all peaks and of encapsulated activity regions in time and space around the peak for each frequency band (FIG. 16, block B). These activity regions are referred to in this Example as capsules.

Block C represents a clustering operation in which the encapsulated brain activity regions were clustered for a group of subjects at a given frequency band. The input features for the clustering are all capsules of all subjects in the group. The clustering goal was to get a set of clusters, each representing a unitary event common to all members of the cluster.

In order to achieve this goal, a constraint of maximum participation of one unitary event per subject in a cluster was applied. Additional constraints included a maximum temporal window and spatial distance allowed in a cluster. The temporal windows were 200, 125, 77, 56 ms in accordance with the four frequency bands of δ, θ, α and β, respectively. The spatial window was equivalent to the minimum distance between non-neighboring electrodes in the 10-20 system of 64 electrodes.

The clustering procedure contained 3 stages, as follows.

a. Map all optional clusters. The mapping was done under the constraints specified above and ignored clusters which were contained within higher quality clusters.

b. Implement a greedy procedure to choose the best clusters, in order to have a set of clusters that contains at least 70% of the subjects and without any peaks overlapping between clusters. The quality measure of a cluster was a factor of a combination of the number of participating subjects, the Euclidian distance between individual peaks and the peak's surroundings correlations in a cluster. A correlation between two peak's surroundings was calculated after normalizing the surroundings by the Global Field Power (GFP) as defined in Ref. [6] and alignment of the surroundings by their peaks.

c. Get a group representation. A group representation has the same characteristics as a single subject representation. In the present Example, the group representation was a set of capsules equal in number to the number of clusters achieved by the previous stage. A group's peak location was defined as the average of the peak locations of all members of the cluster. In order to arrive at a group's peak surroundings, an averaged surrounding was calculated. For each subject participating in the cluster, his original high resolution ERP was taken and aligned to the group's peak by the relevant subject's peak. Averaging of all aligned ERPs provided a new averaged high resolution ERP around the group's peak, from which the surroundings of the peak were extracted. The surrounding was extracted in the same manner as in a single subject. The final output of the clustering was a set of group common capsules, which were averages of the single subjects' capsules contained in each original cluster. This set of capsules characterized the group-common brain activity.

At block D, single subject scoring was calculated relative to the set of group-common capsules. A single subject representation was similar to that of a group in terms of peaks and surroundings, except for the group having means and SDs for the peaks locations. Naturally, a group had less unitary events than a single subject. The subject score was a weighted sum of the best match of his capsules to those of the group:

$$S_{score} = \sum_{S_i, G_j}^{pairs\,of\,best\,matched\,peaks} (\text{capsule\_corr}(S_i, G_j) * S_{temporal\_dist}(S_i, G_j) * G_{amp\_weight}(G_j))$$

where $S_i$, $G_j$ are the best matched pair of capsules found by the scoring algorithm of the single subject and group, respectively; capsule_corr($S_i$,$G_j$) equals zero if $S_{peak}(i)$, $G_{peak}(j)$ do not meet the constraints, and corr($S_{surr}(i)$, $G_{surr}(j)$) otherwise; $S_{peak}(i)$, $G_{peak}(j)$ are the spatio-temporal peaks of the single subject and the group, respectively; $S_{surr}(i)$, $G_{surr}(j)$ are the capsules of the single subject and the group, respectively; corr(•,•) is correlation normalized and aligned to the peak correlation; $S_{temporal\_dist}$ is defined as:

$$S_{temporal\_dist}(S_i, G_j) = N(S_{peak}(i); \mu(G_{peak}(J)), \sigma^2(G_{peak}(j)));$$

N(•; ‖, $\sigma^2$) is the normal distribution with $\mu, \sigma^2$ parameters; $G_{amp\_weight}$ is defined as:

$$G_{amp\_weight}(G_j) = mean_{amp}(G_{peak}(j)) \Big/ \sum_{k}^{allpeaks} mean_{amp}(G_{peak}(k)); \text{ and}$$

$mean_{amp}(\bullet)$ is the mean of the amplitudes of the peaks in the cluster.

General Considerations

In lieu of a patient group for comparison with the normal one, the evoked response to the Novel stimulus was regarded as being a pathological variant of the normal Target response and the ability of the STEP procedure to correctly classify the two responses was tested.

Additionally, in order to test the general applicability of the method under less rigorous and more realistic conditions, only the ERPs of Group 1 subjects during their 3rd visit were used for creating the common templates. Members of Group 2 with its different age range, testing system, electrode number and placement and sampling rate were scored on those templates and the Target-Novel classification was applied on these members as well.

Results

Target group representation consisted of 15 capsules, 6 and 9 capsules in the θ and α band, respectively. Novel group representation consisted of 14 capsules, 2, 5 and 7 in the δ, θ and α bands, respectively. The relevant analysis time is 0 to 600 ms post-stimulus. Groups' capsules are shown in FIGS. 17A and 17B. Shown in FIGS. 17A and 17B, are the contour of the capsules of Target and Novel from the first group's 3rd visit. The Y-Z plane is the 2D brain activity grid, and the points in the middle of each capsule are the peaks.

The STEP procedure utilized in the present example successfully classified the Novel vs. Target responses. Clustering was performed on the first group's 3rd visit. The other 2 visits of the first group and the two visits of the second group were then classified against the ensuing group capsules, based on STEP scoring.

ROC curves were calculated for all group, visit and frequency band combinations. It became apparent that θ band capsules were dominant in all combined-frequency scores and that they are better Novel-Target classifiers then other frequency bands (Table 1). The respective sensitivity and specificity values as derived from the cut-off points on the θ band. ROC curve were 0.85 and 0.9 for the best classification (AUC=0.947) and 0.73 and 0.65 for the worst (AUC=0.77).

TABLE 1

ROC curves AUC values for all frequencies.

| Group | Visit | δ | Θ | A | Combined frequencies |
|---|---|---|---|---|---|
| 1 | 1 | 0.697 | 0.871 | 0.721 | 0.872 |
|  | 2 | 0.716 | 0.947 | 0.736 | 0.923 |

TABLE 1-continued

ROC curves AUC values for all frequencies.

| Group | Visit | δ | Θ | A | Combined frequencies |
|---|---|---|---|---|---|
| 2 | 1 | 0.563 | 0.770 | 0.551 | 0.72 |
|   | 2 | 0.700 | 0.820 | 0.567 | 0.814 |

The θ band ROC curves for the 4 group-visit combinations are plotted in FIG. 18. In FIG. 18, G1 and G2 denote group 1 and group 2, respectively, and V1 and V2 denote the first and second visits, respectively. The blue circles are cut-off points of the ROC analysis. The associated statistical details of the ROC curves shown in FIG. 18 are listed in Table 2.

TABLE 2

ROC statistical details

| Group | Visit | AUC | SE | P-value | CI | Sensitivity | Specificity |
|---|---|---|---|---|---|---|---|
| 1 | 1 | 0.871 | 0.041 | $<10^{-15}$ | [0.79, 0.95] | 0.85 | 0.75 |
|   | 2 | 0.947 | 0.026 | $<10^{-15}$ | [0.89, 1.00] | 0.85 | 0.90 |
| 2 | 1 | 0.770 | 0.045 | $9.4 \times 10^{-10}$ | [0.68, 0.85] | 0.73 | 0.65 |
|   | 2 | 0.820 | 0.041 | $1.5 \times 10^{-15}$ | [0.74, 0.89] | 0.76 | 0.75 |

Discussion

The STEP procedure utilized in algorithm produced stimulus-specific group activity templates. The procedure correctly classified closely related evoked responses. An improvement in classification can be achieved by locating and basing the score on capsules that show high differentiation characteristics.

Once the subject's ERP is satisfactorily represented, more than one evaluation modes can be employed to assess change (mainly deterioration) in the ERP over time. In some embodiments, a wide as possible baseline database is collect from the subject, against which each additional performance is optionally and preferably tested for conformity. In some embodiments of the present invention the widest common denominator in the response of a representative group of normal subjects is defined, and the evolution of the single subject's conformity to that of the group is followed. The inventive STEP procedure is useful in these embodiments since it allows grading the similarity between any two trials as well as between a single trial and a derived group-common template.

Example 2

Following is a description of a technique suitable for various applications, including, without limitation, concussion management, according to some embodiments of the present invention. In some embodiments, the technique is demonstrated on a scopolamine induced cognitive impairment model.

The BNA technique of the present embodiments can be used to provide quantitative and/or qualitative outputs that are useful according to some embodiments of the present invention for monitoring brain activity of individual subjects over time.

The present inventors performed computer simulations and experiments directed to determine test-retest repeatability of the technique of the present embodiments, and for demonstrating the clinical applications offered by the technique of the present embodiments.

Methods

BNA Analysis

FIG. 19 is a block diagram describing the technique of the present embodiments. The Reference Brain Network Model is generated to serve as a reference baseline integrated into the computerized method of the present embodiments and used to calculate BNA Scores of individual subjects (layer 1). 40 healthy control subjects (18 males, 22 females) ages 23-64 were utilized for this purpose.

The Normative Database represents the change in BNA Scores (ΔBNA Scores) and is generated in order to determine the standard deviation (SEM) of BNA Scores over repeat test sessions to establish a reference for trend analysis (layer 2). 60 healthy control subjects (30 males, 30 females) ages 15-24 were utilized for this purpose. The trend analysis included a search for a best trend over a plurality of trend candidates.

SEM cut-offs allow the clinician to estimate the degree of the relative changes of the BNA Scores over time for trend analysis of the electrophysiological brain activity (layer 3).

A BNA Analysis System generates according to some embodiments of the present invention quantitative scores from EEG data by comparing EEG activity of a group of normative subjects to a set of reference brain network models (Layer 1). These score can then be used to construct a normative database which typically constitutes at least these scores. The database can be utilized to determine statistical deviations (Layer 2). BNA score of individual subjects can then be compared to this database, to provide a tool for the assessment of trend analysis of electrophysiological changes over time (Layer 3).

The BNA Analysis of the present embodiments can be used for Revealing BNA patterns in groups of subjects, and/or for comparing brain activity of individual subjects to group BNAs. The comparison can include a qualitative output in the form of, for example, individual BNA patterns, and/or a quantitative output, in the form of, for example, one or more (e.g., 2, 3, 4 or more) BNA scores.

A group BNA analysis can provide a Reference Brain Network Model (see, Layer 1 in FIG. 19). A quantitative individual subject analysis can provide a normative database (Layer 2 in FIG. 19). A quantitative and/or qualitative individual subject analysis can provide a trend analysis (Layer 3 in FIG. 19).

FIG. 20 illustrates an outline of a functional network analysis, suitable for the present embodiments. In some embodiments of the present invention the BNA analysis comprises two independent processes: group pattern analysis (blue arrows) and individual subject evaluation (red arrows).

For the group analysis, the raw data (such as, but not limited to, EEG data) of each subject undergoes at least one of the following processing stages: (1) preprocessing (A-C—artifact removal, band-passing); (2) salient event extraction (D-E—discretization, normalization), and (3) network analysis (F-H—clustering, unitary events extraction, pair-pattern extraction, group-template formation) performed on the pooled salient events of all subjects (multiple blue arrows). The stages (1)-(3) are optionally and preferably executed consecutively.

For the single subject level process, at least one of the following stages is preferably executed: a first and a second stage can be identical to those of the group level process (B-E), and a third stage, can include comparing the single subject activity to the set of templates issuing from the group analysis stage. The comparison optionally and preferably includes also calculating one or more scores describing the comparison.

Cognitive Task

The task chosen for this study was the Auditory Oddball Task, but other tasks are not excluded from the scope of the present invention. FIG. 21 is a schematic representation of an Auditory Oddball Task used in this study. The task included 600 repetitive 1000 ms auditory stimulations of which 80% were 2000 Hz stimuli (Frequent—blue circles), 10% were 1000 Hz stimuli requiring a motor response (Target—red circles) and 10% were rare non-targets composed of various sounds (Novel—yellow star). The stimuli were separated by 1500 ms intervals. The sound was delivered through a headset at a sound pressure level of 70 dB.

Statistical Analysis

Repeatability: Within-subject BNA score repeatability was assessed by computing the Intraclass Correlation.

Normality Tests: Normality of ΔBNA distributions was evaluated using the Kolmogorov-Smirnov test of normality (p>0.200) and validated with corresponding Q-Q plots.

SEM Computation: The change over time in the BNA Scores of a subject/patient from baseline (ΔBNA) is evaluated in terms of standard error of measurements (SEM) against the Normative Database to determine likelihood of true change.

Results

Statistical Analysis of Normative Database

FIG. 22 shows normative Database's Interclass Correlation (ICC) values for BNA scores in the two EEG-ERP sessions.

FIG. 23 shows Q-Q plot for the Connectivity ΔBNA scores of the Novel stimulus. The near-perfect linearity of the scattergram is strong evidence for normality FIG. 24 shows frequency histogram for the Connectivity ΔBNA scores of the Novel stimulus. Frequency units are number of scores out of 60. One and two SEMs around the mean are shown by the red lines.

Repeatability of Normative Database:

for all 12 BNA scores, the means of Visit 1 and Visit 2 were not significantly different. ICC values ranged from 0.47 to 0.83, with an average of 0.71 (SD=0.10), see FIG. 22.

Normal Distribution of ΔBNA Scores in a Normative Database:

The BNA Analysis System's normative database includes ΔBNA scores from the two consecutive EEG-ERP sessions. The normative database's ΔBNA scores were found to adhere to a Gaussian distribution for all 12 combinations of stimuli and scores, as inferred from the histograms and the Q-Q plots (FIGS. 23 and 24).

Determination of SEM: The Computed 2SEM Ranged from 16.04 to 40.62 (average=26.9) BNA score points. As the Normative Database ΔBNA scores follow a Gaussian distribution, it may be concluded with about 95% certainty that ΔBNA scores which fall outside of the 2SEM range are not a result of random variation (FIG. 24).

Clinical Applications

Part A: Simulation

A subject was randomly selected from the normative database. The Target and Novel stimuli were then manipulated by gradually attenuating amplitude and increasing latency. This effectively simulated changes that can occur in a variety of clinical conditions. A Multi-channel Matching Pursuit was then utilized at all 64 simulated scalp locations.

The resulting changes in BNA Scores following successive manipulation steps were then calculated and evaluated against SEM values derived from the normative database.

FIG. 25 shows a reconstructed ERP at Fz channel of a randomly chosen healthy subject from the normative database following a 6-step graded manipulation (combined amplitude decline and latency delay) of the P300 component in response to the Novel stimulus. The top curve is the original non-manipulated trace.

The simulation results are shown in FIGS. 26A-B. FIG. 26A shows plots of 4 ΔBNA score values (Manipulation Level BNA score—baseline BNA score) as a function of the extent of manipulation. The boxed areas designate ±1SEM and ±2SEM thresholds derived from the normative BNA database. FIG. 26B shows the dependence of individual qualitative maps on the degree of manipulation. Red dots on group template designate scalp locations involved in event-pairs (joined by lines). Red dots on individual maps designates event-pairs common to the group template, the thickness of joining lines denoting how close the match is in terms of amplitude and timing.

As shown in FIGS. 26A-B, the individual qualitative maps became increasingly less complex and less resembling of the group template as manipulation progressed. Accordingly, the ΔBNA scores were generally shown to diminish in line with the extent of manipulation.

Part B—Cognitive Impairment Model

A pharmacological model study included 13 healthy volunteers of both genders, Aged 18-45. The volunteers were subjected to 3 Consecutive BNA sessions were, 1 week apart. A first session was used as a baseline, one of the two other sessions included administration of scopolamine (0.4 mg), and the other of the two other sessions included administration of placebo. The second and third sessions were at random order, double blind. ΔBNA Score values (Baseline—Placebo and Baseline—Drug) were evaluated against SEM values.

FIG. 27 shows pharmacological model results. Shown are Plots of the ΔBNA (Baseline—treatment) connectivity score values for the Novel response. Each symbol is a single subject, tested once following Drug and once following Placebo. Horizontal lines are ±1, 1.5 & 2SEM thresholds, derived from the normative BNA database.

The Results are presented for the Novel stimulus. Novelty processing is known to be particularly vulnerable to cognitive decline. Eight out of 13 patients receiving scopolamine had post-treatment BNA scores more than 2 SEM lower than the baseline score, as compared to only 2 patients receiving placebo.

Conclusions

The present example demonstrates that the BNA technique of the present embodiments has a high test-retest repeatability. The present example demonstrates that the BNA technique of the present embodiments can be utilized to follow clinically meaningful changes in brain activity of individual subjects. The present example demonstrates that a change in BNA Scores from baseline over time, as calculated in accordance with some embodiments of the present invention can aid for monitoring disease states, particularly for concussion management.

Example 3

Exemplified Experimental Study for Sport-Related Concussion

This experimental study evaluated the efficacy of BNA analysis of the present embodiments to discriminate between concussed and non-concussed athletes over multiple time periods.

Little is known about changes in brain activity and connectivity following a sport-related concussion. Event Related Potentials (ERPs), which are temporal reflections of electrophysiological response to stimuli, may provide valuable insight to the pathophysiological events that underlie concussion. The BNA pattern of the present embodiments can be utilized for identifying and optionally tracking the recovery following sport-related concussion.

A schematic flowchart of the employed technique is illustrated in FIG. 28. High density EEG data are collected while the subject performed specific computerized cognitive tasks. The EEG data are then processed according to some embodiments of the present invention and a set of spatio-temporal activity patterns representing the activated brain networks is extracted. The single subject patterns are scored against a task matched and age matched Reference Brain Network (N=>90) to generate a BNA score.

Methodology

Participants and Procedures

Participants comprised 35 concussed patients and 19 control athletes. University IRB was obtained prior to study. All athletes underwent computerized neurocognitive testing, symptom assessment, and electrophysiological (EEG/ERP) assessment while performing three cognitive tasks: 1) Auditory Oddball, 2) Visual GoNoGo, and 3) Sternberg Memory; within 10 days, 11-17 days, 18-24 days, and 25-31 days post-concussion.

Data Analysis

Brain networks associated with sport-related concussion were first identified. Interclass Correlation (ICC) values were calculated to evaluate the stability of the BNA scores in healthy controls across all post-concussion visits. The ability to discriminate the brain network activity between concussed athletes and matched controls was evaluated with a Receiver Operating Characteristic (ROC) analysis.

Results

The BNA corresponding to the "GO" event in the GoNogo task and the BNA corresponding to the "Frequent" event in the Auditory Oddball task demonstrated the best ability to discriminate between concussed athletes and matched controls. FIG. 29A shows the selected reference BNA for the Go/NoGo task, and FIG. 29B shows the selected reference BNA for the Auditory Oddball task.

The BNA scores related to the temporal unfolding of the network activity (absolute timing from stimuli and relative timing of electrophysiological events) were most sensitive to the concussive effect.

The InterClass Correlation (ICC) for the control groups revealed a high level of repeatability demonstrating stability of the BNA scores for this group across four visits. ICC scores ranged from 0.66-0.69.

FIGS. 30A-D show group average BNA scores (% similarity to the reference BNA) across 4 visits for the concussed group (n=35) and the control group (n=19). A significant segregation of BNA scores between the concussed and control group were observed on visit 1 (within an average of 7.7 days post-concussion) and converge across the follow up visits.

The sensitivity and specificity for the BNA patterns are shown in FIGS. 31A-D. ROC analysis demonstrated a high discrimination between concussed athletes and healthy controls. The sensitivity ranged from about 0.74 to about 0.85 and the specificity ranged from about 0.58 to about 0.68 with AUC values ranging from about 0.70 to about 0.76.

Example 4

Exemplified Feature Selection Procedure

A feature selection procedure was applied according to some embodiments of the present invention to reduce the dimensionality of a capsule network pattern.

Methods

Subjects

About 110 subjects (ages 14-24) were recruited from the following three centers: York University, University of Pittsburgh Medical Center (UPMC) and Vince & Associates Clinical Research (Kansas, USA). For the purpose of the study the Auditory Oddball, Auditory Go/No-Go, and Sternberg tasks were used. The training of the feature selection was performed on data from 35 concussed and 20 controls from UPMC.

Tasks

In the oddball task, three auditory stimuli were randomly presented in a probabilistic fashion, at an average rate of 1 stimulus every 1.5 sec. About 80% of the stimuli were pure tones of 2000 Hz ("standard"), about 10% of the stimuli were pure tones of 1000 Hz ("target"), and about 10% of the stimuli were environmental sounds ("novel"), such as telephone ringing or dog bark, different for each stimulus presentation. The subjects responded by pressing a button with his/her right index finger.

In the Auditory Go/No-Go task, for each trial, either a Go or a NoGo stimulus was presented. The No-Go stimulus was relatively rare (about 20% of the occurrences) in comparison to the Go stimulus. No-Go cues required subjects to inhibit a prepared motoric act and Go cues were the stimuli to which subjects were asked to respond as quickly as possible.

In the Sternberg memory task, the subjects were presented with a memory set which included several serially displayed stimuli. After a short retention interval, a probe stimulus was presented. The subjects were asked to press one key if the probe was present in the memory set and another key otherwise (50% "yes"). Difficulty level was manipulated by the number of stimuli in the memory set.

Data Analysis

Parcellation was applied to the activity related features to define capsules as further detailed hereinabove. Feature selection was applied to the capsules corresponding to all events of all subjects, to provide group characteristics followed by single-subject scoring. An event was defined as an extremum point in the spatiotemporal amplitude space and its associated surroundings. The features that characterize each subject's brain activity were defined as the sets of all capsules (peaks and encapsulated activity regions in time and space around the peak). The features were sorted by the combined sum of the area under the curve (AUC) of a receiver operating characteristic (ROC) curve and Intra Class-Correlation (ICC) using a forward model.

In a second study, the training set was applied to examine repeatability and negative predictive value (NPV). The NPV was defined as a summary statistic that describes the probability that subjects with a negative test result do not have the disease and are correctly diagnosed. In this study the features were sorted by the combined sum of the AUC and ICC values.

Results

FIG. 35 shows one example of extracted spatiotemporal peaks in different frequency bands for the No-Go stimulus.

The measures of differentiation (AUC) and repeatability (ICC) for each stimulus in the three cognitive tasks ranged between about 0.7 to 0.9 (except for the Target's ICC) and are given in Table 3, below.

TABLE 3

| Stimulus | AUC | ICC |
|---|---|---|
| Go | 0.78 | 0.9 |
| NoGo | 0.8 | 0.73 |
| Frequent | 0.77 | 0.86 |
| Target | 0.74 | 0.64 |
| Novel | 0.79 | 0.67 |
| Sternberg stimulus | 0.74 | 0.74 |

Differentiation is graphically displayed in FIGS. 36A-C for exemplary stimuli from the different tasks (blue line=healthy controls; red line=concussed). In FIGS. 36A-C, a clear separation is shown between concussed and healthy controls in the first visit in all three stimulus types. This separation was diminished in subsequent visits but was still evident in the second visit in the Novel (FIG. 36A) and Sternberg (FIG. 36C) stimuli.

For the second study, training for NPV allowed to extract capsule networks that identify an individual without concussion with high precision. That is, the capsule networks accurately determined that an individual with a negative test result based on the networks is indeed not concussed. The features achieved a good NPV score of 0.72.

It was found by the present inventors that capsule networks which are the outcome of training for NPV can aide in decision making. For example, when the subject is an athlete diagnosed as having a sport-related concussion, the capsule networks can aid in deciding whether the athlete can return to sport activity.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCE

[1] F. H. Duffy, "Topographic display of evoked potentials: clinical applications of brain electrical activity mapping (BEAM)", Annals of the New York Academy of Science, vol. 388, pp. 183-96, June, 1982.

[2] D. Lehmann, "Principles of spatial analysis", in Methods of Analysis of Brain Electrical and Magnetic Signals, A. S. Gevins, A. Remond, Eds. Amsterdam: Elsevier, 1987. pp. 309-54.

[3] K. J. Friston, J. T. Ashburner, S. J. Kiebel, T. E. Nichols and W. D. Penny, "Statistical parametric mapping: the analysis of functional brain images", London: Academic Press, 2001.

[4] K. E. Stephan, L. M. Harrison, S. J. Kiebel, O. David, W. D. Penny and K. J. Friston, "Dynamic causal models of neural system dynamics: current state and future extensions", Journal of Biosciences, vol. 32, no. 1, pp. 129-144, January 2007.

[5] C. M. Michel, M, Seeck and T. Landis. "Spatio-temporal dynamics of human cognition", News in Physiological Sciences, vol. 14, pp. 206-214, October 1999.

[6] D. Brunet, M. M. Murray and C. M. Michel, "Spatiotemporal analysis of multichannel EEG: CARTOOL", Computational Intelligence & Neuroscience, vol. 2011, pp. 813-870, January 2011.

[7] C. D. Woody, "Characterization of an adaptive filter for the analysis of variable latency neuroelectric signals", Medical & Biological Engineering, vol. 5, no. 6, pp. 539-554, November 1967.

[8] R. Bellman and R. Kalaba, "On adaptive control processes", IRE Trans on Automatic Control, vol. 4, no. 2 pp. 1-9, November 1959.

[9] A. Efrat, Q. Fan and S. Venkatasubramanian, "Curve matching, time warping and light fields: New algorithms for computing similarity between curves", Journal of Mathematical & Imaging Visualization, vol. 27, no. 3, pp. 203-216, April 2007.

[10] D. Comaniciu and P. Meer, "Mean Shift: A robust approach toward feature space analysis", IEEE Trans on Pattern Analysis and Machine Intelligence, vol. 24, no. 5, pp. 603-619, May 2002.

[11] J. Polich, "Updating p300: An integrative theory of p3a and p3b", Clinical Neurophysiology, vol. 118, no. 10, pp. 2128-2148, October 2007.

[12] D. J. Linden, "The P300: Where in the Brain Is It Produced and What Does It Tell. Us?" The Neuroscientist, vol. 11 no. 6 pp. 563-576, November 2005.

What is claimed is:

1. A method of configuring a local brain stimulation tool, the method comprising:

obtaining a reference brain network activity (BNA) pattern, and a BNA pattern describing a neurophysiological state of a subject, each of said BNA patterns having a plurality of nodes and each node representing a brain location and at least one brain wave frequency;

comparing said BNA patterns; and configuring the local brain stimulation tool to apply local brain stimulation at a frequency selected based on said comparison, wherein the method further comprises configuring said tool to apply said local brain stimulation at a location selected based on said comparison, wherein said comparison is node-wise, and wherein said selected location corresponds to a node that exists in said reference and missing in said BNA pattern describing said neurophysiological state of the subject.

2. The method of claim 1, further comprising configuring said tool to apply said local brain stimulation at a time or synchronization selected based on said comparison.

3. The method according to claim 1, further comprising correcting said location using a technique selected from the group consisting of a source localization procedure, Cortical Potential Imaging (CPI), and Cortical Source Density (CSD).

4. The method of claim 1, further comprising operating said local brain stimulation tool to apply said local brain stimulation to the subject thereby to treat a brain disorder thereof, wherein both a frequency and a location of said stimulation is selected based on said comparison.

5. The method according to claim 4, wherein said local brain stimulation tool is operated to apply said local brain stimulation at a time selected based on said comparison.

6. The method according to claim 4, wherein said local brain stimulation tool is operated to apply local brain stimulation at a plurality of different brain locations and a plurality of different frequencies.

7. The method according to claim 4, wherein said local brain stimulation tool is operated to apply local brain stimulation at a plurality of different brain locations and a plurality of different times.

8. The method according to claim 4, wherein said local brain stimulation tool is operated to apply said local brain stimulation at a plurality of different brain locations, a plurality of different frequencies and a plurality of different times.

9. The method according to claim 4, wherein said local brain stimulation tool is operated to apply said local brain stimulation at a plurality of different brain locations, at a same frequency but at a plurality of different times.

10. The method according to claim 1, wherein said comparison is node-wise, wherein said selected location corresponds to a node that exists in both said BNA patterns, and wherein said selected frequency exists in said node of said reference BNA and is missing or suppressed in said BNA pattern describing said neurophysiological state of the subject.

11. The method according to claim 1, further comprising obtaining a post-stimulation BNA pattern describing a neurophysiological state of the subject following said stimulation, comparing said post-stimulation BNA pattern with said BNA pattern describing said neurophysiological state before said stimulation, and assessing an effect of said stimulation based on said comparison.

12. The method according to claim 1, wherein at least one node of said BNA patterns defines a capsule representing a spatiotemporal activity region in the brain.

13. The method according to claim 1, further comprising constructing at least one of said BNA patterns.

14. The method according to claim 13, wherein said constructing said at least one of said BNA patterns comprises:

receiving neurophysiological data;

identifying activity-related features in the data; and defining at least a portion of said activity-related features as nodes of said BNA pattern.

15. The method according to claim 13, wherein said constructing said at least one of said BNA patterns comprises:

receiving neurophysiological data;

identifying activity-related features in said data;

parceling the data according to said activity-related features to define a plurality of capsules, each representing a spatiotemporal activity region in the brain; and defining at least a portion of said capsules as nodes of said BNA pattern.

16. The method according to claim 15, further comprising determining inter-capsule relations among said capsules, and defining connectivity weights between said nodes of said BNA pattern using said inter-capsule relations.

17. The method according to claim 13, wherein said constructing said at least one of said BNA patterns comprises:

receiving neurophysiological data;

identifying activity-related features in said data;

parceling the data according to said activity-related features to define a plurality of capsules, each representing a spatiotemporal activity region in the brain;

clustering the data according to said capsules, to provide a plurality of capsule clusters; and defining at least a portion of said capsule clusters and/or representations thereof as nodes of said BNA pattern.

18. The method according to claim 17, wherein said representations of said clusters comprises capsular representations of said clusters.

19. The method according to claim 1, wherein the local stimulation tool comprises at least one of a non-invasive stimulation tool, a transcranial stimulation tool, a transcranial electrical stimulation tool, a transcranial magnetic stimulation tool, a repetitive Transcranial Magnetic Stimulation (rTMS) tool, a deep Transcranial magnetic stimulation (dTMS) tool, a multichannel TMS and multichannel (dTMS) tool, a transcranial electrical stimulations (tES) tool, a Transcranial direct current stimulation (tDCS) tool, a Transcranial alternate current stimulation (tACS) tool, a Transcranial random noise stimulation (tRNS) tool, a High definition tES (HD-tES) tool, a High definition tDCS (HD-tDCS) tool, a multichannel tES tool, a focused ultrasound stimulation (FUS) tool, an electroconvulsive therapy (ECT) tool, an invasive stimulation tool, a Deep brain stimulation (DBS) tool, a multifocal deep brain stimulation tool, a laser stimulation tool, and an electrocortical stimulation tool configured to apply electrocortical stimulation on a cortex.

20. The method according to claim 1, wherein said brain stimulation tool is configured to apply both transcranial stimulation and deep brain stimulation, and wherein the method controls the brain stimulation tool to apply the transcranial stimulation to control activation thresholds for the deep brain stimulation.

21. A system for treating a subject, the system comprises:
(a) a data processing system configured for:
obtaining a reference brain network activity (BNA) pattern, and a BNA pattern describing a neurophysiological state of the subject, each of said BNA patterns having a plurality of nodes and each node representing a brain location and at least one brain wave frequency; and
comparing said BNA patterns; and
(b) a controller connectable to a brain stimulation tool and configured for controlling said brain stimulation tool to apply local brain stimulation at a location and a frequency selected based on said comparison, wherein said comparison is node-wise, and wherein said selected location corresponding to a node that exists in said reference and missing in said BNA pattern describing said neurophysiological state of the subject.

22. A method of configuring a local brain stimulation tool, the method comprising:
obtaining a reference brain network activity (BNA) pattern, and a BNA pattern describing a neurophysiological state of a subject, each of said BNA patterns having a plurality of nodes and each node representing a brain location and at least one brain wave frequency;
comparing said BNA patterns; and
configuring the local brain stimulation tool to apply local brain stimulation at a frequency selected based on said comparison,
wherein the method further comprises configuring said tool to apply said local brain stimulation at a location selected based on said comparison, wherein said comparison is node-wise, wherein said selected location corresponds to a node that exists in both said BNA patterns, and wherein said selected frequency exists in said node of said reference BNA and is missing or suppressed in said BNA pattern describing said neurophysiological state of the subject.

23. A method of configuring a local brain stimulation tool, the method comprising:
obtaining a reference brain network activity (BNA) pattern, and a BNA pattern describing a neurophysiological state of a subject, each of said BNA patterns having a plurality of nodes and each node representing a brain location and at least one brain wave frequency;
comparing said BNA patterns; and
configuring the local brain stimulation tool to apply local brain stimulation at a frequency selected based on said comparison;
wherein the method further comprises constructing at least one of said BNA patterns, said constructing said at least one of said BNA patterns comprising:
receiving neurophysiological data;
identifying activity-related features in said data;
parceling the data according to said activity-related features to define a plurality of capsules, each representing a spatiotemporal activity region in the brain;
clustering the data according to said capsules, to provide a plurality of capsule clusters; and
defining at least a portion of said capsule clusters and/or representations thereof as nodes of said BNA pattern.

24. A method of configuring a local brain stimulation tool, the method comprising:
obtaining a reference brain network activity (BNA) pattern, and a BNA pattern describing a neurophysiological state of a subject, each of said BNA patterns having a plurality of nodes and each node representing a brain location and at least one brain wave frequency;
comparing said BNA patterns; and
configuring the local brain stimulation tool to apply local brain stimulation at a frequency selected based on said comparison;
wherein the method further comprises constructing at least one of said BNA patterns, said constructing said at least one of said BNA patterns comprising:
receiving neurophysiological data;
identifying activity-related features in said data;
parceling the data according to said activity-related features to define a plurality of capsules, each representing a spatiotemporal activity region in the brain; and
defining at least a portion of said capsules as nodes of said BNA pattern;
wherein the method additionally comprises determining inter-capsule relations among said capsules, and defining connectivity weights between said nodes of said BNA pattern using said inter-capsule relations.

* * * * *